US006852334B1

(12) United States Patent
Cullis et al.

(10) Patent No.: US 6,852,334 B1
(45) Date of Patent: Feb. 8, 2005

(54) CATIONIC PEG-LIPIDS AND METHODS OF USE

(75) Inventors: Pieter R. Cullis, Vancouver (CA); Tao Chen, Richmond (CA); David B. Fenske, Surrey (CA); Lorne R. Palmer, Vancouver (CA); Kim Wong, Vancouver (CA)

(73) Assignee: The University of British Columbia, Vancouver (CA)

( * ) Notice: Subject to any disclaimer, the term of this patent is extended or adjusted under 35 U.S.C. 154(b) by 0 days.

(21) Appl. No.: 09/553,639

(22) Filed: Apr. 20, 2000

Related U.S. Application Data
(60) Provisional application No. 60/130,151, filed on Apr. 20, 1999.

(51) Int. Cl.$^7$ .......................... A61K 9/127; C12N 15/88
(52) U.S. Cl. .................... 424/450; 435/320.1; 435/455; 435/458; 514/44
(58) Field of Search .............................. 435/320.1, 325, 435/455, 458; 424/450; 514/44

(56) References Cited

U.S. PATENT DOCUMENTS

| | | | | |
|---|---|---|---|---|
| 5,534,259 A | * | 7/1996 | Zalipsky et al. | 424/450 |
| 5,639,473 A | * | 6/1997 | Grinstaff et al. | 424/450 |
| 5,766,902 A | * | 6/1998 | Craig et al. | 435/455 |
| 5,846,530 A | * | 12/1998 | Soon-Shiong et al. | 424/93.7 |
| 5,885,613 A | * | 3/1999 | Holland et al. | 424/450 |
| 5,976,567 A | * | 11/1999 | Wheeler et al. | 424/450 |
| 5,981,501 A | * | 11/1999 | Wheeler et al. | 514/44 |
| 6,177,274 B1 | * | 1/2001 | Park et al. | 435/455 |
| 6,245,530 B1 | * | 6/2001 | Alitalo et al. | 435/69.4 |
| 6,284,267 B1 | * | 9/2001 | Aneja et al. | 424/450 |
| 6,287,591 B1 | * | 9/2001 | Semple et al. | 424/450 |
| 6,300,317 B1 | * | 10/2001 | Szoka, Jr. et al. | 514/44 |
| 6,316,024 B1 | * | 11/2001 | Allen | 424/450 |
| 6,320,017 B1 | * | 11/2001 | Ansell | 528/310 |
| 6,395,254 B1 | * | 5/2002 | Sinn | 424/1.69 |

FOREIGN PATENT DOCUMENTS

| | | |
|---|---|---|
| WO | WO 99/05303 | 2/1966 |
| WO | WO 98/16202 | 4/1998 |
| WO | WO 98/46208 | 10/1998 |
| WO | WO 98/51285 | 11/1998 |
| WO | WO 99/05094 | 2/1999 |
| WO | WO 99/08997 | * 2/1999 |
| WO | WO 99/65461 | 12/1999 |
| WO | WO 00/43043 | 7/2000 |

OTHER PUBLICATIONS

Samuel Zalipsky et al., "Long Circulating, Cationic Liposomes Containing Amino–Peg–Phosphatidylethanolamine" Febs Letters, Elsevier Science Publishers, Amsterdam, NL, vol. 353, 1994, pp. 71–74, XP002920144.

Tao Chen et al., "Fluorescent–Labeled Poly(ethylene glycol) Lipid Conjugates with Distal Cationic Headgroups", Bioconjugate Chemistry, Online!, vol. 11, No. 3, May 2000, pp. 433–437, XP 002157295.

Santanu Bhattacharya et al., "Synthesis of novel cationic lipids with oxyethylene spacers at the linkages between hydrocarbon chains and pseudoglyceryl backbone", Tetrahedron Letters, Elsevier Science Publishers, Amsterdam, NL., vol. 40, No. 46, Nov. 12, 1996, pp. 8167–8171, XP004180445.

K. Anwer et al., "Optimization of Cationic Lipid/DNA Complexes for Systemic Gene Transfer to Tumor Lesions", Journal of Drug Targeting, Harwood Academic Publishers GMBH, DE, vol. 8, No. 2, 2000, pp. 125–135, XP000951678.

Atsuhide Mori et al., "Stabilization and Regulated Fusion of Liposomes Containing a Cationic Lipid using Amphipathic Polyethyleneglycol Derivatives" Journal of Liposome Research, US, Marcel Dekker, New York, vol. 8, No. 2, May 1, 1998, pp. 195–211, XP000752693.

Aruna Nathan et al., "Copolymers of Lysine and Polyethylene Glycol: A New Family of Functionalized Drug Carriers", Bioconjugate Chemistry, US, American Chemical Society, Washington, vol. 4, No. 1, 1993, pp. 54–62, XP000336592.

Joseph Jagur–Grodzinski et al., "Biomedical application of functional polymers", Reactive & Functional Polymers, NL, Elsevier Science Publishers BV, vol. 39, No. 2, Feb. 15, 1999, pp. 99–138, XP004160680.

Vladimir S. Trubetskoy et al., "New Approaches in the Chemical Design of Gd–Containing Liposomes for use in Magnetic Resonance Imaging of Lymph Nodes", Journal of Liposome Research, US, Marcel Dekker, New York, vol. 4, No. 2, 1994, pp. 961–980, XP000619021.

Thomas Haselgrubler et al., "Synthesis and Applications of a New Poly(ethylene glycol) Derivative for the Crosslinking of Amines with Thiols", Bioconjugate Chemistry, US, American Chemical Society, Washington, vol. 6, No. 3, May 1, 1995, pp. 242–1802, XP000505483.

(List continued on next page.)

*Primary Examiner*—Dave T. Nguyen
(74) *Attorney, Agent, or Firm*—Oppedahl & Larson LLP

(57) ABSTRACT

The present invention provides cationic-polymer-lipid conjugates (CPLs) such as distal cationic-poly(ethylene glycol)-lipid conjugates which can be incorporated into conventional and stealth liposomes or other lipid-based formulation for enhancing cellular uptake. The CPLs of the present invention comprise a lipid moiety; a hydrophilic polymer; and a polycationic moiety. Method of increasing intracellular delivery of nucleic acids are also provided.

43 Claims, 60 Drawing Sheets

OTHER PUBLICATIONS

Veska Toncheva et al., "Block Copolymers with pH–Dependent Secondary Structure", Journal of Controlled Release, vol. 48, No. 2–3, Oct. 1997, pp. 301–302, XP002157296.

Vladimir S. Trubetskoy et al., "New Approaches in the Chemical Design of Gd–Containing Liposomes for use in Magnetic Resonance Imaging of Lymph Nodes", Journal of Liposome Research, 1994, vol. 4, No. 2, pp. 961–983, XP000978705.

M. Macian et al., "Preliminary studies of toxic effects of non–ionic sufactants derived from lysine", Toxicology, Jan. 8, 1996, vol. 106, No. 1–3, pp. 1–9, XP000978704.

Volkmar Weissig et al., "Long–circulating gadolinium–loaded liposomes:potential use for magnetic resonance imaging of the blood pool", Colloids and Surface B (Biointerfaces), Oct. 2000, Elsevier, Netherlands, vol. 18, No. 3–4, pp. 293–299, XP000971876.

* cited by examiner

Fractionation of DOPE/DODAC/CPL4[3.4K]/PEGCerC20/Rho-PE

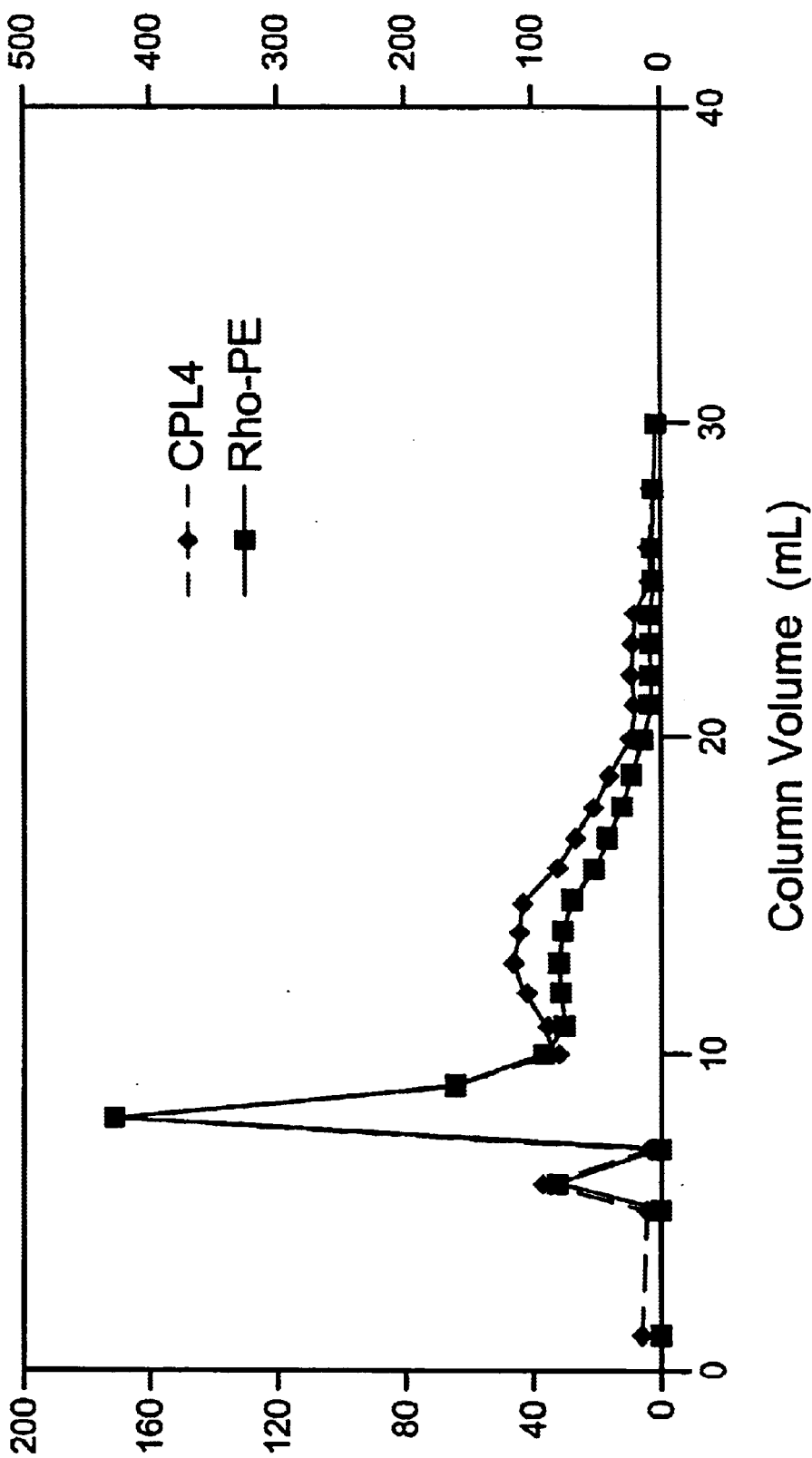
Fig. 8b Fractionation of DOPE/DODAC/CPL4[1K]/PEGCerC20/Rho-PE (79.5 / 6 / 4 / 10 / 0.5)

Fractionation of
DOPE/DODAC/CPL4[3.4K]/PEGCerC20/Rho-PE
(71.5 / 6 / 12 / 10 / 0.5)

Fig. 23a

| Sample Number | Lipid Composition | Mol% Composition | CPL |
|---|---|---|---|
| DBF1102-1 | DOPC/DODAC/PEG-Cer-C20 | 84/6/10 (0.5 Rho-PE) | d-DSPE-CPL-Q5 |
| DBF1102-2 | DOPE/DODAC/PEG-Cer-C20 | 84/6/10 (0.5 Rho-PE) | d-DSG-CPL-Q5 |
| | | | d-DSPE-CPL-M |
| | | | d-DSPE-CPL-D |
| | | | d-DSG-CPL-D |
| | | | d-DSPE-CPL-T1 |
| | | | d-DSPE-CPL-Q5 |
| | | | d-DSG-CPL-Q5 |
| | | | d-DSPE-CPL-Q1 |
| | | | d-DSPE-CPL-O(+8) |
| DBF1124-2 | DOPC/DODAC/PEG-Cer-C20 | 90/6/4 (0.5 Rho-PE) | d-DSPE-CPL-Q5 |
| DBF1124-3 | DOPC/DODAC/PEG-Cer-C20 | 86/6/8 (0.5 Rho-PE) | d-DSPE-CPL-Q5 |

Fig. 23b

| Sample Number | CPL | Initial CPL/LUV | % Insertion | Final Mol% Insertion |
|---|---|---|---|---|
| DBF1102-1 | d-DSPE-CPL-Q5 | 0.071 | 62 | 4.4 |
| | d-DSG-CPL-Q5 | 0.057 | 39 | 2.2 |
| | | 0.11 | 37 | 4.2 |
| | | 0.17 | 36 | 6.2 |
| DBF1102-2 | d-DSPE-CPL-M | 0.082 | 79 | 6.5 |
| | d-DSPE-CPL-D | 0.070 | 80 | 5.6 |
| | d-DSG-CPL-D | 0.1 | 24 | 2.4 |
| | d-DSPE-CPL-T1 | 0.023 | 77 | 1.8 |
| | | 0.046 | 75 | 3.5 |
| | | 0.070 | 74 | 5.2 |
| | | 0.093 | 62 | 5.7 |
| | d-DSPE-CPL-Q5 | 0.012 | 69 | 0.81 |
| | d-DSPE-CPL-Q5 | 0.024 | 76 | 1.8 |
| | d-DSPE-CPL-Q5 | 0.047 | 72 | 3.4 |
| | d-DSPE-CPL-Q5 | 0.023 | 79 | 1.8 |
| | d-DSPE-CPL-Q5 | 0.071 | 70 | 4.9 |

Fig. 23c

| Sample Number | CPL | Initial CPL/LUV | % Insertion | Final Mol% Insertion |
|---|---|---|---|---|
| DBF1102-2 | d-DSPE-CPL-Q5 | 0.095 | 68 | 6.5 |
| | d-DSPE-CPL-Q5 | 0.045 | 78 | 3.5 |
| | d-DSPE-CPL-Q5 | 0.14 | 50 | 7.0 |
| | d-DSPE-CPL-Q5 | 0.016 | 72 | 1.1 |
| | d-DSG-CPL-Q5 | 0.057 | 27 | 1.6 |
| | | 0.11 | 25 | 2.8 |
| | | 0.17 | 29 | 4.9 |
| | d-DSPE-CPL-Q1 | 0.022 | 80 | 1.7 |
| | | 0.043 | 78 | 3.4 |
| | | 0.043 | 83 | 3.6 |
| | | 0.065 | 69 | 4.4 |
| | | 0.086 | 64 | 5.5 |
| | d-DSPE-CPL-O(+8) | 0.013 | 75 | 0.95 |
| DBF1124-2 | d-DSPE-CPL-Q5 | 0.071 | 71 | 5.1 |
| DBF1124-3 | d-DSPE-CPL-Q5 | 0.071 | 67 | 4.7 |

Fig. 24a

| Sample Number | Lipid Composition | Mol% Composition | CPL |
|---|---|---|---|
| DBF1207-1 | DOPC/DODAC/PEG-Cer-C20 | 84/6/10 (0.25 Rho-PE) | |
| DBF1207-2 | DOPC/DODAC/PEG-Cer-C14 | 84/6/10 (0.25 Rho-PE) | |
| DBF1207-3 | DOPC/DODAC/PEG-Cer-C8 | 79/6/15 (0.25 Rho-PE) | |
| DBF1207-4 | DOPE/DODAC/PEG-Cer-C20 | 84/6/10 (0.25 Rho-PE) | d-DSPE-CPL-M |
| | | | d-DSPE-CPL-T |
| DBF1207-5 | DOPE/DODAC/PEG-Cer-C14 | 84/6/10 (0.25 Rho-PE) | d-DSPE-CPL-T |
| DBF1207-6 | DOPE/DODAC/PEG-Cer-C8 | 79/6/15 (0.25 Rho-PE) | d-DSPE-CPL-T |
| DBF0201-1 | DOPE/DODAC/PEG-Cer-C14 | 84/6/10 (0.25 Rho-PE) | d-DSPE-CPL-Q1 |
| DBF0310-1 | DOPC | 99.5 (0.5 Rho-PE) | d-DSPE-CPL-Q1 |
| | | | d-DSPE-CPL-Q1 |
| DBF0310-2 | DOPC/Chol | 54.5/45 (0.5 Rho-PE) | d-DSPE-CPL-Q1 |
| | | | d-DSPE-CPL-Q5 |
| DBF0303-2 | DOPC/PEG-Cer-C20 | 89.5/10 (0.5 Rho-PE) | d-DSPE-CPL-Q1 |
| | | | d-DSPE-CPL-Q5 |
| DBF0303-4 | DOPC/Chol/PEG-Cer-C20 | 44.5/45/10 (0.5 Rho-PE) | d-DSPE-CPL-Q1 |
| | | | d-DSPE-CPL-Q5 |

Fig. 24b

| Sample Number | CPL | Initial CPL/LUV | % Insertion | Final Mol% Insertion |
|---|---|---|---|---|
| DBF1207-4 | d-DSPE-CPL-M | 0.05 | 58-62 | 2.9-3.1 |
| | d-DSPE-CPL-T | 0.049 | 61 | 3.0 |
| DBF1207-5 | d-DSPE-CPL-T | 0.049 | 80 | 3.0 |
| DBF1207-6 | d-DSPE-CPL-T | 0.049 | 77 | 3.8 |
| | d-DSPE-CPL-Q1 | 0.022 | 75 | 1.6 |
| | | 0.043 | 78 | 3.3 |
| | | 0.065 | 78 | 5.0 |
| | | 0.086 | 74 | 6.4 |
| DBF0201-1 | d-DSPE-CPL-Q1 | 0.022 | 82 | 1.8 |
| | | 0.043 | 81 | 3.5 |
| | | 0.065 | 77 | 5.0 |
| | | 0.086 | 72 | 6.2 |

Fig. 24c

| Sample Number | CPL | Initial CPL/LUV | % Insertion | Final Mol% Insertion |
|---|---|---|---|---|
| DBF0310-1 | d-DSPE-CPL-Q1 | 0.065 | 65 | 4.2 |
| | d-DSPE-CPL-Q5 | 0.034 | 84 | 2.9 |
| DBF0310-2 | d-DSPE-CPL-Q1 | 0.065 | 58 | 3.8 |
| | d-DSPE-CPL-Q5 | 0.034 | 84 | 2.9 |
| DBF0303-2 | d-DSPE-CPL-Q1 | 0.065 | 57 | 3.7 |
| | d-DSPE-CPL-Q5 | 0.034 | 70 | 2.4 |
| DBF0303-4 | d-DSPE-CPL-Q1 | 0.065 | 45 | 2.9 |
| | d-DSPE-CPL-Q5 | 0.034 | 75 | 2.5 | a: Nε-dansyl-L-lysine, triethylamine, methanol, chloroform, 3h
b: NHS, DCC, chloroform, 2h
c: DSPE, triethylamine, chloroform, 4h
d: TFA, chloroform, 4h
e: NαNε-di-tBoc-L-lysine-N-hydroxysuccinimide ester, triethylamine, chloroform, 3h

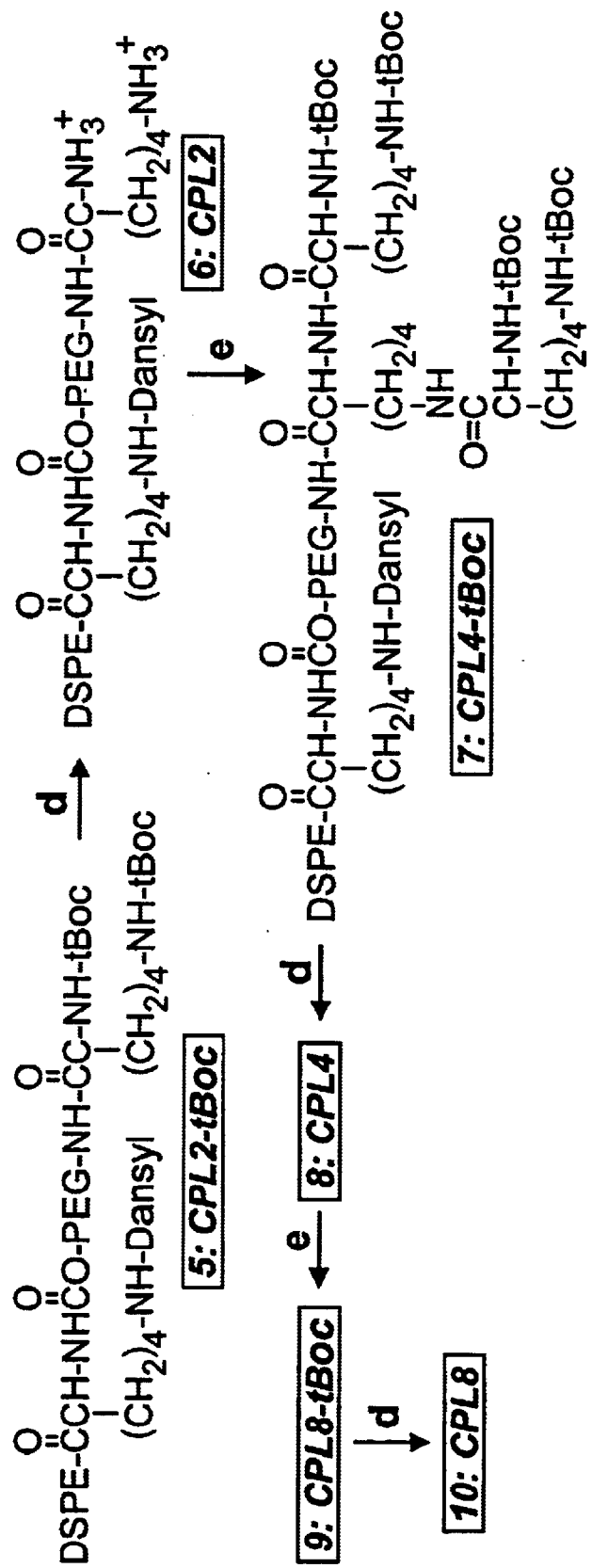

CATIONIC PEG-LIPIDS AND METHODS OF USE

RELATED APPLICATIONS

This application claims priority to U.S. Provisional Patent Application Serial No. 60/130,151 filed Apr. 20, 1999, the teachings of which are incorporated herein by reference in their entirety for all purposes.

FIELD OF THE INVENTION

This invention relates to cationic lipid conjugates, and more particularly, to cationic polymer lipid conjugates and lipid-based drug formulations thereof, containing one or more bioactive agents.

BACKGROUND OF THE INVENTION

Current vectors for gene delivery and gene therapy are comprised of viral based and non-viral based systems. Lipid-based non-viral systems include cationic lipid plasmid DNA complexes. Limitations of these systems include large sizes, toxicity and instability of the complexes in the serum. Unfortunately, the foregoing drawbacks limit the applications for these complexes.

Researchers have devoted tremendous effort to the design of long circulation stealth liposomes that can be used for systemic delivery (see, Papahadjopoulos, D. et al., Proc. Natl. Acad. Sci. 88:11460–11464 (1991); Klibanov, A. L. et al., J. Liposome Res., 2:321 (1992); Woodle, M. C. et al., Biochim. Biophys. Acta., 1113:171(1992); Torchilin, V. P. et al., In: Stealth Liposomes. Ed. By D. Lasic, F. Martin. CRC Press, Boca Raton, Fla., pp. 51–62 (1995); Allen, T. M. et al., Biochim. Biophys. Acta., 1237:99–108 (1995) and Zalipsky, S. et al., J. Controlled Release, 39:153–161 (1996)). In certain instances, and depending on the formulation, stealth liposomes are often comparatively inefficient at facilitating cellular uptake and therefore the therapeutic efficacy is reduced.

In general, the molecular mechanism of liposomal longevity in vivo can be attributed to steric hindrance resulting from hydrophilic polymer surface barriers. The hydrophilic polymer barriers prevent or reduce the rate of the adsorption of macromolecules from the blood and sterically inhibit both electrostatic and hydrophobic interactions between liposomes and blood components. Thus, although the longevity of stealth liposomes has been increased by the insertion of hydrophilic polymers, the cellular uptake of the stealth liposomes often is inefficient.

Over the past decade, it has also become clear that liposomal systems possessing cationic lipids are highly effective transfection agents in vitro (Felgner, P. L. et al., Nature 337:387–388 (1989); Felgner, P. L. et al., Proceedings of the National Academy of Sciences of the United States of America 84:7413–7417 (1987)). The addition of cationic liposomes to plasmid DNA gives rise to large DNA-lipid complexes that possess excellent transfection properties in vitro, but which are ineffective in vivo due to their rapid clearance from the circulation by cells of the reticuloendothelial system (RES). The need for a non-viral lipid-based system capable of systemic delivery of genes to cells led to the recent development of stabilized plasmid-lipid particles (SPLPs) (Wheeler, J. J. et al., Gene Therapy 6:271–281 (1999)). These particles are small (about 70 nm), contain a single copy of a plasmid vector, possess stealth properties resulting from a surface coating of poly (ethyleneglycol) (PEG), and protect DNA from degradation by serum nucleases.

Enhancing intracellular delivery of liposomes and/or their contents represents one of the major remaining problems in the development of the next generation of drug delivery systems. In order to optimize the delivery of drugs (conventional or genetic) in vivo, general methods for increasing the interactions of liposomes with cells need to be developed. To date, attempts include the use of specific targeting information on the liposome surface, such as an antibody (see, Meyer, O. et al., Journal of Biological Chemistry 273:15621–15627 (1998); Kao, G. Y. et al., Cancer Gene Therapy 3:250–256 (1996); Hansen, C. B. et al., Biochimica et Biophysica Acta 1239: 133–144 (1995)), vitamin- (see, Gabizon, A. et al., Bioconjugate Chemistry 10:289–298 (1999); Lee, R. J. et al., Journal of Biological Chemistry 269:3198–3204 (1994); Reddy, J. A. et al., Critical Reviews in Therapeutic Drug Carrier Systems 15:587–627 (1998); Holladay, S. R. et al., Biochimica et Biophysica Acta 1426:195–204 (1999); Wang, S. et al., Journal of Controlled Release 53:39–48 (1998)), oligopeptide- (see, Zalipsky, S. et al., Bioconjugate Chemistry 6:705–708 (1995); Zalipsky, S. et al., Bioconjugate Chemistry 8.111–118 (1997)), or the use of oligosaccharide constructs specific for a particular membrane protein or receptor. Unfortunately, these methods have not been successful in achieving this goal, despite promising in vitro results. While specific targeting of liposomes to tissues remains an important area of research, other approaches may also provide significant improvements in the effectiveness of liposomal carriers.

In view of the foregoing, what is needed in the art is a lipid-based drug formulation with increased longevity coupled with increased cellular uptake. The present invention satisfies this and other needs.

SUMMARY OF THE INVENTION

In certain aspects, the present invention relates to new conjugates that can be incorporated or inserted into stabilized plasmid lipid particles to enhance transfection efficiencies. The conjugates of the present invention possess a lipid anchor for anchoring the conjugate into the bilayer lipid particle, wherein the lipid anchor is attached to a non-immunogenic polymer, such as a PEG moiety, and wherein the non-immunogenic polymer is, in turn, attached to a polycationic moiety, such as a positively charged moiety. As such, the present invention provides a compound of Formula I:

In Formula I, "A" is a lipid moiety attached to a non-immunogenic polymer. "W," in Formula I, is a non-immunogenic polymer, and "Y", in Formula I, is a polycationic moiety.

In certain preferred embodiments, the compounds of Formula I contain groups that give rise to compounds having the general structure of Formula II:

In Formula II, "A" is a lipid, such as a hydrophobic lipid. In Formula II, "X" is a single bond or a functional group that covalently attaches the lipid to at least one ethylene oxide unit, i.e., (—$CH_2$—$CH_2$—O—). In Formula II, "Z" is a single bond or a functional group that covalently attaches the at least one ethylene oxide unit to a cationic group. In Formula II, "Y" is a polycationic moiety. In Formula II, the index "n" is an integer ranging in value from about 6 to about 160.

In other aspects, the present invention relates to a lipid-based drug formulation comprising:

(a) a compound having Formula I $$A-W-Y \qquad I$$

wherein: A, W and Y have been defined;

(b) a bioactive agent; and (c) a second lipid.

In certain embodiments, the lipid-based drug formulation is in the form of a liposome, a micelle, a virosome, a lipid-nucleic acid particle, a nucleic acid aggregate and mixtures thereof. In certain other embodiments, the bioactive agent is a therapeutic nucleic acid or other drugs.

In yet other aspects, the present invention relates to a method for increasing intracellular delivery of a lipid-based drug delivery system, comprising: incorporating into the lipid-based drug delivery system a compound of Formulae I or II, thereby increasing the intracellular delivery of the lipid-based drug delivery system.

Additional aspects and advantages of the present invention will be apparent when read with the following detailed description and the accompanying drawings.

DEFINITIONS

The term "lipid" refers to a group of organic compounds that include, but are not limited to, esters of fatty acids and are characterized by being insoluble in water, but soluble in many organic solvents. They are usually divided into at least three classes: (1) "simple lipids" which include fats and oils as well as waxes; (2) "compound lipids" which include phospholipids and glycolipids; (3) "derived lipids" such as steroids.

The term "vesicle-forming lipid" is intended to include any amphipathic lipid having a hydrophobic moiety and a polar head group, and which by itself can form spontaneously into bilayer vesicles in water, as exemplified by most phospholipids.

The term "vesicle-adopting lipid" is intended to include any amphipathic lipid which is stably incorporated into lipid bilayers in combination with other amphipathic lipids, with its hydrophobic moiety in contact with the interior, hydrophobic region of the bilayer membrane, and its polar head group moiety oriented toward the exterior, polar surface of the membrane. Vesicle-adopting lipids include lipids that on their own tend to adopt a non-lamellar phase, yet which are capable of assuming a bilayer structure in the presence of a bilayer-stabilizing component. A typical example is DOPE (dioleoylphosphatidylethanolamine). Bilayer stabilizing components include, but are not limited to, polyamide oligomers, peptides, proteins, detergents, lipid-derivatives, PEG-lipid derivatives such as PEG coupled to phosphatidylethanolamines, and PEG conjugated to ceramides (see, U.S. application Ser. No. 08/485,608, now U.S. Pat. No. 5,885,613, which is incorporated herein by reference).

The term "amphipathic lipid" refers, in part, to any suitable material wherein the hydrophobic portion of the lipid material orients into a hydrophobic phase, while the hydrophilic portion orients toward the aqueous phase. Amphipathic lipids are usually the major component of a lipid vesicle. Hydrophilic characteristics derive from the presence of polar or charged groups such as carbohydrates, phosphato, carboxylic, sulfato, amino, sulfhydryl, nitro, hydroxy and other like groups. Hydrophobicity can be conferred by the inclusion of apolar groups that include, but are not limited to, long chain saturated and unsaturated aliphatic hydrocarbon groups and such groups substituted by one or more aromatic, cycloaliphatic or heterocyclic group (s). Examples of amphipathic compounds include, but are not limited to, phospholipids, aminolipids and sphingolipids. Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine or dilinoleoylphosphatidylcholine. Other compounds lacking in phosphorus, such as sphingolipid, glycosphingolipid families, diacylglycerols and β-acyloxyacids, are also within the group designated as amphipathic lipids. Additionally, the amphipathic lipid described above can be mixed with other lipids including triglycerides and sterols.

The term "neutral lipid" refers to any of a number of lipid species that exist either in an uncharged or neutral zwitterionic form at a selected pH. At physiological pH, such lipids include, for example, diacylphosphatidylcholine, diacylphosphatidylethanolamine, ceramide, sphingomyelin, cephalin, cholesterol, cerebrosides and diacylglycerols.

The term "hydrophopic lipid" refers to compounds having apolar groups that include, but are not limited to, long chain saturated and unsaturated aliphatic hydrocarbon groups and such groups optionally substituted by one or more aromatic, cycloaliphatic or heterocyclic group(s). Suitable examples include, but are not limited to, diacylglycerol, dialkylglycerol, N-N-dialkylamino, 1,2-diacyloxy-3-aminopropane and 1,2-dialkyl-3-aminopropane.

The term "diacylglycerolyl" denotes 2-fatty acyl chains, $R^1$ and $R^2$ having independently between 2 and 30 carbons bonded to the 1- and 2-position of glycerol by ester linkages. The acyl groups can be saturated or have varying degrees of unsaturation. Diacylglycerol groups have the following general formula:

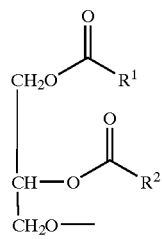

The term "dialkylglycerolyl" denotes two $C_1$–$C_{30}$ alkyl chains bonded to the 1- and 2-position of glycerol by ether linkages. Dialkylglycerol groups have the following general formula:

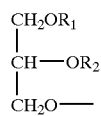

The term "N-N-dialkylamino" denotes

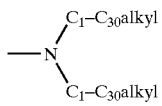

The term "1,2-diacyloxy-3-aminopropane" denotes 2-fatty acyl chains $C_1$–$C_{30}$ bonded to the 1- and 2-position of propane by an ester linkage. The acyl groups can be saturated or have varying degrees of unsaturation. The 3-position of the propane molecule has a —NH— group attached. 1,2-diacyloxy-3-aminopropanes have the following general formula:

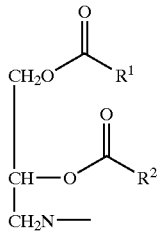

The term "1,2-dialkyl-3-aminopropane" denotes 2-alkyl chains ($C_1$–$C_{30}$) bonded to the 1- and 2-position of propane by an ether linkage. The 3-position of the propane molecule has a —NH— group attached. 1,2-dialkyl-3-aminopropanes have the following general formula:

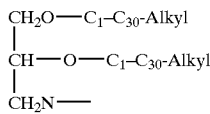

The term "non-cationic lipid" refers to any neutral lipid as described above as well as anionic lipids. Examples of anionic lipids include, but are not limited to, phosphatidylglycerol, cardiolipin, diacylphosphatidylserine, diacylphosphatidic acid, N-dodecanoyl phosphatidylethanolamines, N-succinyl phosphatidylethanolamines, N-glutarylphosphatidylethanolamines, lysophosphatidylglycerols, and other anionic modifying groups joined to neutral lipids.

The term "cationic lipid" refers to any of a number of lipid species that carry a net positive charge at a selected pH, such as physiological pH. Such lipids include, but are not limited to, N,N-dioleyl-N,N-dimethylammonium chloride ("DODAC"); N-(2,3-dioleyloxy)propyl)-N,N,N-trimethylammonium chloride ("DOTMA"); N,N-distearyl-N,N-dimethylammonium bromide ("DDAB"); N-(2,3-dioleoyloxy)propyl)-N,N,N-trimethylammonium chloride ("DOTAP"); 3-(N-(N',N'-dimethylaminoethane)carbamoyl) cholesterol ("DC-Chol") and N-(1,2-dimyristyloxyprop-3-yl)-N,N-dimethyl-N-hydroxyethyl ammonium bromide ("DMRIE"). Additionally, a number of commercial preparations of cationic lipids are available which can be used in the present invention. These include, for example, LIPOFECTIN® (commercially available cationic liposomes comprising DOTMA and 1,2-dioleoyl-sn-3-phosphoethanolamine ("DOPE"), from GIBCO/BRL, Grand Island, N.Y., USA); LIPOFECTAMINE® (commercially available cationic liposomes comprising N-(1-(2,3-dioleyloxy)propyl)-N-(2-(sperminecarboxamido) ethyl)N,N-dimethylammonium trifluoroacetate ("DOSPA") and ("DOPE"), from GIBCO/BRL); and TRANSFECTAM® (commercially available cationic lipids comprising dioctadecylamidoglycyl carboxyspermine ("DOGS") in ethanol from Promega Corp., Madison, Wis., USA). The following lipids are cationic and have a positive charge at below physiological pH: DODAP, DODMA, DMDMA and the like.

The term "fusogenic" refers to the ability of a liposome or other drug delivery system to fuse with membranes of a cell. The membranes can be either the plasma membrane or membranes surrounding organelles, e.g., endosome, nucleus, etc. Fusogenesis is the fusion of a liposome to such a membrane.

The term "dendrimer" includes reference to branched polymers that possess multiple generations. In dendrimers, each generation creates multiple branch points.

The term "ligand" includes any molecule, compound or device with a reactive functional group and includes lipids, amphipathic lipids, carrier compounds, bioaffinity compounds, biomaterials, biopolymers, biomedical devices, analytically detectable compounds, therapeutically active compounds, enzymes, peptides, proteins, antibodies, immune stimulators, radiolabels, fluorogens, biotin, drugs, haptens, DNA, RNA, polysaccharides, liposomes, virosomes, micelles, immunoglobulins, functional groups, targeting agents, or toxins. The foregoing list is illustrative and not intended to be exhaustive.

The term "ATTA" or "polyamide" refers to, but is not limited to, compounds disclosed in U.S. patent application Ser. No. 09/218,988, filed Dec. 22, 1998. These compounds include a compound having the formula

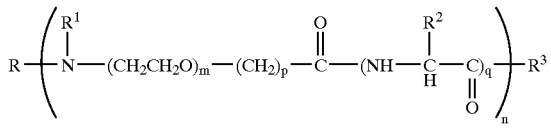

wherein: R is a member selected from the group consisting of hydrogen, alkyl and acyl; $R^1$ is a member selected from the group consisting of hydrogen and alkyl; or optionally, R and $R^1$ and the nitrogen to which they are bound form an azido moiety; $R^2$ is a member of the group selected from hydrogen, optionally substituted alkyl, optionally substituted aryl and a side chain of an amino acid; $R^3$ is a member selected from the group consisting of hydrogen, halogen, hydroxy, alkoxy, mercapto, hydrazino, amino and $NR^4R^5$, wherein $R^4$ and $R^5$ are independently hydrogen or alkyl; n is 4 to 80; m is 2 to 6; p is 1 to 4; and q is 0 or 1. It will be apparent to those of skill in the art that other polyamides can be used in the compounds of the present invention.

As used herein, the term "alkyl" denotes branched or unbranched hydrocarbon chains, such as, methyl, ethyl, n-propyl, iso-propyl, n-butyl, sec-butyl, iso-butyl, tertbutyl, octa-decyl and 2-methylpentyl. These groups can be optionally substituted with one or more functional groups which are attached commonly to such chains, such as, hydroxyl, bromo, fluoro, chloro, iodo, mercapto or thio, cyano, alkylthio, heterocyclyl, aryl, heteroaryl, carboxyl, carbalkoyl, alkyl, alkenyl, nitro, amino, alkoxyl, amido, and the like to form alkyl groups such as trifluoromethyl, 3-hydroxyhexyl, 2-carboxypropyl, 2-fluoroethyl, carboxymethyl, cyanobutyl and the like.

The term "alkylene" refers to a divalent alkyl as defined above, such as methylene (—$CH_2$—), propylene (—$CH_2CH_2CH_2$—), chloroethylene (—$CHClCH_2$—), 2-thiobutene (—$CH_2CH(SH)CH_2CH_2$—), 1-bromo-3-hydroxyl-4-methylpentene (—$CHBrCH_2CH(OH)CH(CH_3)CH_2$—), and the like.

The term "alkenyl" denotes branched or unbranched hydrocarbon chains containing one or more carbon-carbon double bonds.

The term "alkynyl" refers to branched or unbranched hydrocarbon chains containing one or more carbon-carbon triple bonds.

The term "aryl" denotes a chain of carbon atoms which form at least one aromatic ring having preferably between about 6–14 carbon atoms, such as phenyl, naphthyl, indenyl, and the like, and which may be substituted with one or more functional groups which are attached commonly to such chains, such as hydroxyl, bromo, fluoro, chloro, iodo, mercapto or thio, cyano, cyanoamido, alkylthio, heterocycle, aryl, heteroaryl, carboxyl, carbalkoyl, alkyl, alkenyl, nitro, amino, alkoxyl, amido, and the like to form aryl groups such as biphenyl, iodobiphenyl, methoxybiphenyl, anthryl, bromophenyl, iodophenyl, chlorophenyl, hydroxyphenyl, methoxyphenyl, formylphenyl, acetylphenyl, trifluoromethylthiophenyl, trifluoromethoxyphenyl, alkylthiophenyl, trialkylammoniumphenyl, amidophenyl, thiazolylphenyl, oxazolylphenyl, imidazolylphenyl, imidazolylmethylphenyl, and the like.

The term "acyl" denotes the —C(O)R group, wherein R is alkyl or aryl as defined above, such as formyl, acetyl, propionyl, or butyryl.

The term "alkoxy" denotes —OR—, wherein R is alkyl.

The term "amido" denotes an amide linkage: —C(O)NR— (wherein R is hydrogen or alkyl).

The term "amino" denotes an amine linkage: —NR—, wherein R is hydrogen or alkyl or a terminal $NH_2$.

The term "carboxyl" denotes the group —C(O)O—, and the term "carbonyl" denotes the group —C(O)—.

The term "carbonate" indicates the group —OC(O)O—.

The term "carbamate" denotes the group —NHC(O)O—, and the term "urea" denotes the group —NHC(O)NH—.

The term "phosphoro" denotes the group —OP(O)(OH)O—.

The term "basic amino acid" refers to naturally-occurring amino acids as well as synthetic amino acids and/or or amino acid mimetics having a net positive charge at a selected pH, such as physiological pH. This group includes, but is not limited to, lysine, arginine, asparagine, glutamine, histidine and the like.

The term "phosphorylethanolamino" denotes the group —OP(O)(OH)$OCH_2CH_2$NH—.

The term "phosphorylethanolamido" denotes the group —OP(O)(OH)$OCH_2CH_2$NHC(O)—.

The term "phospho" denotes a pentavalent phosphorous moiety —P(O)(OH)O—.

The term "phosphoethanolamino" denotes the group —P(O)(OH)$OCH_2CH_2$NH—.

The term "phosphoethanolamido" denotes the group —P(O)(OH)$OCH_2CH_2$NHC(O)—.

The term "ethylene oxide unit" denotes the group —$OCH_2CH_2$—.

The term "CPL" refers to a cationic-polymer-lipid e.g., cationic-PEG-lipid. Preferred CPLs are compounds of Formulae I and II.

The term "d-DSPE-CPL-M" is encompassed by the term "CPL1" which refers to a DSPE-CPL having one positive charge. The "d-" in d-DSPE-CPL-M indicates hat the CPL contains a fluorescent dansyl group. It will be apparent to those of skill in the art that a CPL can be synthesized without the dansyl moiety, and thus the term "DSPE-CPL-M" is encompassed by in the term "CPL1" as defined above.

The term "d-DSPE-CPL-D" is encompassed by the term "CPL2" which refers to DSPE-CPL having two positive charges.

The term "d-DSPE-CPL-T1" is encompassed by the term "CPL3" which refers to DSPE-CPL having three positive charges.

The term "d-DSPE-CPL-Q1" is encompassed by the term "CPL4a" which refers to DSPE-CPL having four positive charges.

The term "d-DSPE-CPL-Q5," or, alternatively, DSPE-PEGQuad5, or, alternatively, DSPE-CPL-4, are all encompassed by the term "CPL4 (or CPL4b)" which refer to a DSPE-CPL having four positive charges. By modifying the headgroup region, CPLs were synthesized which contained 1 (mono, or M), 2 (di, or D), 3 (tri, or T), and 4 (quad, or Q) positive charges. Various Quad CPLs were synthesized, hence these are numbered Q1 through Q5.

The abbreviations "HBS" refers to Hepes-buffered saline, "Rho-PE" refers to rhodamine-phosphatidylethanolamine, and "LUVs" refers to "large unilamellar vesicles."

BRIEF DESCRIPTION OF THE DRAWINGS

FIGS. 8A–8C illustrate the preparation of CPL-LUVs by detergent dialysis. Lipids were codissolved in chloroform at the indicated ratios, following which the solvent was removed by nitrogen gas and high vacuum. The lipid mixture was dissolved in detergent/buffer (OGP in HBS) and dialysed against HBS for 2–3 days. The LUVs, which formed during dialysis, were then fractionated as shown on Sepharose CL-4B. Panel A: Fractionation of DOPE/DODAC/CPL4[3.4K]/PEGCerC20/Rho-PE (79.5/6/4/10/0.5); Panel B: Fractionation of DOPE/DODAC/CPL4[1K]/PEGCerC20/Rho-PE (79.5/6/4/10/0.5); and Panel C: Fractionation of DOPE/DODAC/CPL4[3.4K]/PEGCerC20/Rho-PE (71.5/6/12/10/0.5).

FIG. 19B shows the column profile for Fraction #9 from FIG. 19A.

FIGS. 23A–23C tabulate CPL insertion results.

FIGS. 24A–24C also tabulate CPL insertion results.

FIGS. 29A–29B illustrate a synthetic embodiment to generate compounds of the present invention.

DETAILED DESCRIPTION OF THE INVENTION AND PREFERRED EMBODIMENTS

A. Compounds and Synthesis

Figure 1:
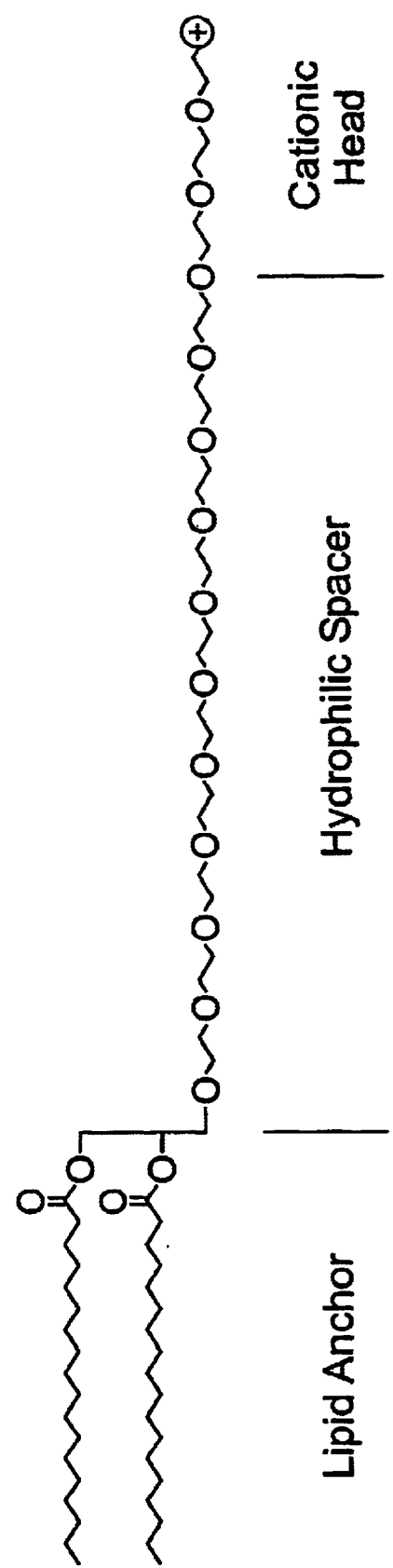
FIG. 1 illustrates a structural design of a cationic-polymer lipid (CPL) conjugate.

In certain aspects, the present invention provides cationic-polymer-lipid conjugates (CPLs), such as distal cationic-poly(ethylene glycol)-lipid conjugates that can be incorporated into conventional and stealth liposomes for enhancing, inter alia, cellular uptake. The CPLs of the present invention have the following architectural features: (1) a lipid anchor, such as a hydrophobic lipid, for incorporating the CPLs into the lipid bilayer; (2) a hydrophilic spacer, such as a polyethylene glycol, for linking the lipid anchor to a cationic head group; and (3) a polycationic moiety, such as a naturally occurring amino acid, to produce a protonizable cationic head group. As such, the present invention provides a compound of Formula I:

A—W—Y     I wherein A, W and Y are as previously defined.

With reference to Formula I, "A" is a lipid moiety such as an amphipathic lipid, a neutral lipid or a hydrophobic lipid that acts as a lipid anchor. Suitable lipid examples include vesicle-forming lipids or vesicle adopting lipids and include, but are not limited to, diacylglycerolyls, dialkylglycerolyls, N-N-dialkylaminos, 1,2-diacyloxy-3-aminopropanes and 1,2-dialkyl-3-aminopropanes.

"W" is a polymer or an oligomer, such as a hydrophilic polymer or oligomer. Preferably, the hydrophilic polymer is a biocompatable polymer that is non-immunogenic or possesses low inherent immunogenicity. Alternatively, the hydrophilic polymer can be weakly antigenic if used with appropriate adjuvants. Suitable non-immunogenic polymers include, but are not limited to, PEG, polyamides, polylactic acid, polyglycolic acid, polylactic acid/polyglycolic acid copolymers and combinations thereof. In a preferred embodiment, the polymer has a molecular weight of about 250 to about 7000 daltons.

"Y" is a polycationic moiety. The term polycationic moiety refers to a compound, derivative, or functional group having a positive charge, preferably at least 2 positive charges at a selected pH, preferably physiological pH. Suitable polycationic moieties include basic amino acids and their derivatives such as arginine, asparagine, glutamine, lysine and histidine; spermine; spermidine; cationic dendrimers; polyamines; polyamine sugars; and amino polysaccharides. The polycationic moieties can be linear, such as linear tetralysine, branched or dendrimeric in structure. Polycationic moieties have between about 2 to about 15 positive charges, preferably between about 2 to about 12 positive charges, and more preferably between about 2 to about 8 positive charges at selected pH values. The selection of which polycationic moiety to employ may be determined by the type of liposome application which is desired.

The charges on the polycationic moieties can be either distributed around the entire liposome moiety, or alternatively, they can be a discrete concentration of charge density in one particular area of the liposome moiety e.g., a charge spike. If the charge density is distributed on the liposome, the charge density can be equally distributed or unequally distributed. All variations of charge distribution of the polycationic moiety are encompassed by the present invention.

The lipid "A", and the non-immunogenic polymer "W", can be attached by various methods and preferably, by covalent attachment. Methods known to those of skill in the art can be used for the covalent attachment of "A" and "W". Suitable linkages include, but are not limited to, amide, amine, carboxyl, carbonate, carbamate, ester and hydrazone linkages. It will be apparent to those skilled in the art that "A" and "W" must have complementary functional groups to effectuate the linkage. The reaction of these two groups, one on the lipid and the other on the polymer, will provide the desired linkage. For example, when the lipid is a diacylglycerol and the terminal hydroxyl is activated, for instance with NHS and DCC, to form an active ester, and is then reacted with a polymer which contains an amino group, such as with a polyamide (see, U.S. patent application Ser. No. 09/218,988, filed Dec. 22, 1998), an amide bond will form between the two groups.

In certain embodiments, "W" is bound, preferably covalently bound, to "Y". As with "A" and "W", a covalent attachment of "W" to "Y" can be generated by complementary reactivity of functional groups, one on the polymer and the other on the polycationic moiety. For example, an amine functional group on "W" can be reacted with an activated carboxyl group, such as an acyl chloride or NHS ester, to form an amide. By suitable choice of reactive groups, the desired coupling can be obtained. Other activated carboxyl groups include, but are not limited to, a carboxylic acid, a carboxylate ester, a carboxylic acid halide and other activated forms of carboxylic acids, such as a reactive anhydride. Reactive acid halides include for example, acid chlorides, acid bromides, and acid fluorides.

In certain instances, the polycationic moiety can have a ligand attached, such as a targeting ligand. Preferably, after the ligand is attached, the cationic moiety maintains a positive charge. In certain instances, the ligand that is attached has a positive charge. Suitable ligands include, but are not limited to, a compound or device with a reactive functional group and includes lipids, amphipathic lipids, carrier compounds, bioaffinity compounds, biomaterials, biopolymers, biomedical devices, analytically detectable compounds, therapeutically active compounds, enzymes, peptides, proteins, antibodies, immune stimulators, radiolabels, fluorogens, biotin, drugs, haptens, DNA, RNA, polysaccharides, liposomes, virosomes, micelles, immunoglobulins, functional groups, other targeting moieties, or toxins.

In certain preferred embodiments, other moieties are incorporated into the compounds of Formula I to form the compounds of Formula II:

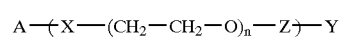

II

In Formula II, "A" is a lipid moiety such as, an amphipathic lipid, a neutral lipid or a hydrophobic lipid moiety. Suitable lipid examples include, but are not limited to, diacylglycerolyl, dialkylglycerolyl, N-N-dialkylamino, 1,2-diacyloxy-3-aminopropane and 1,2-dialkyl-3-aminopropane.

In Formula II, "X" is a single bond or a functional group that covalently attaches the lipid to at least one ethylene oxide unit. Suitable functional groups include, but are not limited to, phosphatidylethanolamino, phosphatidylethanolamido, phosphoro, phospho, phosphoethanolamino, phosphoethanolamido, carbonyl, carbamate, carboxyl, carbonate, amido, thioamido, oxygen, NR wherein R is a hydrogen or alkyl group and sulfur. In certain instances, the lipid "A" is directly attached to the ethylene oxide unit by a single bond. The number of ethylene oxide units can range from about 1 to about 160 and preferably from about 6 to about 50.

In Formula II, "Z" is a single bound or a functional group that covalently attaches the ethylene oxide unit to the polycationic moiety. Suitable functional groups include, but are not limited to, phosphor phosphoethanolamino, phosphoethanolamido, carbonyl, carbamate, carboxyl, amido, thioamido, NR wherein R is a member selected from the group consisting of hydrogen atom or alkyl group. In certain embodiments, the terminal ethylene oxide unit is directly attached to the polycationic moiety.

In Formula II, "Y" is a polycationic moiety as described above in connection with Formula I. In Formula II, the index "n" is an integer ranging in value from about 6 to about 160.

Figure 2A:
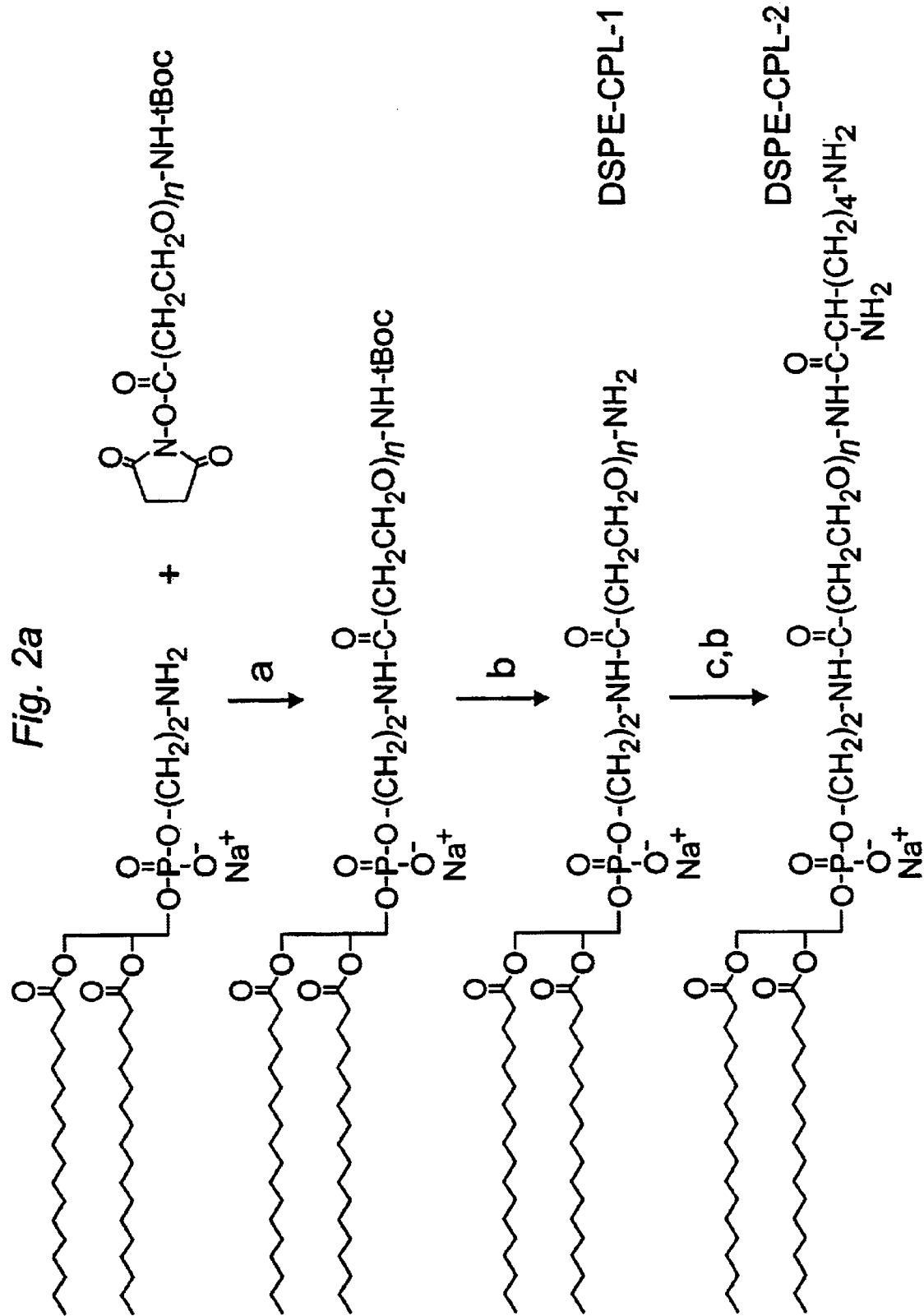
FIGS. 2A and 2B illustrate a synthetic scheme for the preparation of cationic-PEG-lipid conjugates having varying amount of charged head groups (a.) $Et_3N/CHCl_3$; (b.) TFA/$CHCl_3$; c. $Et_3N/CHCl_3$ Nα, Nε-di-t-Boc-L-Lysine N-hydroxysuccinide ester.
Figure 2B:
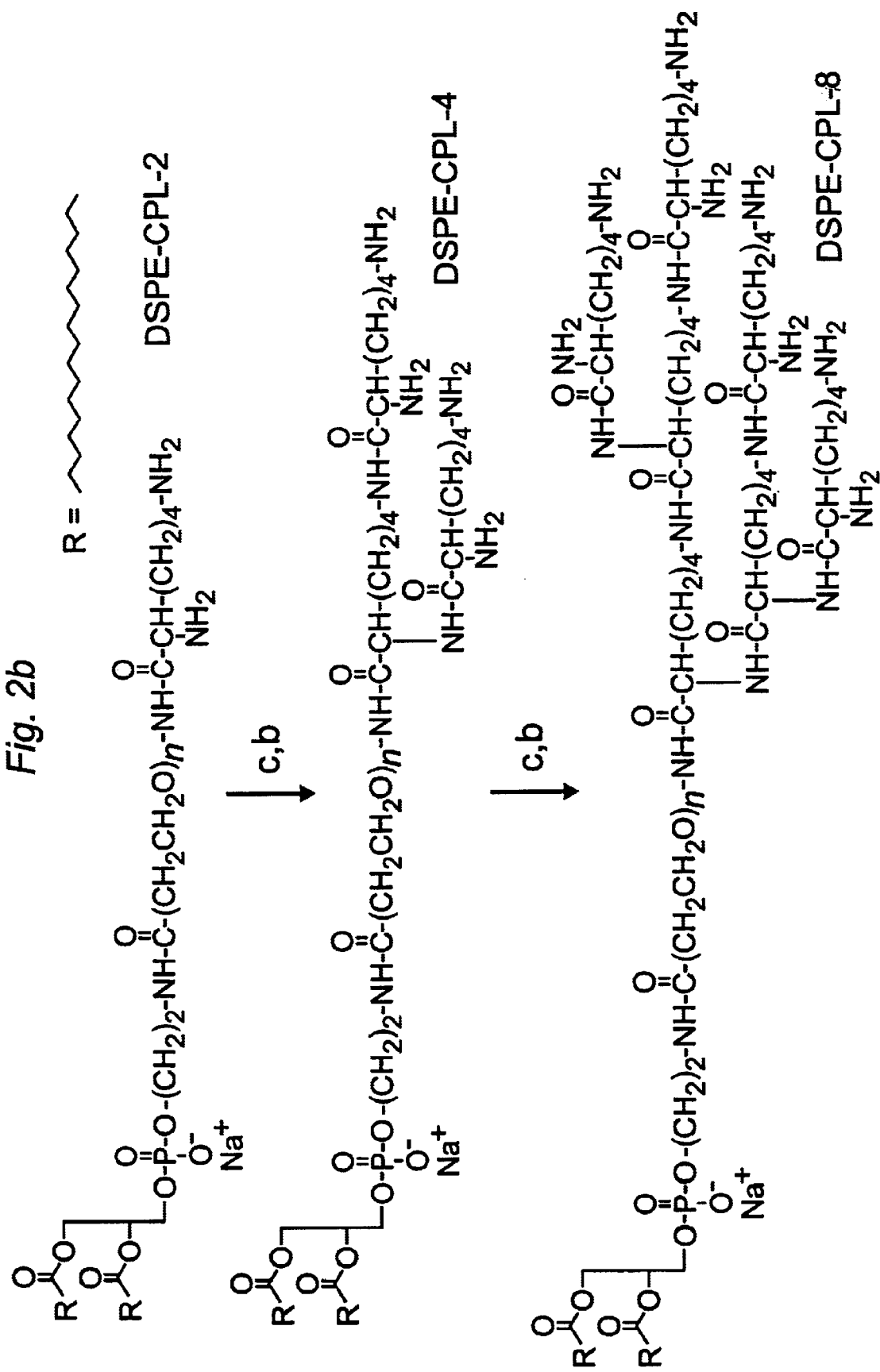
Figure 3:
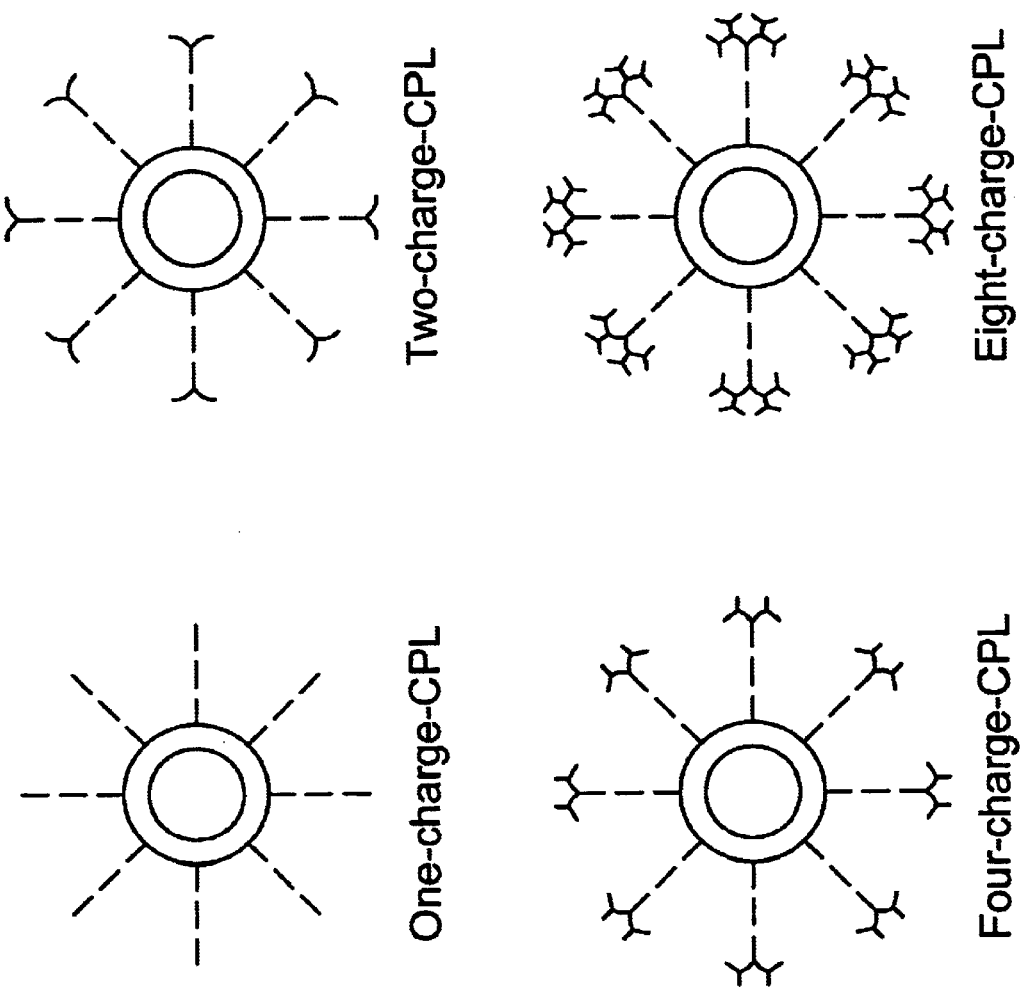
FIG. 3 illustrates a CPL incorporated liposome. The large unilamellar vesicles (LUV) have incorporated different examples of CPLs (CPL1, CPL2, CPL4, and CPL8, respectively).
Figure 4:
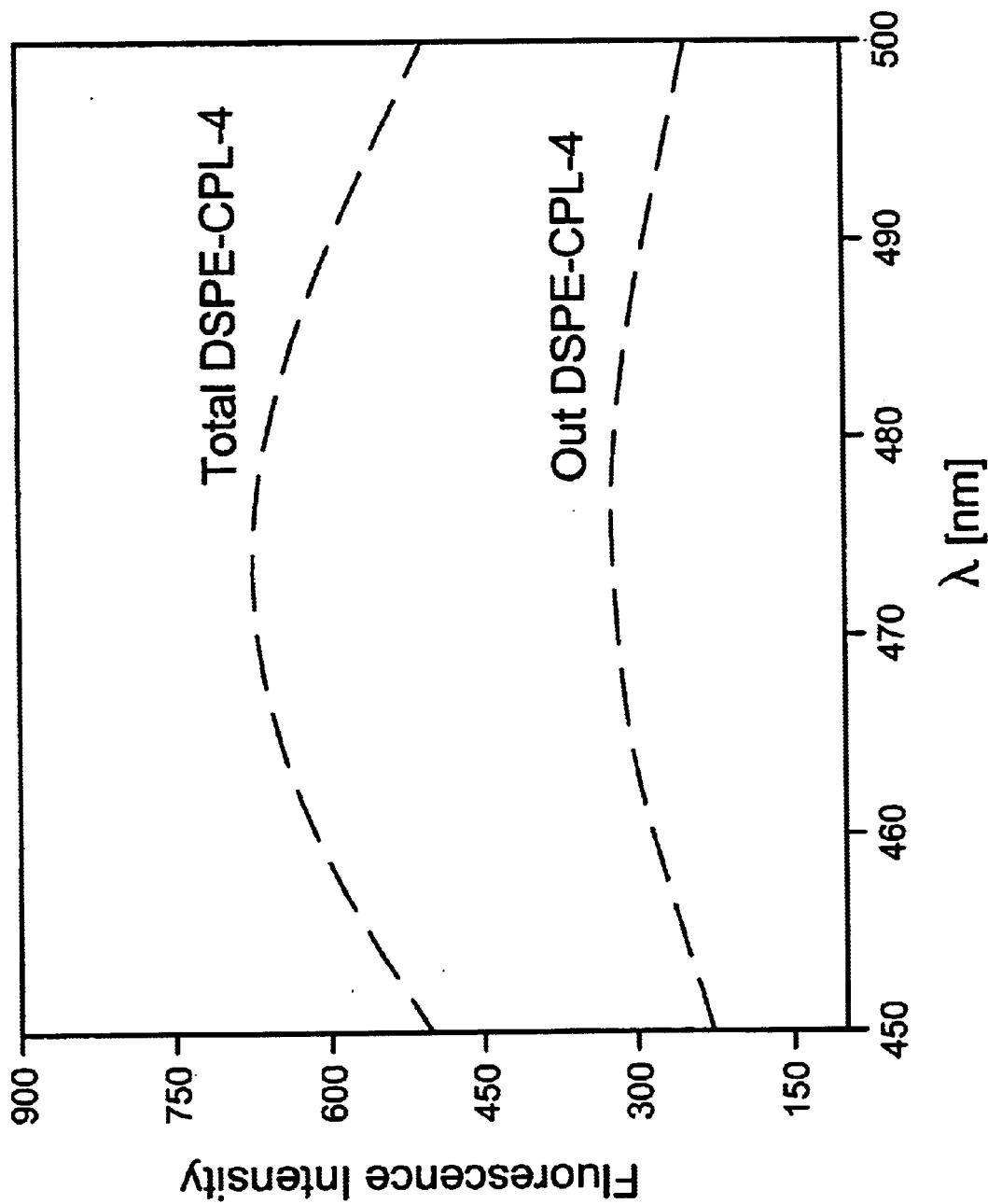
FIG. 4 illustrates a distribution of DSPE-CPL-4 between the inner/outer leaflets of a liposomal membrane. CPL-4-LUVs (DSPC/Chol/DSPE-CPL-4, 55:40:5 mole %) were prepared by extrusion method as described herein. The distribution of outer leaflet CPLs was quantified by a fluorescamine assay. For the outer leaflet CPLs, the following assay was used. An appropriate amount of CPL-4-LUVs was diluted with 1M Borate buffer (pH 8.5) and cooled in ice-water. 20 µl of 10% Triton X-100 was added to the above sample solution to solubilize the membrane, and then an additional 20 µl of a cooled fluorescamine ethanol solution (10 mg/ml) was added and then measured.

In an illustrative embodiment, compounds of Formula II can be synthesized using a generalized procedure as outlined in FIG. 2. FIG. 2 illustrates one particular embodiment of the present invention and thus, is merely an example that should not limit the scope of the claims herein. Clearly, one of ordinary skill in the art will recognize many other variations, alternatives, and modifications that can be made to the reaction scheme illustrated in FIG. 2. With reference to FIG. 2, a solution of a lipid, such as DSPE, and a base, such as triethylamine in a chloroform solution is added to (t-Boc- NH-PEG$_{3400}$-CO$_2$NHS), and the solution is stirred at ambient temperature. The solution is then concentrated under a nitrogen stream to dryness. The residue is then purified by repeated precipitation of the chloroform mixture solution with diethyl ether until disappearance of the lipid using chromatography. The purified CPL conjugate is dissolved in a solvent, followed by addition of TFA, and the solution is stirred at room temperature. The solution can again be concentrated under a nitrogen stream. The residue is then purified by repeated precipitation of the mixture with diethyl ether to offer a lipid-PEG-NH$_2$, such as a DSPE-PEG-NH$_2$ or, alternatively, DSPE-CPL-1 with one protonizable cationic head group. The ratio of the phosphoryl-lipid anchor and the distal primary amine can then be measured by phosphate and flourescamine assays as described herein.

In this illustrative embodiment, the number of protonizable amino groups can be increased to create a polycationic moiety. By incrementally adding stoichiometric amounts of, for example, a Nα,Nε-di-t-Boc-L-Lysine N-hydroxysuccinide ester, the polycationic moiety can be increase from about 2 to about 16 positive charges. As describe previously, the positive charges can be incorporated using any number of suitable polycationic moieties such as lysine, arginine, asparagine, glutamine, histidine, polyamines and derivatives or combinations thereof. Using the synthesis methods of the present invention, the number of cationic groups, such as amino groups, can be readily controlled during the CPL synthesis.

B. Lipid-based Drug Formulations

In certain aspects, the present invention provides a lipid-based drug formulation comprising:

(a) a compound having the general structure of Formula I:

   I wherein A, W and Y are as previously defined; (b) a bioactive agent; and optionally, (c) a second lipid. In preferred embodiments, the lipid-based drug formulation of the present invention comprises the second lipid, such as a PEG-lipid derivative.

In certain preferred embodiments, the lipid-based drug formulations of the present invention comprise (a) a compound of Formula II:

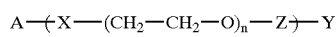   II wherein A, X, Z, Y and n have been previously defined; (b) a bioactive agent; and optionally, (c) a second lipid. In preferred embodiments, the lipid-based drug formulation of the present invention comprises the second lipid, such as a PEG-lipid derivative.

After the CPLs have been prepared, they can be utilized in a variety of ways including, for example, in lipid-based drug formulations. In this aspect, the lipid-based formulations can be in the form of a liposome, a micelle, a virosome, a lipid-nucleic acid particle, a nucleic acid aggregate and other forms which can incorporate or entrap one or more bioactive agents. In certain aspects, the lipid-based drug formulations of the present invention comprise a second lipid.

The compounds of Formulae I and II can be used in lipid-based formulations such as those described in for example, the following copending U.S. patent applications Ser. Nos. 08/454,641, 08/485,458, 08/660,025, 08/484,282, 60/055,094, 08/856,374, 60/053,813 and 60/063,473, entitled "Methods for Encapsulating Nucleic Acids in Lipid Bilayers," filed on Oct. 10, 1997 and bearing U.S. Pat. No. 5,703,055, U.S. patent application Ser. No. 09/218,988, filed Dec. 22, 1998, the teachings all of which are incorporated herein by reference in their entirety for all purposes. This specification sets out a variety of liposome types and a variety of methods for incorporating CPLs into liposomes, all of which are examples of the broad methods and compositions claimed herein.

The lipid components and CPLs used in forming the various lipid-based drug formulations will depend, in part, on the type of delivery system employed. For instance, if a liposome is employed, the lipids used in the CPL will generally be selected from a variety of vesicle-forming or vesicle-adopting lipids, typically including phospholipids and sterols, such as phosphatidylenthanolamine (PE), phosphatidylserine (PS), phosphatidylinositol (PI), phosphatidylglycerol (PG), phosphatidic acid (PA), which have been suitably functionalized, and the like. In contrast, if a micelle is employed, the lipids used in the CPL will generally be selected from sterylamines, alkylamines, C$_8$–C$_{22}$ alkanoic acids, lysophospholipids, detergents and the like. It will be readily apparent to those of skill in the art that the acyl chains can be varied in length and can be saturated or possess varying degrees of unsaturation. The more saturated the acyl chains the more rigid the membrane. Higher degrees of unsaturation impart more fluidity into the vesicle's membrane. Similarly, the other lipid components (e.g., lipids, cationic lipids, neutral lipids, non-cationic lipids, etc.) making up the drug delivery systems of the present invention will vary depending on the drug delivery system employed. Suitable lipids for the various drug delivery systems will be readily apparent to those of skill in the art.

When the lipid-based drug formulations are used to deliver therapeutic genes or oligonucleotides intended to induce or to block production of some protein within the cell, cationic lipids can be included in the formulation, e.g., liposome, micelle, lipid-nucleic acid particle, etc. Nucleic acid is negatively charged and can be combined with a positively charged entity to form a lipid complex suitable for formulation and cellular delivery.

As used in this specification, "cationic lipid" generally refers to a lipid with a cationic head group situated at or near the liposome membrane (when incorporated in a liposome). CPLs are distinguished from cationic lipids by the polymer "W" which in certain instances, has the effect of placing the cationic charge at a significant distance from the membrane.

Examples of suitable cationic lipids include, but are not limited to, the following: DC-Chol, (see, Gao, et al., *Biochem. Biophys. Res. Comm.*, 179:280–285 (1991); DDAB; DMRIE; DODAC (see, U.S. patent application Ser. No. 08/316,399, filed Sep. 30, 1994, which is incorporated herein by reference); DOGS; DOSPA; DOTAP; and DOTMA. In a presently preferred embodiment, N,N-dioleoyl-N,N-dimethylammonium chloride is used in combination with a phosphatidylethanolamine.

In addition, other cationic lipids useful in producing lipid-based carriers for gene and oligonucleotide delivery are LIPOFECTIN (U.S. Pat. Nos. 4,897,355; 4,946,787; and 5,208,036 issued to Eppstein, et al.) and LIPOFECTACE (U.S. Pat. No. 5,279,883 issued to Rose). Both agents, as well as other transfecting cationic lipids, are available from Life Technologies, Inc. in Gaithersburg, Md.

Figure 17A:
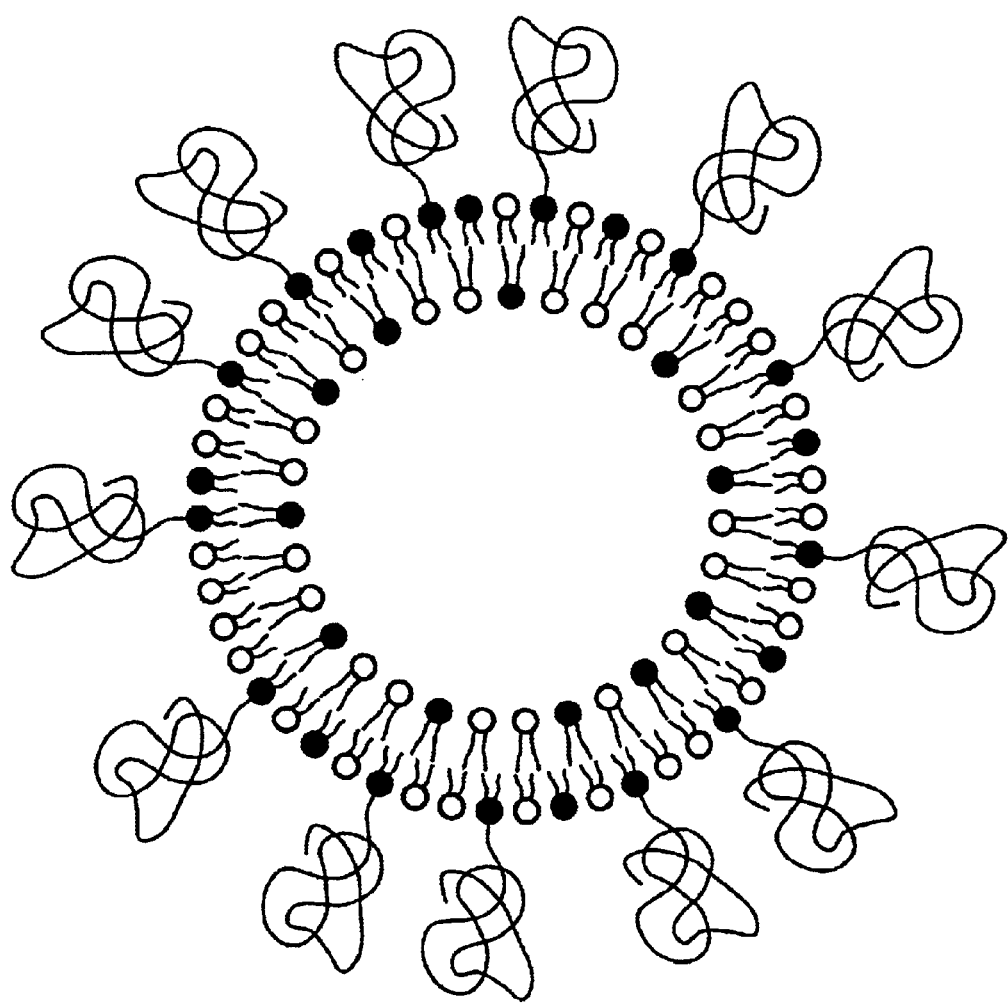
FIG. 17A illustrates a model for DOPE/DODAC/PEG-Cer-C20 LUVs, i.e., a standard liposome containing a PEG-lipid (or "stealth" lipid)
Figure 17B:
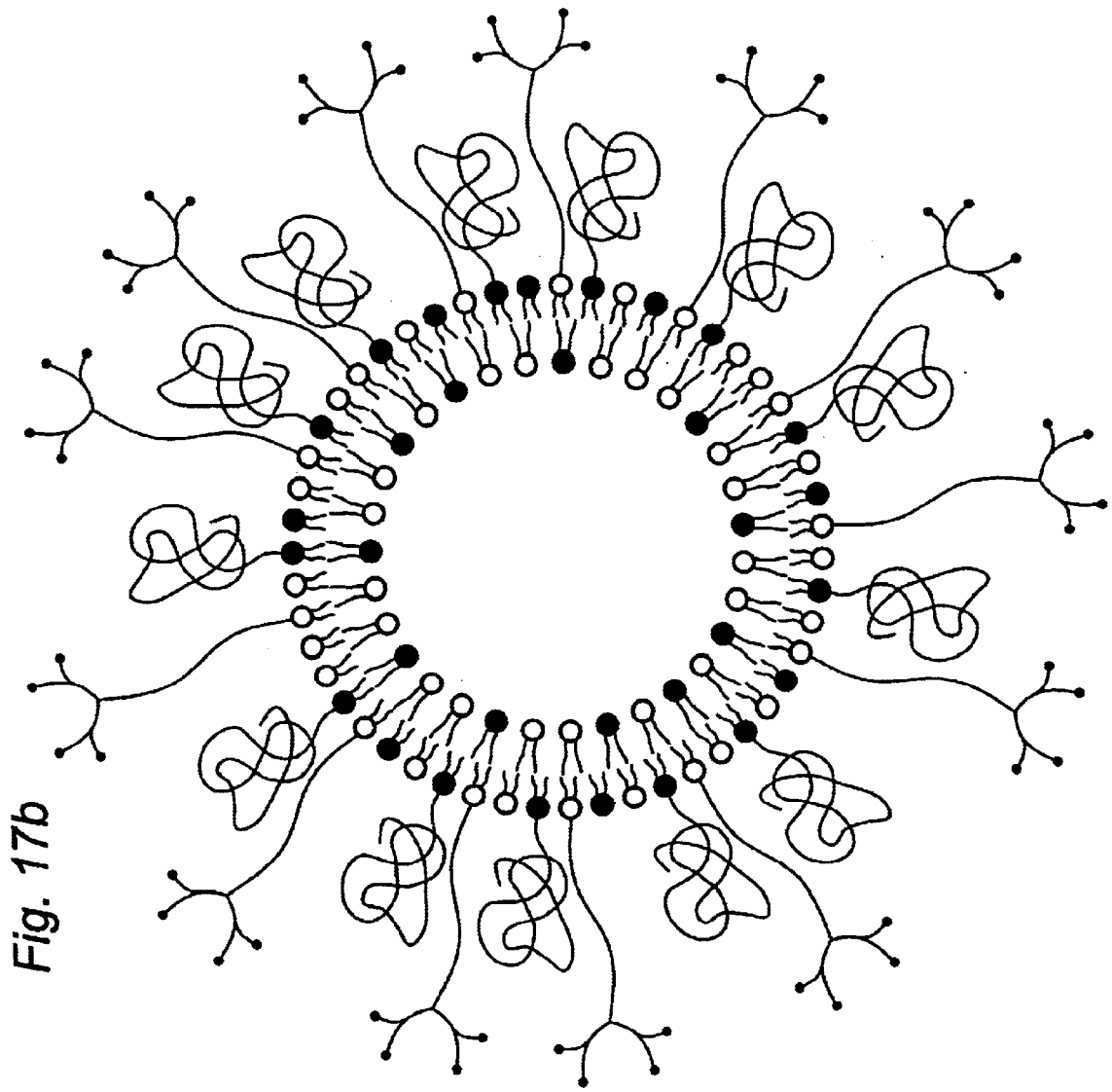
FIG. 17B illustrates the same LUVs with $CPL_4$ (i.e. long chain) inserted. "Long chain" refers to the polymer W being the same length or greater length than the polymer component of the PEG-lipid. Thus, the charged group of the CPL1 is immediately exposed to the outside environment.
Figure 17C:
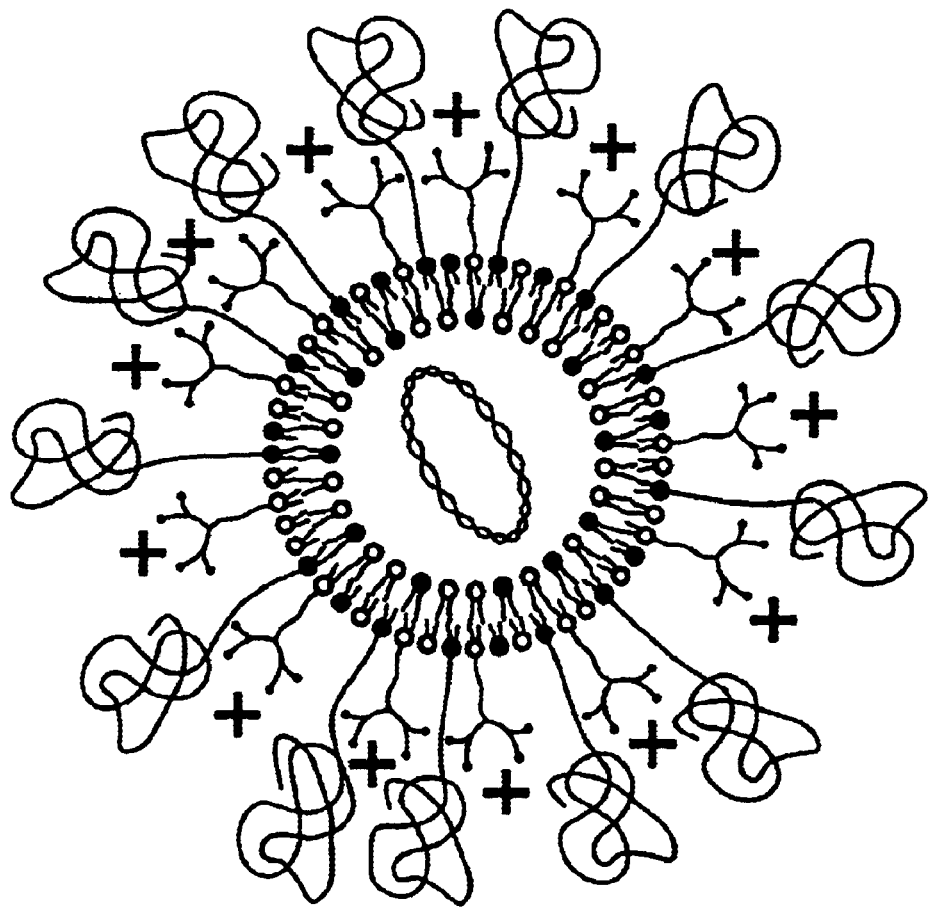
FIG. 17C illustrates the same LUVs with $CPL_4$ with a short chain inserted. A "short chain" CPL, wherein polymer W is shorter than the corresponding polymer of the PEG-lipid.

In one preferred embodiment, the CPL-liposomes of the present invention are optimized for systemic delivery applications. In certain applications, the polymer length in the CPL is shorter than the normal neutral PEG chains (M.W. 2000–5000 Daltons) used for stealth liposomes. In this instance, the shorter polymer in the CPL is about 250 to about 3000 Daltons and more preferably, about 1000 to about 2000 Daltons. In this embodiment, the second lipid is for example, a PEG$_{3400}$-lipid and the compound of Formula I is, for example, A-PEG$_{1000}$-Y. (see, FIG. 17C).

Without being bound by any particular theory, when the shorter polymer is used, it is believed that the distal charge (s) of the CPL is hidden within the normal PEG exclusion barrier, thus allowing retention of long circulation lifetimes while at the same time, extending the positive charges away from the liposomal surface. This embodiment enhances interactions between liposomes and a target cell. The use of different sized polymers, such as PEG chains, in the CPLs and the neutral PEG-lipids used to modulate vesicle circulation and cellular uptake, allows for a new generation of stealth liposomes as drug carriers. It is believed that the optimized polymer length can vary with the specific conditions such as in vitro or in vivo applications, local or systemic administration, and different lipid formulations.

In another embodiment, the polymer length in the CPL has a larger MW than the normal neutral PEG chains used for stealth liposomes. In this instance, the second lipid is for example, a PEG$_{1000}$-lipid and the compound of Formula I has a formula of for example, A-PEG$_{3400}$-Y. (see, FIG. 17B).

In certain formulations and applications, the type of CPL i.e. the length of the polymer chain, and the amount of cationic charge per molecule, and the amount of such CPL in a formulation e.g., SPLP, can be optimized to obtain the best balancing of clearance properties. In certain instances, long chain CPLs and higher levels of such CPLs are to be preferred to increase transfection. In other instances, short chain CPLs incorporated in the formulations are optimized for longer circulation lifetimes in animals.

In one embodiment of the present invention, a fusogenic liposome or virosome is provided. It will be readily apparent to those of skill in the art that the CPLs of the present invention can advantageously be incorporated into various types of fusogenic liposomes and virosomes. Such fusogenic liposomes and virosomes can be designed to become fusogenic at the disease or target site. Those of skill in the art will readily appreciate that a number of variables can be used to control when the liposome or virosome becomes fusogenic. Such variables include, for example, the composition of the liposome or virosome, pH, temperature, enzymes, cofactors, ions, etc.

In one embodiment, the fusogenic liposome comprises: a lipid capable of adopting a non-lamellar phase, yet capable of assuming a bilayer structure in the presence of a bilayer-stabilizing component (such as a PEG-lipid derivative); and a bilayer-stabilizing component reversibly associated with the lipid to stabilize the lipid in a bilayer structure. Such fusogenic liposomes are advantageous because the rate at which they become fusogenic can be not only predetermined, but varied as required over a time scale of a few minutes to several tens of hours. It has been found, for example, that by controlling the composition and concentration of the bilayer-stabilizing component, one can control the rate at which the BSC exchanges out of the liposome in vivo and, in turn, the rate at which the liposome becomes fusogenic (see, U.S. Pat. No. 5,885,613). For instance, it has been found that by controlling the length of the lipid acyl chain(s), one can control the rate at which the BSC exchanges out of the liposome in vivo and, in turn, the rate at which the liposome becomes fusogenic. In particular, it has been discovered that shorter acyl chains (e.g., C-8) exchange out of the liposome more rapidly than longer acyl chains (e.g., C-20). Alternatively, by controlling the composition and concentration of the BSC, one can control the rate at which the BSC is degraded, i.e., broken down, by endogenous systems, e.g., endogenous enzymes in the serum, and, in turn, the rate at which the liposome becomes fusogenic.

The polymorphic behavior of lipids in organized assemblies can be explained qualitatively in terms of the dynamic molecular shape concept (see, Cullis, et al., in "Membrane Fusion" (Wilschut, J. and D. Hoekstra (eds.), Marcel Dekker, Inc., New York, (1991)). When the effective cross-sectional areas of the polar head group and the hydrophobic region buried within the membrane are similar then the lipids have a cylindrical shape and tend to adopt a bilayer conformation. Cone-shaped lipids which have polar head groups that are small relative to the hydrophobic component, such as unsaturated phosphatidylethanolamines, prefer non-bilayer phases such as inverted micelles or inverse hexagonal phase (H). Lipids with head groups that are large relative to their hydrophobic domain, such as lysophospholipids, have an inverted cone shape and tend to form micelles in aqueous solution. The phase preference of a mixed lipid system depends, therefore, on the contributions of all the components to the net dynamic molecular shape. As such, a combination of cone-shaped and inverted cone-shaped lipids can adopt a bilayer conformation under conditions where either lipid in isolation cannot (see, Madden and Cullis, *Biochim. Biophys. Acta*, 684:149–153 (1982)).

A more formalized model is based on the intrinsic curvature hypothesis (see, e.g., Kirk, et al., *Biochemistry*, 23:1093–1102 (1984)). This model explains phospholipid polymorphism in terms of two opposing forces. The natural tendency of a lipid monolayer to curl and adopt its intrinsic or equilibrium radius of curvature ($R_O$) which results in an elastically relaxed monolayer is opposed by the hydrocarbon packing constraints that result. Factors that decrease the intrinsic radius of curvature, such as increased volume occupied by the hydrocarbon chains when double bonds are introduced, tend to promote H phase formation. Conversely, an increase in the size of the headgroup increases $R_O$ and promotes bilayer formation or stabilization. Introduction of apolar lipids that can fill the voids between inverted lipid cylinders also promotes H phase formation (see, Gruner, et al., *Proc. Natl. Acad. Sci. USA*, 82:3665–3669 (1989); Sjoland, et al., *Biochemistry*, 28:1323–1329 (1989)).

As such, in one embodiment, the lipids which can be used to form the fusogenic liposomes of the present invention are those which adopt a non-lamellar phase under physiological conditions or under specific physiological conditions, e.g., in the presence of calcium ions, but which are capable of assuming a bilayer structure in the presence of a BSC. Such lipids include, but are not limited to, phosphatidylenthanolamines, ceramides, glycolipids, or mixtures thereof. Other lipids known to those of skill in the art to adopt a non-lamellar phase under physiological conditions can also be used. Moreover, it will be readily apparent to those of skill in the art that other lipids can be induced to adopt a non-lamellar phase by various non-physiological changes including, for example, changes in pH or ion concentration (e.g., in the presence of calcium ions) and, thus, they can also be used to form the fusogenic liposomes of the present invention. In a presently preferred embodiment, the fusogenic liposome is prepared from a phosphatidylethanolamine. The phosphatidylethanolamine can be saturated or unsaturated. In a presently preferred embodiment, the phosphatidylyethanolamine is unsaturated.

In an equally preferred embodiment, the fusogenic liposome is prepared from a mixture of a phosphatidylethanolamine (saturated or unsaturated) and a phosphatidylserine. In another equally preferred embodiment, the fusogenic liposome is prepared from a mixture of a phosphatidylethanolamine (saturated or unsaturated) and a cationic lipid.

In one embodiment, the lipid-based drug formulations of the present invention comprise a bilayer stabilizing component (BSC). Suitable BSCs include, but are not limited to, polyamide oligomers, peptides, proteins, detergents, lipid-derivatives, PEG-lipids such as PEG coupled to phosphatidylethanolamine, and PEG conjugated to ceramides (see, U.S. Pat. No. 5,885,613, which is incorporated herein by reference). Preferably, the bilayer stabilizing component is a PEG-lipid, or an ATTA-lipid. As discussed herein, in certain preferred instances, the PEG or the ATTA of the BSC has a greater molecular weight compared to the polymer "W" of the CPL. In other instances, the BSC has a smaller molecular weight compared to the "W" of the polymer. The present invention encompasses all such variations.

In accordance with the present invention, lipids adopting a non-lamellar phase under physiological conditions can be stabilized in a bilayer structure by BSCs which are either bilayer forming themselves, or which are of a complementary dynamic shape. The non-bilayer forming lipid is stabilized in the bilayer structure only when it is associated with, i.e., in the presence of, the BSC. In selecting an appropriate BSC, it is preferable that the BSC be capable of transferring out of the liposome, or of being chemically modified by endogenous systems such that, with time, it loses its ability to stabilize the lipid in a bilayer structure. Only when liposomal stability is lost or decreased can fusion of the liposome with the plasma membrane of the target cell occur. The BSC-lipid, therefore, is "reversibly associated" with the lipid and only when it is associated with the lipid is the lipid constrained to adopt the bilayer structure under conditions where it would otherwise adopt a non-lamellar phase. As such, the BSC-lipids of the present invention are capable of stabilizing the lipid in a bilayer structure, yet they are capable of exchanging out of the liposome, or of being chemically modified by endogenous systems so that, with time, they lose their ability to stabilize the lipid in a bilayer structure, thereby allowing the liposome to become fusogenic.

Typically, the CPL is present in the lipid-based formulation of the present invention at a concentration ranging from about 0.05 mole percent to about 50 mole percent. In a presently preferred embodiment, the CPL is present at a concentration ranging from 0.05 mole percent to about 25 mole percent. In an even more preferred embodiment, the CPL is present at a concentration ranging from 0.05 mole percent to about 15 mole percent. One of ordinary skill in the art will appreciate that the concentration of the CPL can be varied depending on the CPL employed and the rate at which the liposome is to become fusogenic.

In one embodiment of the present invention, the liposomes contain cholesterol. It has been determined that when cholesterol-free liposomes are used in vivo, they have a tendency to absorb cholesterol from the plasma lipoproteins and cell membranes. Cholesterol, if included, is generally present at a concentration ranging from 0.2 mole percent to about 50 mole percent and, more preferably, at a concentration ranging from about 35 mole percent to about 45 mole percent.

C. Preparation of CPL-liposomes

A variety of general methods for making CPL-containing liposomes (or "CPL-liposomes") are discussed herein.

Two general techniques include "post-insertion," that is, insertion of a CPL into for example, a pre-formed liposome vesicle, and "standard" techniques, wherein the CPL is included in the lipid mixture during for example, the liposome formation steps. The post-insertion technique results in liposomes having CPLs mainly in the external face of the liposome bilayer membrane, whereas standard techniques provide liposomes having CPLs on both internal and external faces.

In particular, "post-insertion" involves forming vesicles (by any method), and incubating the pre-formed vesicles in the presence of CPL under appropriate conditions (usually 2–3 hours at 60° C.). Between 60–80% of the CPL can be inserted into the external leaflet of the recipient vesicle, giving final concentrations up to 7 mol % (relative to total lipid). The method is especially useful for vesicles made from phospholipids (which can contain cholesterol) and also for vesicles containing PEG-lipids (such as PEG-Ceramide).

In an example of a "standard" technique, the CPL-LUVs of the present invention can be formed by extrusion. In this embodiment, all of the lipids including CPL, are co-dissolved in chloroform, which is then removed under nitrogen followed by high vacuum. The lipid mixture is hydrated in an appropriate buffer, and extruded through two polycarbonate filters with a pore size of 100 nm. The resulting vesicles contain CPL on both internal and external faces. In yet another standard technique, the formation of CPL-LUVs can be accomplished using a detergent dialysis or ethanol dialysis method, for example, as discussed in U.S. Pat. Nos. 5,976,567 and 5,981,501, both of which are incorporated herein by reference. The extrusion method and the detergent dialysis method are explained in detail in the Example section.

D. Liposome Preparation and Sizing

A variety of methods are available for preparing and sizing liposomes as described in, e.g., Szoka, et al., *Ann. Rev. Biophys. Bioeng.*, 9:467 (1980), U.S. Pat. Nos. 4,186,183, 4,217,344, 4,235,871, 4,261,975, 4,485,054, 4,501,728, 4,774,085, 4,837,028, 4,946,787, PCT Publication No. WO 91/17424, Deamer and Bangham, *Biochim. Biophys. Acta*, 443:629–634 (1976); Fraley, et al., *Proc. Natl. Acad. Sci. USA*, 76:3348–3352 (1979); Hope, et al., *Biochim. Biophys. Acta*, 812:55–65 (1985); Mayer, et al., *Biochim. Biophys. Acta*, 858:161–168 (1986); Williams, et al., *Proc. Natl. Acad Sci.*, 85:242–246 (1988), the text *Liposomes*, Marc J. Ostro, ed., Marcel Dekker, Inc., New York, 1983, Chapter 1, and Hope, et al., *Chem. Phys. Lip.*, 40:89 (1986), all of which are incorporated herein by reference. Suitable methods include, but are not limited to, sonication, extrusion, high pressure/homogenization, microfluidization, detergent dialysis, calcium-induced fusion of small liposome vesicles, and ether-infusion methods, all of which are well known in the art. One method produces multilamellar vesicles of heterogeneous sizes. In this method, the vesicle-forming lipids are dissolved in a suitable organic solvent or solvent system and dried under vacuum or an inert gas to form a thin lipid film. If desired, the film may be redissolved in a suitable solvent, such as tertiary butanol, and then lyophilized to form a more homogeneous lipid mixture which is in a more easily hydrated powder-like form. This film is covered with an aqueous buffered solution and allowed to hydrate, typically over a 15–60 minute period with agitation. The size distribution of the resulting multilamellar vesicles can be shifted toward smaller sizes by hydrating the lipids under more vigorous agitation conditions or by adding solubilizing detergents, such as deoxycholate.

Extrusion of liposome through a small-pore polycarbonate membrane or an asymmetric ceramic membrane is an effective method for reducing liposome sizes to a relatively well-defined size distribution. Typically, the suspension is cycled through the membrane one or more times until the desired liposome size distribution is achieved. The liposomes may be extruded through successively smaller-pore membranes, to achieve gradual reduction in liposome size. For use in the present invention, liposomes having a size ranging from about 0.05 microns to about 0.40 microns are preferred.

E. Use of Liposomes as Drug Delivery Vehicles

The lipid-based drug formulations and compositions of the present invention (e.g., liposomes, micelles, lipid-nucleic acid particles, virosomes, etc.) are useful for the systemic or local delivery of bioactive agents such as therapeutic agents, prophylactic agents and diagnostic agents. Such delivery systems are described in greater detail in, for example, the following copending U.S. patent application Ser. Nos. 08/454,641, 08/485,458, 08/660,025, 08/484,282, 60/055,094, 08/856,374, 60/053,813 and 60/063,473, the teachings of all of which are incorporated herein by reference.

The following discussion refers generally to liposomes; however, it will be readily apparent to those of skill in the art that this same discussion is fully applicable to the other drug delivery systems of the present invention (e.g., micelles, virosomes, lipid-nucleic acid particles, etc.).

For the delivery of therapeutic agents, the compositions can be loaded with a therapeutic agent and administered to the subject requiring treatment. The therapeutic agents which are administered using the present invention can be any of a variety of drugs which are selected to be an appropriate treatment for the disease to be treated or prevented. Often the drug will be an antineoplastic agent, such as vincristine, doxorubicin, mitoxantrone, camptothecin, cisplatin, bleomycin, cyclophosphamide, methotrexate, streptozotocin, and the like. Especially preferred antitumor agents include, for example, actinomycin D, vincristine, vinblastine, cystine arabinoside, anthracyclines, alkylative agents, platinum compounds, antimetabolites, and nucleoside analogs, such as methotrexate and purine and pyrimidine analogs. It may also be desirable to deliver anti-infective agents to specific tissues by the present methods. The compositions of the present invention can also be used for the selective delivery of other drugs including, but not limited to, local anesthetics, e.g., dibucaine and chlorpromazine; beta-adrenergic blockers, e.g., propranolol, timolol and labetolol; antihypertensive agents, e.g., clonidine and hydralazine; anti-depressants, e.g., imipramine, amitriptyline and doxepim; anti-conversants, e.g., phenytoin; antihistamines, erg., diphenhydramine, chlorphenirimine and promethazine; antibiotic/antibacterial agents, e.g., gentamycin, ciprofloxacin, and cefoxitin; antifungal agents, e.g., miconazole, terconazole, econazole, isoconazole, butaconazole, clotrimazole, itraconazole, nystatin, naftifine and amphotericin B; antiparasitic agents, hormones, hormone antagonists, immunomodulators, neurotransmitter antagonists, antiglaucoma agents, vitamins, narcotics, and imaging agents.

As mentioned above, cationic lipids can be used in the delivery of therapeutic genes or oligonucleotides intended to induce or to block production of some protein within the cell. Nucleic acid is negatively charged and may be combined with a positively charged entity to form a lipid complex or a fully encapsulated stable plasmid-lipid particle.

Particularly useful antisense oligonucleotides are directed to targets such as c-myc, bcr-abl, c-myb, ICAM-1, C-erb B-2 and BCL-2.

The CPLs of the present invention are also useful in the delivery of peptides, nucleic acids, plasmid DNA, minichromosomes and ribozymes.

Another clinical application of CPLs of this invention is as an adjuvant for immunization of both animals and humans. Protein antigens, such as diphtheria toxoid, cholera toxin, parasitic antigens, viral antigens, immunoglobulins, enzymes and histocompatibility antigens, can be incorporated into or attached onto the liposomes containing the CPLs of the present invention for immunization purposes.

Liposomes containing the CPLs of the present invention are also particularly useful as carriers for vaccines that will be targeted to the appropriate lymphoid organs to stimulate an immune response.

Liposomes containing the CPLs of the present invention can also be used as a vector to deliver immunosuppressive or immunostimulatory agents selectively to macrophages. In particular, glucocorticoids useful to suppress macrophage activity and lymphokines that activate macrophages can be delivered using the liposomes of the present invention.

Liposomes containing the CPLs of the present invention and containing targeting molecules can be used to stimulate or suppress a cell. For example, liposomes incorporating a particular antigen can be employed to stimulate the B cell population displaying surface antibody that specifically binds that antigen. Liposomes incorporating growth factors or lymphokines on the liposome surface can be directed to stimulate cells expressing the appropriate receptors for these factors. Using this approach, bone marrow cells can be stimulated to proliferate as part of the treatment of cancer patients.

Liposome-encapsulated antibodies can be used to treat drug overdoses. The tendency of liposomes having encapsulated antibodies to be delivered to the liver has a therapeutic advantage in clearing substances, such as toxic agents, from the blood circulation It has been demonstrated that whereas unencapsulated antibodies to digoxin caused intravascular retention of the drug, encapsulated antibodies caused increased splenic and hepatic uptake and an increased excretion rate of digoxin.

Liposomes containing the CPLs of this invention also find utility as carriers for introducing lipid or protein antigens into the plasma membrane of cells that lack the antigens. For example, histocompatibility antigens or viral antigens can be introduced into the surface of viral infected or tumor cells to promote recognition and killing of these cells by the immune system.

In addition, liposomes containing the CPLs of the present invention can be used to deliver any product (e.g., therapeutic agents, diagnostic agents, labels or other compounds) including those currently formulated in PEG-derivatized liposomes.

In certain embodiments, it is desirable to target the liposomes of this invention using targeting moieties that are specific to a cell type or tissue. Targeting of liposomes using a variety of targeting moieties, such as ligands, cell surface receptors, glycoproteins, vitamins (e.g., riboflavin) and monoclonal antibodies, has been previously described (see, e.g., U.S. Pat. Nos. 4,957,773 and 4,603,044, the teachings of which are incorporated herein by reference). The targeting moieties can comprise the entire protein or fragments thereof.

In some cases, the diagnostic targeting of the liposome can subsequently be used to treat the targeted cell or tissue.

For example, when a toxin is coupled to a targeted liposome, the toxin can then be effective in destroying the targeted cell, such as a neoplasmic cell.

In another aspect, the present invention provides a method for increasing intracellular delivery of a lipid-based drug formulation, comprising: incorporating into the lipid-based drug formulation, a compound of Formulae I or II, thereby increasing the intracellular delivery of the lipid based drug formulation compared to a formulation without a compound of Formulae I or II. The compounds of Formulae I or II increase intracellular delivery about 10 fold to about 1000 fold and preferably, about 10 fold to about 100000 fold.

In another aspect, the present invention provides a method of increasing the blood-circulation time of a parenterally administered lipid-based drug formulation, the method comprising: incorporating into the lipid-based drug formulation about 0.1 to 20 mole percent of a compound of Formulae I or II.

In other aspects, the present invention provides a method for transfection of a cell with a lipid-based drug formulation, comprising: contacting the cell with a lipid-based drug formulation having about 0.1 to 20 mole percent of a compound of Formulae I or II. Moreover, a method for increasing the transfection of a cell with a lipid-based drug formulation, comprising: contacting the cell with a lipid-based drug formulation having about 0.1 to 20 mole percent of a compound of Formulae I or II, whereby the transfection efficiency of the lipid-based drug formulation is increased compared to the transfection efficiency of a lipid-based drug formulation without the compound of Formulae I or II.

G. Use of the Liposomes as Diagnostic Agents

The lipid-based drug formulations or compositions, e.g., liposomes, prepared using the CPLs of this invention can be labeled with markers that will facilitate diagnostic imaging of various disease states including tumors, inflamed joints, lesions, etc. Typically, these labels will be radioactive markers, although fluorescent labels can also be used. The use of gamma-emitting radioisotopes is particularly advantageous as they can easily be counted in a scintillation well counter, do not require tissue homogenization prior to counting and can be imaged with gamma cameras.

Gamma- or positron-emitting radioisotopes are typically used, such as $^{99}$Tc, $^{24}$Na, $^{51}$Cr, $^{59}$Fe, $^{67}$Ga, $^{86}$Rb, $^{111}$In, $^{125}$L and $^{195}$Pt as gamma-emitting; and such as $^{68}$Ga, $^{82}$Rb, $^{22}$Na $^{75}$Br, $^{122}$I and $^{18}$F as positron-emitting.

The liposomes can also be labelled with a paramagnetic isotope for purposes of in vivo diagnosis, as through the use of magnetic resonance imaging (MRI) or electron spin resonance (ESR). See, for example, U.S. Pat. No. 4,728,575, the teachings of which are incorporated herein by reference.

H. Loading and Administering the Liposomes

The following discussion refers generally to liposomes; however, it will be readily apparent to those of skill in the art that this same discussion is fully applicable to the other drug delivery systems of the present invention (e.g., micelles, virosomes, lipid-nucleic acid particles, etc.). Methods of loading conventional drugs into liposomes include, for example, an encapsulation technique, loading into the bilayer and a transmembrane potential loading method.

In one encapsulation technique, the drug and liposome components are dissolved in an organic solvent in which all species are miscible and concentrated to a dry film. A buffer is then added to the dried film and liposomes are formed having the drug incorporated into the vesicle walls. Alternatively, the drug can be placed into a buffer and added to a dried film of only lipid components. In this manner, the drug will become encapsulated in the aqueous interior of the liposome. The buffer which is used in the formation of the liposomes can be any biologically compatible buffer solution of, for example, isotonic saline, phosphate buffered saline, or other low ionic strength buffers. Generally, the drug will be present in an amount of from about 0.01 ng/mL to about 50 mg/mL. The resulting liposomes with the drug incorporated in the aqueous interior or in the membrane are then optionally sized as described above.

Transmembrane potential loading has been described in detail in U.S. Pat. No. 4,885,172, U.S. Pat. No. 5,059,421, and U.S. Pat. No. 5,171,578, the contents of which are incorporated herein by reference. Briefly, the transmembrane potential loading method can be used with essentially any conventional drug which can exist in a charged state when dissolved in an appropriate aqueous medium. Preferably, the drug will be relatively lipophilic so that it will partition into the liposome membranes. A transmembrane potential is created across the bilayers of the liposomes or protein-liposome complexes and the drug is loaded into the liposome by means of the transmembrane potential. The transmembrane potential is generated by creating a concentration gradient for one or more charged species (e.g., $Na^+$, $K^+$ and/or $H^+$) across the membranes. This concentration gradient is generated by producing liposomes having different internal and external media and has an associated proton gradient. Drug accumulation can than occur in a manner predicted by the Henderson-Hasselbach equation.

The liposome compositions of the present invention can by administered to a subject according to standard techniques. Preferably, pharmaceutical compositions of the liposome compositions are administered parenterally, i.e., intraperitoneally, intravenously, subcutaneously or intramuscularly. More preferably, the pharmaceutical compositions are administered intravenously by steady infusion. Suitable formulations for use in the present invention are found in *Remington's Pharmaceutical Sciences*, Mack Publishing Company, Philadelphia, Pa., 17th ed. (1985). The pharmaceutical compositions can be used, for example, to diagnose a variety of conditions, or treat a diseased state. The diseases include, but are not limited to, inflammation associated with rheumatoid arthritis, post-ischemic leukocyte-mediated tissue damage (reperfusion injury), acute leukocyte-mediated lung injury (e.g., adult respiratory distress syndrome), septic shock, and acute and chronic inflammation, including atopic dermatitis and psoriasis. In addition, various neoplasms and tumor metastases can be treated.

Preferably, the pharmaceutical compositions are administered intravenously. Thus, this invention provides compositions for intravenous administration which comprise a solution of the liposomes suspended in an acceptable carrier, preferably an aqueous carrier. A variety of aqueous carriers can be used, e.g., water, buffered water, 0.9% isotonic saline, and the like. These compositions can be sterilized by conventional, well known sterilization techniques, or may be sterile filtered. The resulting aqueous solutions may be packaged for use as is or lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of active ingredient in the pharmaceutical formulations can vary widely, i.e., from less than about 0.05%, usually at or at least about 2–5% to as much as 10 to 30% by weight and will be selected primarily by fluid volumes, viscosities, etc., in accordance with the particular mode of administration selected. For diagnosis, the amount of composition administered will depend upon the particular label used (i.e., radiolabel, fluorescence label, and the like), the disease state being diagnosed and the judgment of the clinician.

The following examples serve to illustrate, but not to limit the invention.

EXAMPLES

I. Example I

A. General Overview

Distal cationic-poly(ethylene glycol)-lipid conjugates (CPL) were designed, synthesized and incorporated into conventional and stealth liposomes for enhancing cellular uptake. The present approach uses either inert, nontoxic or naturally occurred compounds as components for the CPL synthesis. CPLs were synthesized with the following architectural features: 1) a hydrophobic lipid anchor of DSPE for incorporating CPLs into liposomal bilayer; 2) a hydrophilic spacer of polyethylene glycol for linking the lipid anchor to the cationic head group; and 3) a naturally occurring amino acid (L-lysine) was used to produce a protonizable cationic head group. The number of charged amino groups can be controlled during the CPL synthesis. It has been demonstrated that DSPE-CPLs were almost quantitatively incorporated into liposomal bilayer by a hydration-extrusion method. Quite surprisingly, in an in vitro model, it was confirmed for the first time that liposomes possessing distal positively charged polymer conjugates with preferably four or more charges efficiently bind to host cell surfaces and enhance cellular uptake in mammalian cells.

B. Materials and Methods

1. Abbreviations: DSPE, Distearoyl-sn-glycero-3-phosphoethanolamine; DSPC, 1,2-distearoyl-sn-glycero-3-phosphocholine; DSPE-PEG$_{2000}$, 1,2-distearoyl-3-phosphatidylethanolamine-PEG$_{2000}$; TFA, trifluoroacetic acid; CPL, cationic-poly(ethylene glycol)-lipid conjugate; DSPE-CPL, (cationic-polyethylene glycol)-DSPE conjugate; DSPE-CPL-1, DSPE-CPL with one positive charge; DSPE-CPL-2, DSPE-CPL with two positive charges; DSPE-CPL-4, DSPE-CPL with four positive charges; DSPE-CPL-8, DSPE-CPL with eight positive charges; Rh-PE, (or Rho-PE), 1,2-dioleoyl-sn-glycero-3-phosphoethanolamine-N-(lissamine Rhodamine B sulfonyl).

2. Chemical: t-Boc-NH-PEG$_{3400}$-CO$_2$NHS was obtained from Shearwater polymers, Inc (Huntsville, Ala.). Nα,Nε-di-t-Boc-L-Lysine N-Hydroxysuccinide Ester, triethylamine and cholesterol were obtained from Sigma-Aldrich Canada Ltd (Oakville, ON). Trifluoroacetic acid, ethyl ether and chloroform were obtained from Fisher Scientific (Fair Lawn, N.J.). 1,2-Distearoyl-sn-glycero-3-phosphoethanolamine and 1,2-distearoyl-sn-glycero-3-phosphocholine were obtained from Avanti Polar Lipids, Inc (Alabaster, Ala.). 1,2-distearoyl-3-phosphatidylethanolamine-PEG$_{2000}$ was obtained from Genzyme (Cambridge, Mass.).

3. Synthesis of DSPE-CPL-1: To a solution of DSPE (121 mg, 161 mmol) and Et$_3$N (200 µL) in CHCl$_3$ (2 mL) at 45° C. was added t-Boc-NH-PEG$_{3400}$-CO$_2$NHS (500 mg, 147 µmol in 2 mL dry CHCl$_3$), and the solution was stirred for 3 hr at ambient temperature. The solution was concentrated under a nitrogen stream to dryness. The residue was purified by repeat precipitation of the chloroform mixture solution with diethyl ether until disappearance of DSPE spot on TLC. The purified DSPE-PEG conjugate was dissolved in 2 mL CHCl$_3$ followed by addition of 2 mL TFA, and the reaction solution was stirred at room temperature for 4 hr. The solution was again concentrated under a nitrogen stream to dryness. The residue was purified by repeat precipitation of the chloroform mixture solution with diethyl ether to offer DSPE-PEG-NH$_2$ as DSPE-CPL-1 with one protonable cationic head group: yield 500 mg (120 µmol, 80%); R$_f$ 0.4 (CHCl$_3$/MeOH, 9/1, v/v); The ratio of phosphoryl-lipid anchor and the distal primary amine was measured by phosphate and flourescamine assays and $^1$H NMR.

4. General procedure for the synthesis of DSPE-CPL-2, DSPE-CPL-4 and DSPE-CPL-8 (see FIG. 2 for schematic): To a solution of DSPE-CPL-1 (250 mg, 60 µmol) and Et$_3$N (200 µL) in CHCl$_3$ (2 mL) was added Nα,Nε-di-t-Boc-L-Lysine N-Hydroxysuccinide Ester (50 mg, 113 µmol in 2 mL dry CHCl$_3$), and the solution was stirred for 3 hr at ambient temperature. Disappearance of positive amine-active spot on TLC by nihydrin visualization indicated that the reaction was completed. The solution was concentrated under a nitrogen stream to dryness. The residue was purified by repeat precipitation of the chloroform mixture solution with diethyl ether until disappearance of t-Boc-Lysine spot on TLC. The purified DSPE-PEG-conjugates were dissolved in 2 mL CHCl$_3$ followed by addition of 2 mL TFA, and the reaction solution was stirred at room temperature for 4 hr. The solution was again concentrated under a nitrogen stream to dryness. The residue was purified by repeat precipitation of the chloroform mixture solution with diethyl ether to offer DSPE-CPL2: yield 250 mg (57 µmol, 95%); R$_f$ 0.4 (CHCl$_3$/MeOH, 9/1, v/v); The ratio of phosphoryl-lipid anchor and the distal primary amine was 1 measured by phosphate and flourescamine assays. DSPE-CPL4 and DSPE-CPL8 were synthesized in a similar manner.

5. Preparation of large unilamellar vesicles. Large unilamellar vesicles (LUV) were prepared by extrusion as described by Hope et al. (see Hope, M. J., et al., (1985) Production of large unilamellar vesicles by a rapid extrusion procedure. Characterization of size distribution, trapped volume and ability to maintain a membrane potential. Biochim. Biophys. Acta. 812, 55–65). Appropriate amounts of lipid mixtures (DSPC/Chol, 60:40 mol/mol) with or without DSPE-CPLs (as set out in Table 3) containing trace amounts of Rh-PE in chloroform, were dried under a stream of nitrogen gas to form a homogeneous lipid film. The trace amount of solvent was then removed under a vacuum overnight. The lipid film was hydrated in HBS buffer (pH 7.5) with or without HPTS (50 mM) by vortex mixing. The resulting multilamellar vesicles (MLVs) were extruded 10 times through two stacked 100 nm polycarbonate filters (Nuclepore) employing an extrusion device (Lipex Biomembranes, Inc., Vancouver, BC, Canada) at 65° C. Unincorporated DSPE-CPLs and in some cases untrapped free HPTS were removed by chromatography using a 1.1×20 cm Sepharose CL-6B column (Sigma Chemical Co., St. Louis, Mo., USA) equilibrated with HBS buffer.

6. Determination of liposome size: Liposome size was determined by quasi-elastic light scattering (QELS) using a Nicomp 370 submicron particle sizer (Santa Barbara, Calif.).

C. Results and Discussion

This example was carried out to synthesize and assess the efficacy of the distal positively charged cationic polymer lipid conjugates (CPL) to enhance the cellular uptake of CPL-incorporated liposomes. The present approach uses inert, nontoxic and naturally occurring compounds, e.g., amino acids, as components for the CPL synthesis. Several CPLs were designed with the following architectural features: 1) a hydrophobic lipid anchor for incorporating the CPLs into the liposomal bilayer; 2) a hydrophilic spacer for linking the lipid anchor to the cationic head group; and 3) a cationic head group. Moreover, the amount and nature of the cationic group can be changed according to the final application. In this example, a naturally occurring amino acid, L-lysine, was used to produce a protonizable amino group. The number of amino group can be controlled during the CPL synthesis.

Figure 5:
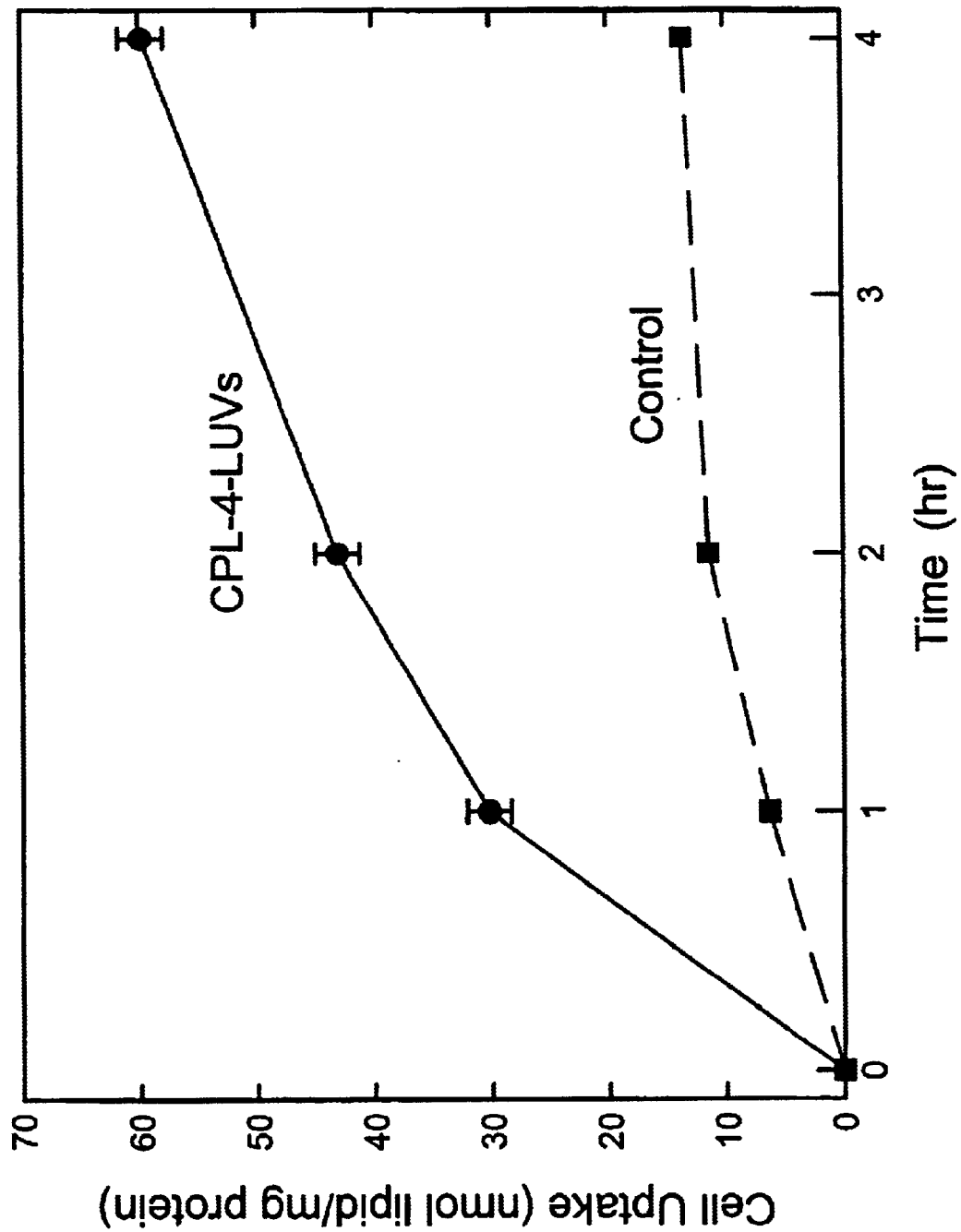
FIG. 5 illustrates a cellular uptake study of CPL-4 LUVs in BHK cells in PBS-CMG. The controls were LUVs (DSPC/Chol, 60:40) and CPL-4-LUVs (DSPC/Ch/DSPE-CPL-4, 55:40:5) were prepared by extrusion as described herein.

In analyzing these compounds, structure-function relationships in these cellular uptake enhancers may be identified. As an initial step, a variety of these CPLs with differing amounts of charge were screened for their ability to enhance uptake (see, FIGS. 5–7). In addition, the physico-chemical properties of the synthesized CPLs and the ability of these CPLs to incorporate into the liposome bilayers were also studied (see, Tables 1–3 and FIGS. 5–7). In an in vitro model, it was confirmed that these distal charged polymer conjugates significantly enhance liposome uptake in mammalian cells.

TABLE 1

Physicochemical properties of cationic CPL

| Sample | $NH_2/P$ ratio |
|---|---|
| DSPE-CPL-1 | 0.98 |
| DSPE-CPL-2 | 2.05 |
| DSPE-CPL-4 | 3.96 |
| DSPE-CPL-8 | 7.88 |

TABLE 2 pH gradients for CPL-liposomes

| Sample | Lipid composition | ΔpH |
|---|---|---|
| 1 | DSPC/Ch (60:40) | 1.84 |
| 2 | DSPC/Ch/CPL-4 (57.5:40:2.5) | 1.11 |
| 3 | DSPC/Ch/CPL-8 (57.5:40:2.5) | 0.85 |
| 4 | DSPC/Ch/PEG-PE (54:40:6) | 1.59 |
| 5 | DSPC/Ch/PEG-PE/CPL-4 (54:40:2:4) | 1.01 |
| 6 | DSPC/Ch/PEG-PE/CPL-8 (54:40:2:4) | 1.13 |

TABLE 3

CPL incorporated liposomes and their properties.

| Lipid composition | Size (nm) | CPL incorp.(%) |
|---|---|---|
| 1, DSPC/Ch(60:40) | 110 | — |
| 2, DSPC/Ch/CPL-1(57.5:40:2.5) | 120 | 98.5 |
| 3, DSPC/Ch/CPL-2(57.5:40:2.5) | 122 | 94.5 |
| 4, DSPC/Ch/CPL-4(57.5:40:2.5) | 122 | 98.1 |
| 5, DSPC/Ch/CPL-8(57.5:40:2.5) | 122 | 97.6 |
| 6, DSPC/Ch/CPL-1(55:40:5) | 120 | 98.5 |
| 7, DSPC/Ch/CPL-2(55:40:5) | 122 | 94.5 |
| 8, DSPC/Ch/CPL-4(55:40:5) | 122 | 98.1 |
| 9, DSPC/Ch/CPL-8(55:40:5) | 122 | 97.6 |
| 10, DSPC/Ch/PEG-PE(54:40:6) | 128 | — |
| 11, DSPC/Ch/PEG-PE/CPL-1(54:40:2:4) | 130 | 96.7 |
| 12, DSPC/Ch/PEG-PE/CPL-2(54:40:2:4) | 130 | 101 |
| 13, DSPC/Ch/PEG-PE/CPL-4(54:40:2:4) | 130 | 104 |
| 14, DSPC/Ch/PEG-PE/CPL-8(54:40:2:4) | 130 | 110 |
| 15, DSPC/Ch(60:40) | 110 | — |
| 16, DSPC/Ch/CPL-4(57.5:40:2.5) | 120 | 98.5 |
| 17, DSPC/Ch/CPL-8(57.5:40:2.5) | 122 | 94.5 |
| 18, DSPC/Ch/PEG-PE(54:40:6) | 128 | — |
| 19, DSPC/Ch/PEG-PE/CPL-4(54:40:2:4) | 130 | 96.7 |
| 20, DSPC/Ch/PEG-PE/CPL-8(54:40:2:4) | 130 | 101 |

II. Example II

This example illustrates that LUVs containing $CPL_4$ can be formed by a detergent dialysis method.

The LUVs contain DOPE, DODAC, PEG-Cer-C20, and $CPL_4$[3.4K] (or $CPL_4$[1K]). Two preparations were made with the CPL comprising 4 mol % of the original lipids:

TABLE 4

| Lipid | mol-% |
|---|---|
| DODAC | 6 |
| DOPE | 79.5 |
| $CPL_4$ | 4 |
| PC-C20 | 10 |
| Rho-PE | 0.5 |

The lipids indicated above were co-dissolved in chloroform, which was then removed under nitrogen followed by 2 hours under high vacuum. The dry lipid mixture (10 μmol total) was then hydrated in 83 μL of 1 M OGP and 1 mL Hepes-buffered saline (20 mM Hepes 150 mM NaCl pH 7.5) at 60° C. with vortexing until all the lipid was dissolved in the detergent solution.

The lipid-detergent mixture was transferred to Slide-A-Lyzer dialysis cassettes, and dialysed against at least 2 L HBS for 48 hours, with a least two changes of buffer in that time. Removal of detergent by dialysis results in formation of LUVs. To determine whether all of the CPL was incorporated into the LUVs following dialysis, the lipid samples were fractionated on a column of Sepharose CL-4B (see FIGS. 8A and 8B). The fractionation profiles show LUVs formed with either $CPL_4$[3.4K] or $CPL_4$[1K].

The final concentration of CPL in the LUV fraction (fractions 7–10) was estimated from initial and final dansyl/rhodamine ratios, and from estimating the proportion of total dansyl and rhodamine fluorescence present in the LUV peak. Essentially identical results were obtained.

In order to examine the effect of increasing the initial CPL concentration, a sample was made with the following proportions:

TABLE 5

| Lipid | mol-% |
|---|---|
| DODAC | 6 |
| DOPE | 71.5 |
| CPL4 | 12 |
| PC-C20 | 10 |
| Rho-PE | 0.5 |

Figure 8A:
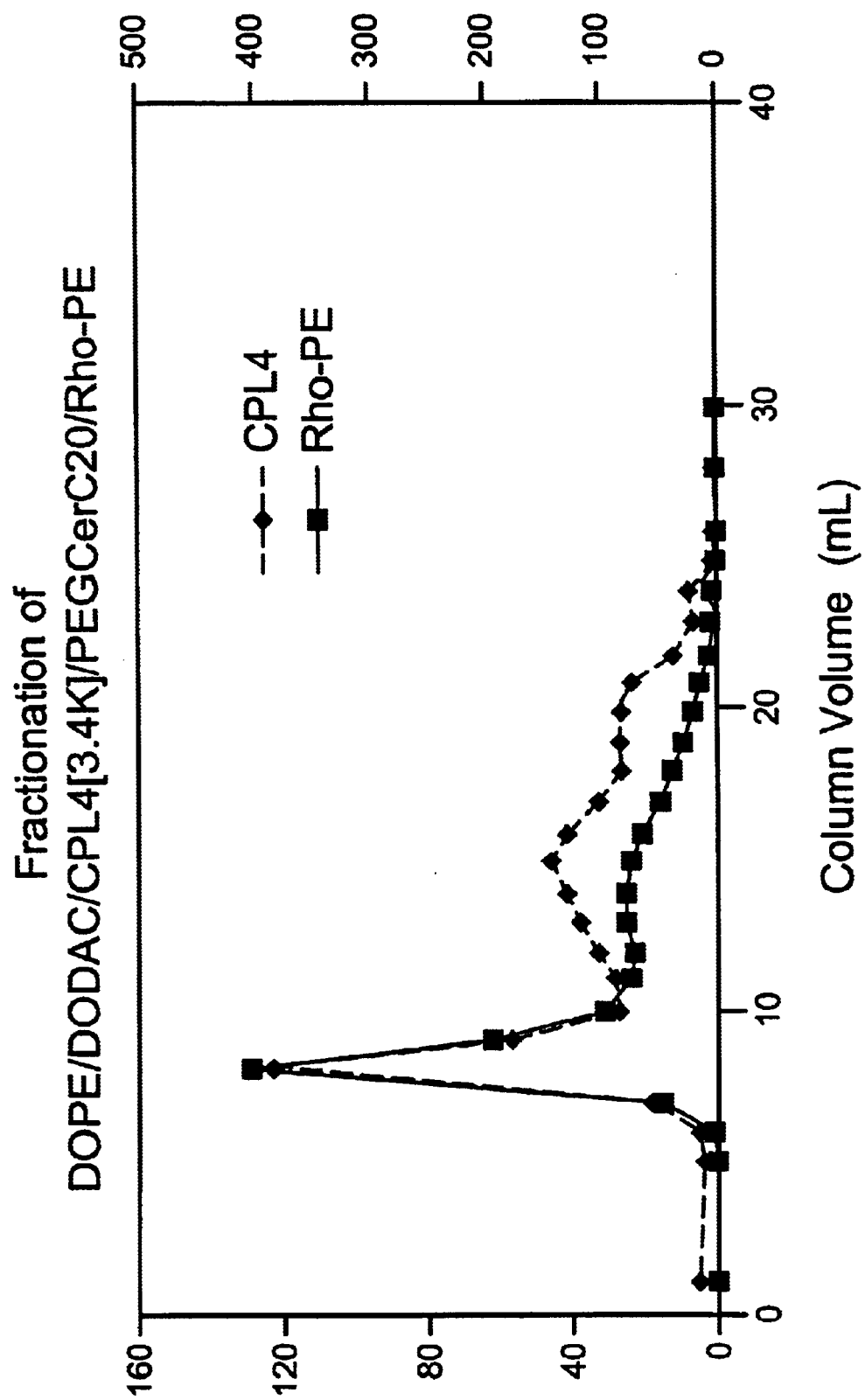
Figure 8C:
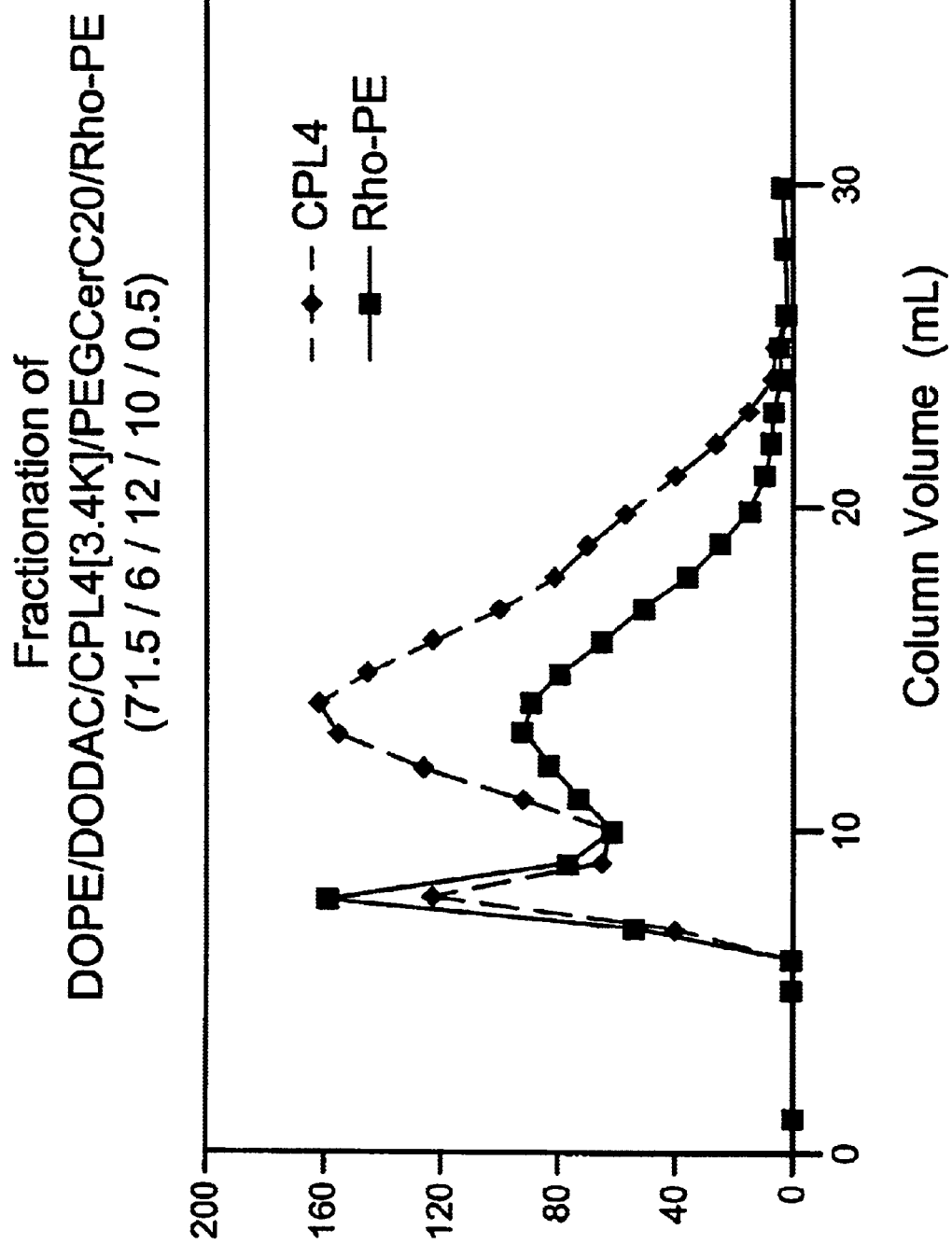

The column profile for fractionation of this sample is shown in FIG. 8C. The results for all 3 samples are given below:

TABLE 6

| Sample | original mol % CPL | %-inserted | final mol % CPL |
|---|---|---|---|
| Figure 8A | 4 | 64.6 | 2.6 |
| Figure 8B | 4 | 82.8 | 3.3 |
| Figure 8C | 12 | 50.9 | 6.1 |

Conclusion: LUVs containing $CPL_4$ can be formed by detergent dialysis. Not all of the $CPL_4$ is incorporated into the vesicle, and the proportion that is incorporated falls as the initial CPL/lipid molar ratio is increased. In the present case, beginning with 4 mol % CPL, about 3 mol % was incorporated into the LUV. For an initial CPL content of 12 mol %, a final content of 6 mol % was achieved. It is also worth noting that the behavior of the $CPL_4[1K]$ is very similar to that of the $CPL_4[3.4K]$. This is also true in post-insertion studies. In certain instances, the ideal length of the hydrophilic spacer will allow the cationic groups to extend out from the liposomal surface at a distance shorter than the normal neutral PEG that is typically being used to provide stealth properties for increased liposomal circulation lifetimes.

III. Example III

A. Overview

In this example, a non-specific targeting approach is described that involves increasing the electrostatic attraction between liposomes and cells by incorporation of positively-charged lipid molecules into preformed vesicles. This approach leads to dramatic increases in cell binding/uptake in vitro in BHK cells. The methodology is demonstrated to work for neutral vesicles and for vesicles composed of lipids used in the construct of lipid-based gene carriers. The approach outlined herein thus has numerous applications ranging from delivery of conventional drugs to gene therapy.

B. Materials and Methods

1. Materials: 1,2-dioleoylphosphatidylcholine (DOPC), 1,2-dioleoylphosphatidylethanolamine (DOPE), and 1,2-dioleoyl-sn-glycero-3-phosphoethanolamine-N-(Lissamine Rhodamine B Sulfonyl) (Rhodamine-PE) were obtained from Avanti Polar Lipids. Cholesterol was obtained from Sigma Chemical Co. DODAC and PEGCerC20, PEGCerC14, and PEGCerC8 were generous gifts from Inex Pharmaceuticals.

2. Synthesis of cationic-PEG lipids: The details of the synthesis of the CPLs is described herein. Two types of CPLs were synthesized which differed in the lipid anchor portion of the molecule. In one, the anchor was distearoylglycerol (DSG), while the other contained distearoylphosphatidylethanolamine (DSPE). The molecule consists of the anchor portion, to which is attached a $PEG_{3400}$ chain. At the end of the PEG chain, a charged "headgroup" is attached, often made up of lysine residues linked together. By modifying the headgroup region, CPLs were synthesized which contained 1 (mono, or M), 2 (di, or D), 3 (tri, or T), and 4 (quad, or Q) positive charges. Several different Quad CPLs were synthesized, hence these are numbered Q1 through Q5. The nomenclature chosen to describe these compounds specifies the type of lipid anchor and the identity of the headgroup (e.g., d-DSPE-CPL-Q5). The lower case "d" indicates a dansylated derivative.

3. Preparation of Vesicles by Detergent Dialysis. In general, vesicles were formed using a detergent dialysis method (see, Wheeler, J. J., et al. (1999) Stabilized plasmid-lipid particles: construction and characterization. Gene Therapy 6, 271–281, the teachings of which are incorporated herein by reference). The lipids, as described in Example II, were co-dissolved in chloroform in the appropriate ratios, following which the chloroform was removed under a stream of nitrogen and placed under high vacuum for 2 hours. An aliquot of the non-ionic detergent octylglucopyranoside (1 M in water) (OGP) was then added to the dry lipid film, which was incubated for 10–20 minutes at 60° C. with frequent vortexing. This was followed by addition of 20 mM HEPES 150 mM NaCl pH 7.5, with further warming and vortexing until all the lipid was dispersed and a clear solution was obtained. For 20 mg of lipid, 0.125 mL of OGP and 1 mL of HBS were used. The lipid-detergent solutions (1–2 mL) were then transferred to Slide-A-Lyzer dialysis membranes (3 mL volume) and exhaustively dialysed at room temperature against HBS over a period of 48 hours. In general, a total volume of 8–10 L of HBS was used (4–5 changes of 2 L) for sample volumes of 1–8 mL.

Vesicles of DOPC and DOPC/Chol (55:45) were prepared by extrusion as previously described (Hope, M. J., et al., (1985) Production of large unilamellar vesicles by a rapid extrusion procedure. Characterization of size distribution, trapped volume and ability to maintain a membrane potential. Biochim. Biophys. Acta 812, 55–65).

4. Insertion of Cationic PEG-lipids into preformed vesicles. The cationic PEG-lipids (CPLs) were stored as micellar solutions in HBS or, in a few cases, in methanol. The CPL and the vesicles were combined to give the desired molar ratio (up to 11.6 mol % CPL relative to vesicle lipid), and incubated for a given time at the desired temperature. For most insertions, the standard conditions involved a 3 hour incubation at 60° C. Following insertion, the samples were cooled on ice, and the CPL-LUV was separated from free CPL by passage down a column (1.5×15 cm) of Sepharose CL-4B equilibrated in HBS. FIG. 16 illustrates the insertion protocol for SPLPs (an analogous procedure).

The insertion levels of CPL were measured by fluorescence. In all cases, the vesicles contained either 0.25 mol % or 0.5 mol % rhodamine-PE, and the CPL contained a dansyl group. After combining the CPL and lipids, a 15 µL aliquot (initial fraction) was set aside for analysis. The amount of CPL inserted into the vesicles could then be quantified by measuring the initial dansyl/rhodamine (D/R) fluorescence ratio, and the D/R ratio of the isolated CPL-LUVs. Fluorescence parameters: for the rhodamine assay, the excitation wavelength was 560 nm, and the emission wavelength was 590 nm. For the dansyl assay, the excitation wavelength was 340 nm, and the emission wavelength was 510 nm. In general, the excitation and emission slit widths were 10 and 20 nm, respectively. The assay was performed as follows: to an aliquot of the initial sample (2–3 µL) or the CPL-LUV (20–40 µL) was added 30 µL of 10% Triton X-100 followed by 2 mL of HBS. The fluorescence levels of both the dansyl and rhodamine labels were read consecutively using a wavelength program as per the above parameters with an emission filter of 410 nm. The %-insertion was calculated as follows:

$$\%\text{-insertion} = ([D/R]_{CPL-LUV}) * 100/[D/R]_{INITIAL}$$

5. Measurement of Lipid Concentrations: Following insertion, it is necessary to know the lipid concentration of each sample for cell binding studies. This can be done quickly by fluorescence. Following detergent dialysis, the lipid concentration of each sample was measured using the standard phosphate assay (Fiske, C. H., and Subbarow, Y. (1995) The calorimetric determination of phosphorus. J. Biol. Chem. 66, 375–400). An aliquot was then diluted to approximately 3 mM. By comparing the rhodamine fluorescence of this sample, whose lipid concentration is known, with the CPL-LUVs prepared from that stock, allows determination of CPL-LUV concentrations. Lipid concentrations of LUVs were measured using the standard phosphate assay. Following CPL insertion, lipid concentrations were estimated for cell binding studies from the rhodamine fluorescence.

6. Uptake of CPL-containing LUVs by BHK cells. Approximately $10^5$ BHK cells were incubated in PBS/CMG medium with 20 nmol of DOPE/DODAC/PEGCerC20 (84/6/10) LUVs containing either (1) no CPL, (2) 8% DSPE-CPL-D, (3) 7% DSPE-CPL-T1, or (4) 4% DSPE-CPL-Q5. Incubations were performed for 1, 2, 4, and 6 hours at 4° C. and 37° C., the former giving an estimate of cell binding, and the latter of binding and uptake. By taking the difference of the two values, an estimate of lipid uptake at 37° C. was obtained. For each timepoint, the cells were ruptured and assayed for lipid and protein. Lipid concentrations were measured from rhodamine fluorescence, while protein was determined using the BCA assay. Lipid concentrations were measured using rhodamine fluorescence, while protein was determined using the BCA assay kit obtained from Pierce.

C. Results and Discussion

Figure 9A:
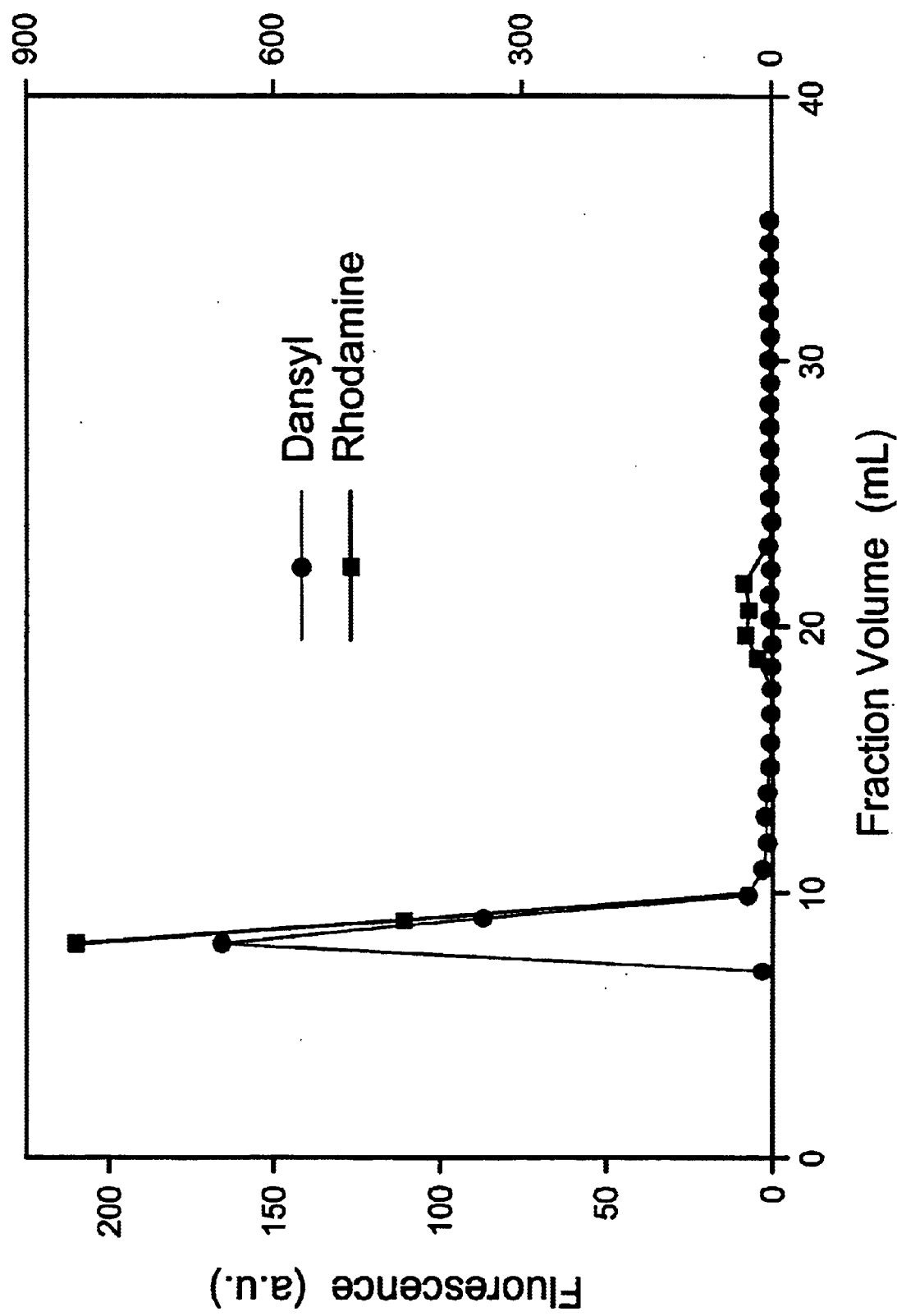
FIG. 9A illustrates the insertion of DSPE-CPL-Q5 into DOPC LUVs (100 nm). DOPC LUVs (2.5 μmol lipid) were incubated with 0.214 μmol DSPE-CPL-Q5 (total volume 300 μl) at 60° C. for 3 hours, following which the sample was applied to a column of Sepharose CL-4B equilibrated in HEPES-buffered saline. 1 mL fractions were collected and assayed for dansyl-labelled CPL and rhodamine-PE as described herein.
Figure 9B:
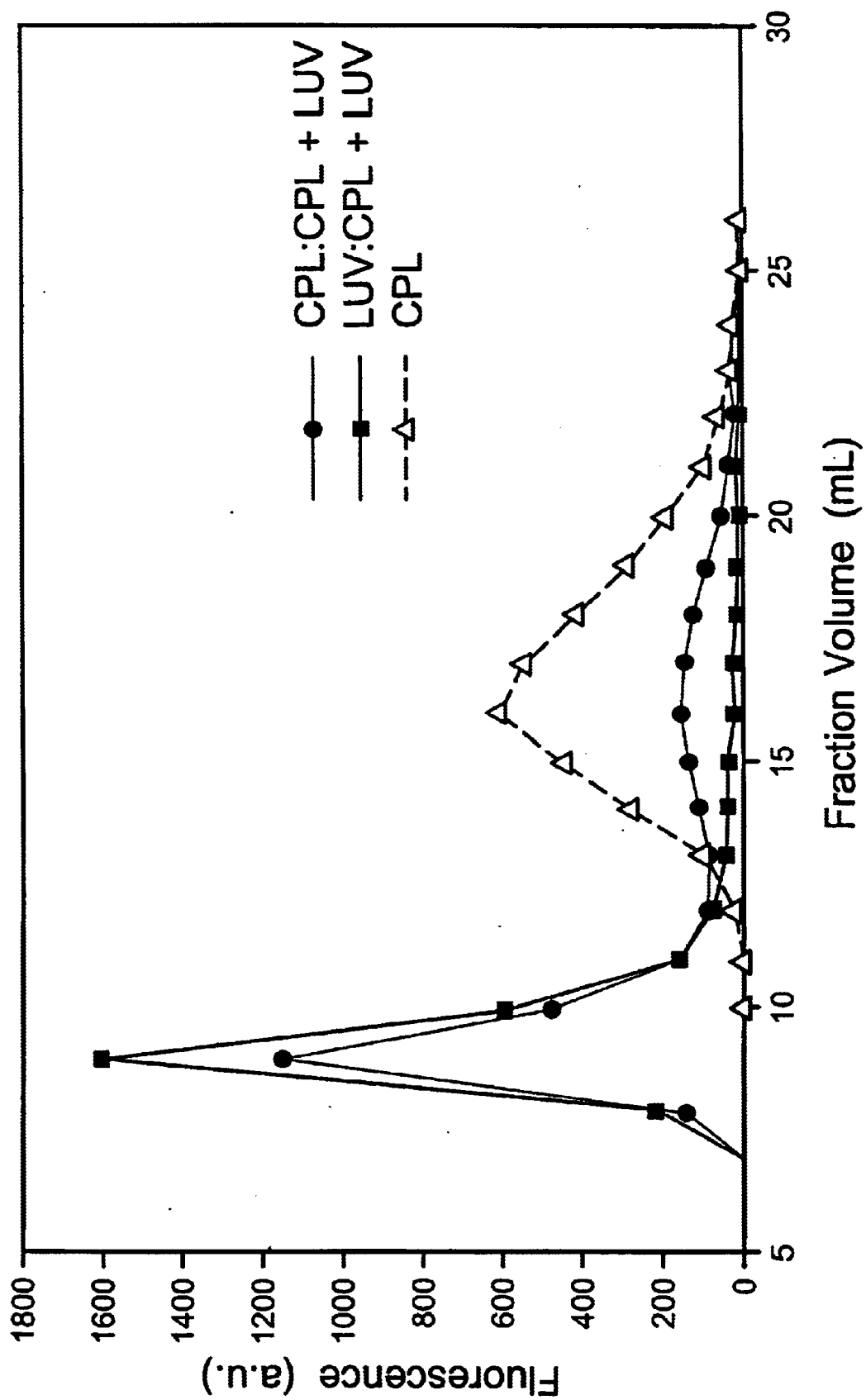
FIG. 9B illustrates the insertion of DSPE-CPL-Q5 into LUVs (100 nm) composed of DOPE/DODAC/PEG-Cer-C20 (84/6/10). LUVs (5 μmol lipid) were incubated with 0.43 μmol DSPE-CPL-Q5 (total volume 519 μl) at 60° C. for 3 hours, following which the sample was applied to a column of Sepharose CL-4B equilibrated in HEPES-buffered saline. The elution of free CPL is also shown, demonstrating a straightforward method for isolation of the CPL-LUV. 1 mL fractions were collected and assayed for dansyl-labelled CPL and rhodamine-PE as described herein.
Figure 9C:
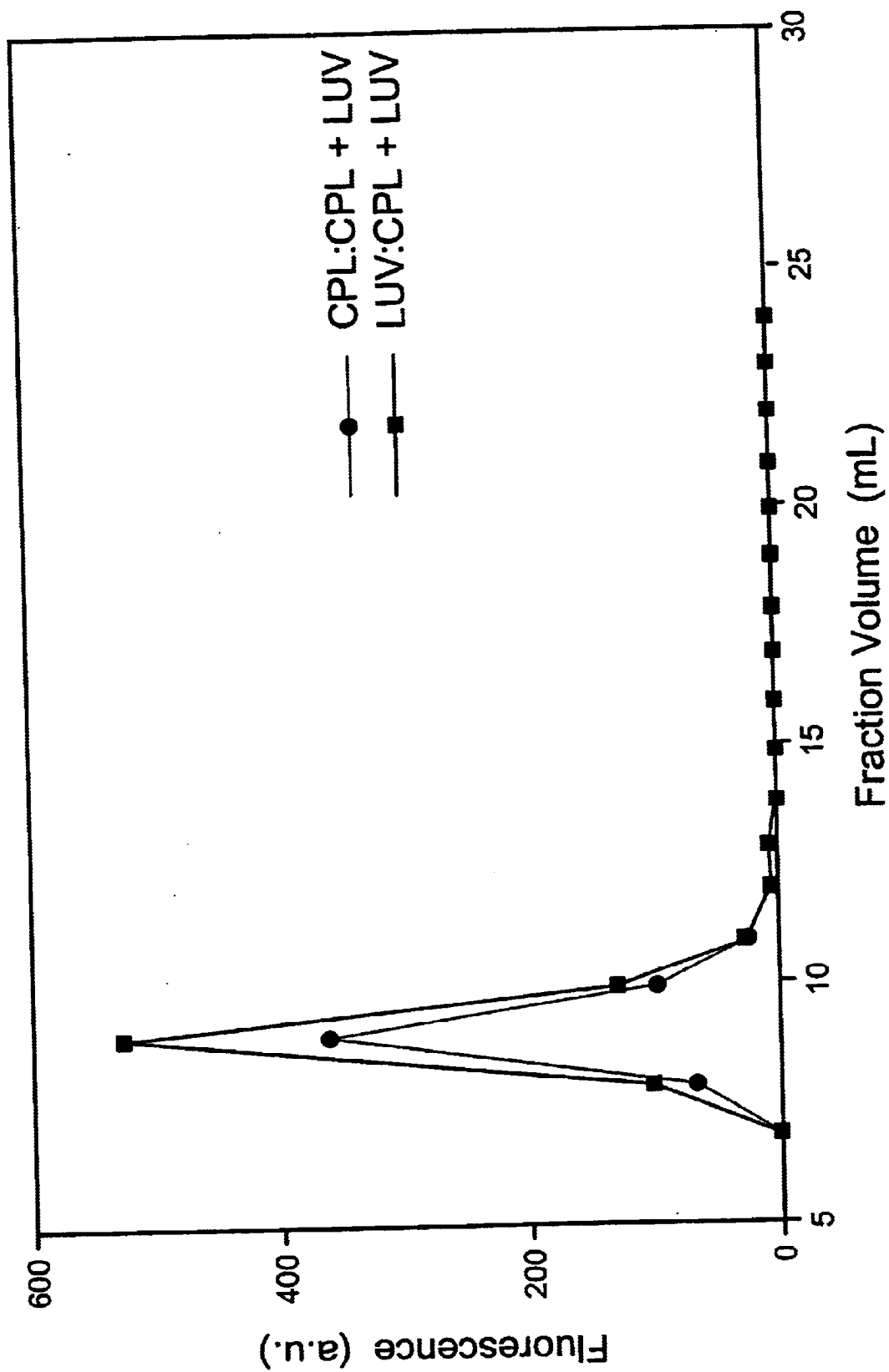
FIG. 9C illustrates retention of DSPE-CPL-Q5 in LUVs (100 nm) composed of DOPE/DODAC/PEG-Cer-C20 (84/6/10). The main LUV fraction from FIG. 9 Panel B was re-applied to a column of Sepharose CL-4B equilibrated in HEPES-buffered saline. 1 mL fractions were collected and assayed for dansyl-labelled CPL and rhodamine-PE as described.

1. Development of Insertion Protocol. The transfer of pegylated lipids from micellar aggregates to vesicles has been previously described (see, Uster, P. S., et al., (1996) Insertion of poly(ethylene glycol) derivatized phospholipid into pre-formed liposomes results in prolonged in vivo circulation time. *FEBS Letters* 386, 243–246; Zalipsky, S., et al., (1997) Poly(ethylene glycol)grafted liposomes with oligopeptide or oligosaccharide ligands appended to the termini of the polymer chains. *Bioconjugate Chem.* 8, 111–118). This idea was tested with DSPE-CPL's. This is demonstrated in FIG. 9(A) for DOPC LUVs. The co-elution of the dansyl and rhodamine labels demonstrates incorporation of the CPL in the LUVs. In this case, 84% of the CPL was incorporated into the LUVs, and thus only a trace of free CPL is observed trailing the CPL-LUV fractions. This is more clearly seen in FIG. 8(B), where the DSPE-CPL-Q5 has been inserted into a more complex positively charged vesicles composed of DOPE/DODAC/PEGCerC20 (84/6/10). Here, the co-elution of the two fluorescent labels at approx. 9 mLs demonstrates 70% insertion of the CPL into the vesicles. The free CPL elutes in a broad peak centered at 16 mLs, which is separate from the vesicle peak, allowing for easy isolation of the CPL-LUV. Once inserted, the DSPE-CPL-Q5 is retained and does not exchange out of the vesicles. The CPL-LUV fraction from FIG. 9(B) was re-eluted on the column of Sepharose CL-4B. As shown in FIG. 9(C), all of the CPL remains with the LUVs.

Figure 10:
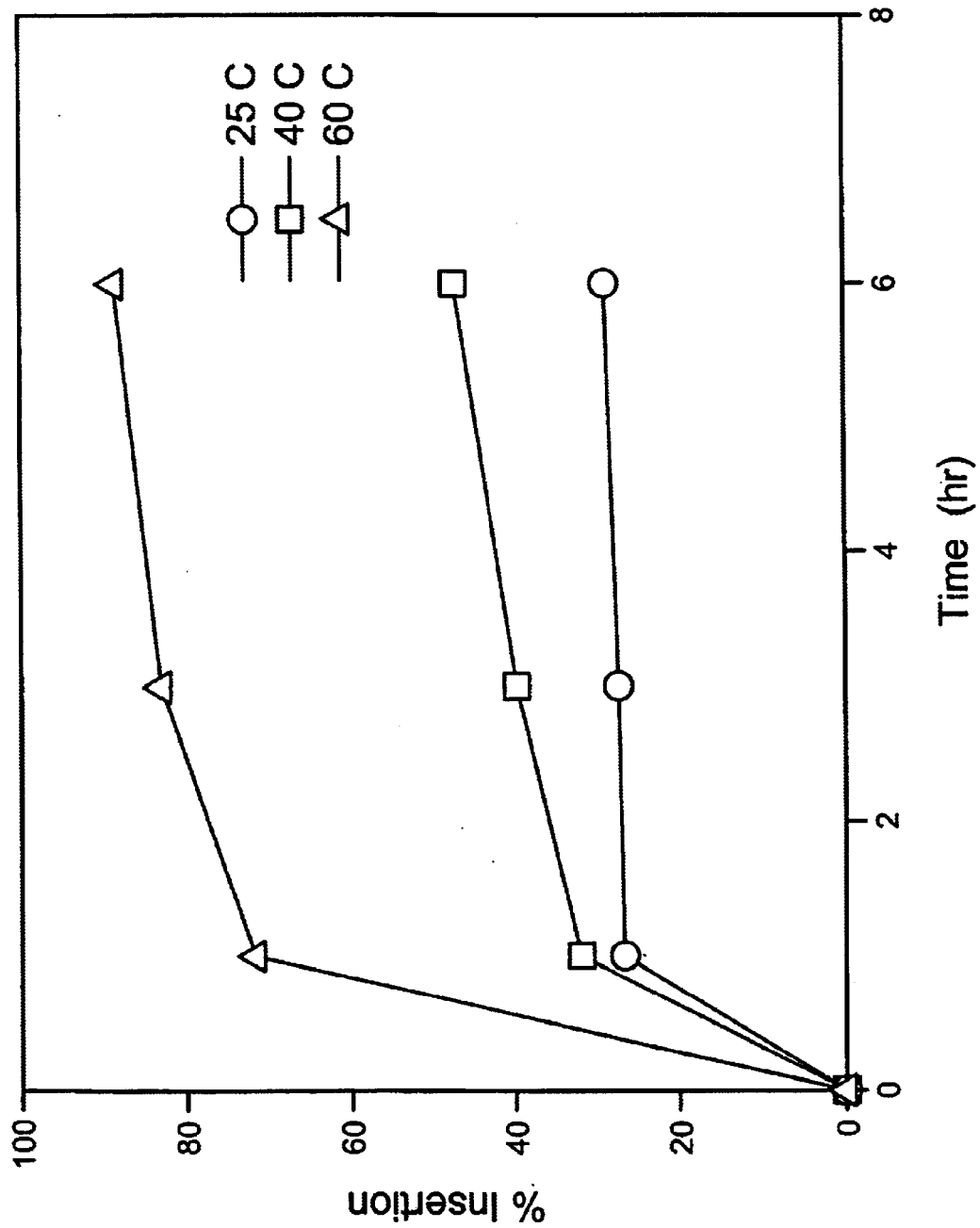
FIG. 10 illustrates the effect of time and temperature on the insertion of d-DSPE-CPL-Q1 into DOPE/DODAC/PEG-Cer-C20 LUVs. For each of the 3 temperatures, 3 μmol lipid was combined with 0.17 μmol CPL (total volume 240 μl). At 1, 3, and 6 hours, 1 μmol of lipid was withdrawn and cooled in ice to halt insertion of CPL. The samples were passed down a column of Sepharose CL-4B to remove excess CPL, and assayed for CPL insertion.

The effects of incubation temperature and time on the insertion process are shown in FIG. 10. DSPE-CPL-Q1 was incubated in the presence of DOPE/DODAC/PEGCerC20 (84/6/10) at room temperature, 40° C., and 60° C., with aliquots withdrawn at 1, 3, and 6 hours. The highest insertion levels were achieved at 60° C., which was therefore used in subsequent insertions. Although slightly higher insertion was obtained at 6 hr, we chose 3 hr to minimize sample degradation.

Figure 11:
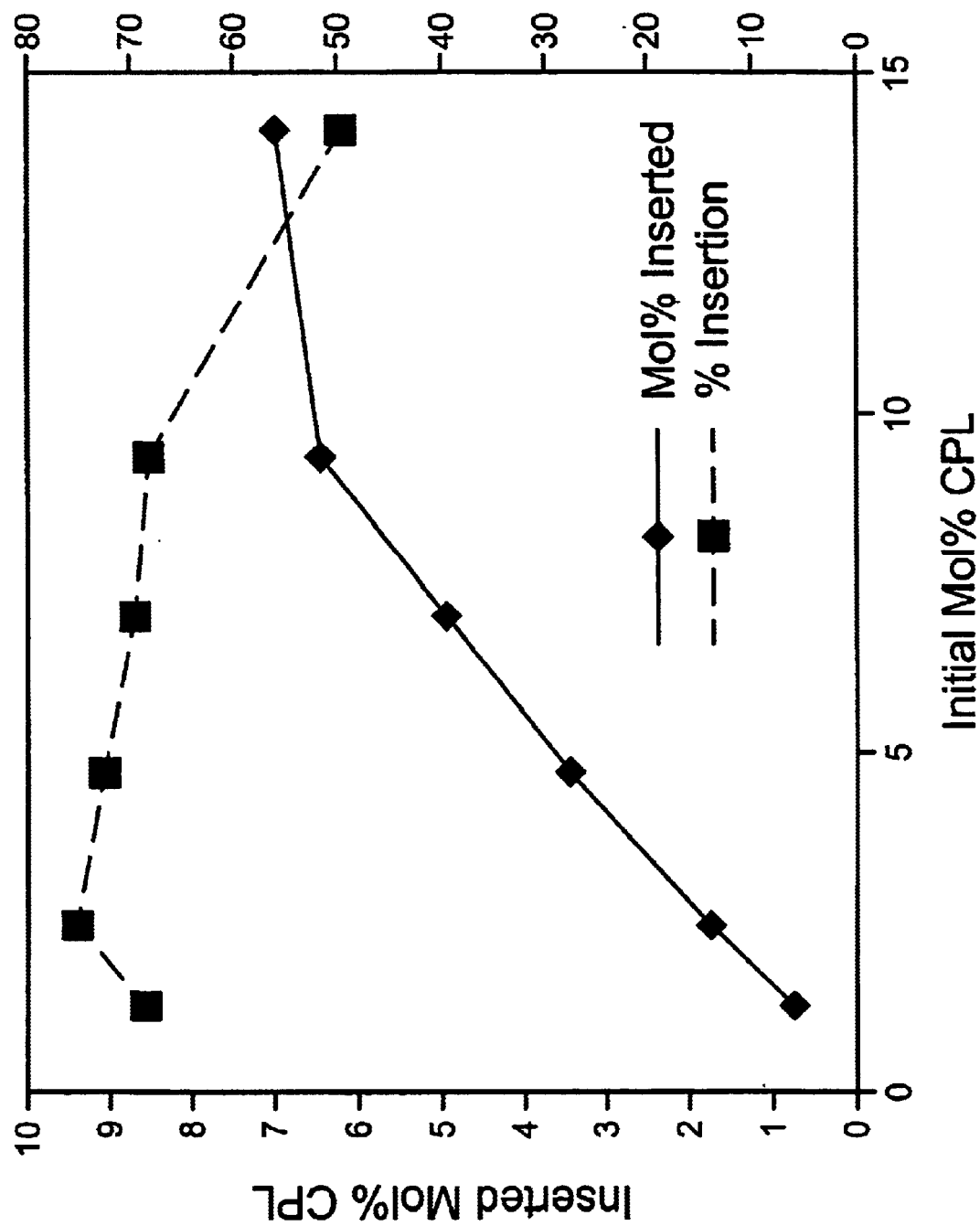
FIG. 11 illustrates the effect of initial CPL/lipid ratio on final CPL insertion levels. Initial CPL/lipid molar ratios were 0.011, 0.024, 0.047, 0.071, 0.095, and 0.14. Final mol % inserted were 0.8, 1.8, 3.4, 5.0, 6.5, and 7.0. Right-hand axis is %-insertion.

Aside from time and temperature, the parameter that will have the greatest influence on final CPL insertion levels is the initial CPL/lipid ratio. Assuming about 70% insertion, a series of incubations were performed with CPL/lipid molar ratios varying between 0.011 to 0.14, with the aim to achieve CPL-LUVs containing 1, 2, 4, 6, 8, and 12 mol % CPL. These results are shown in FIG. 11, where it is seen that the insertion level remains close to 70% up to an initial CPL/lipid ratio of 0.095, above which it drops to 50% for CPL/lipid=0.14.

Figure 12:
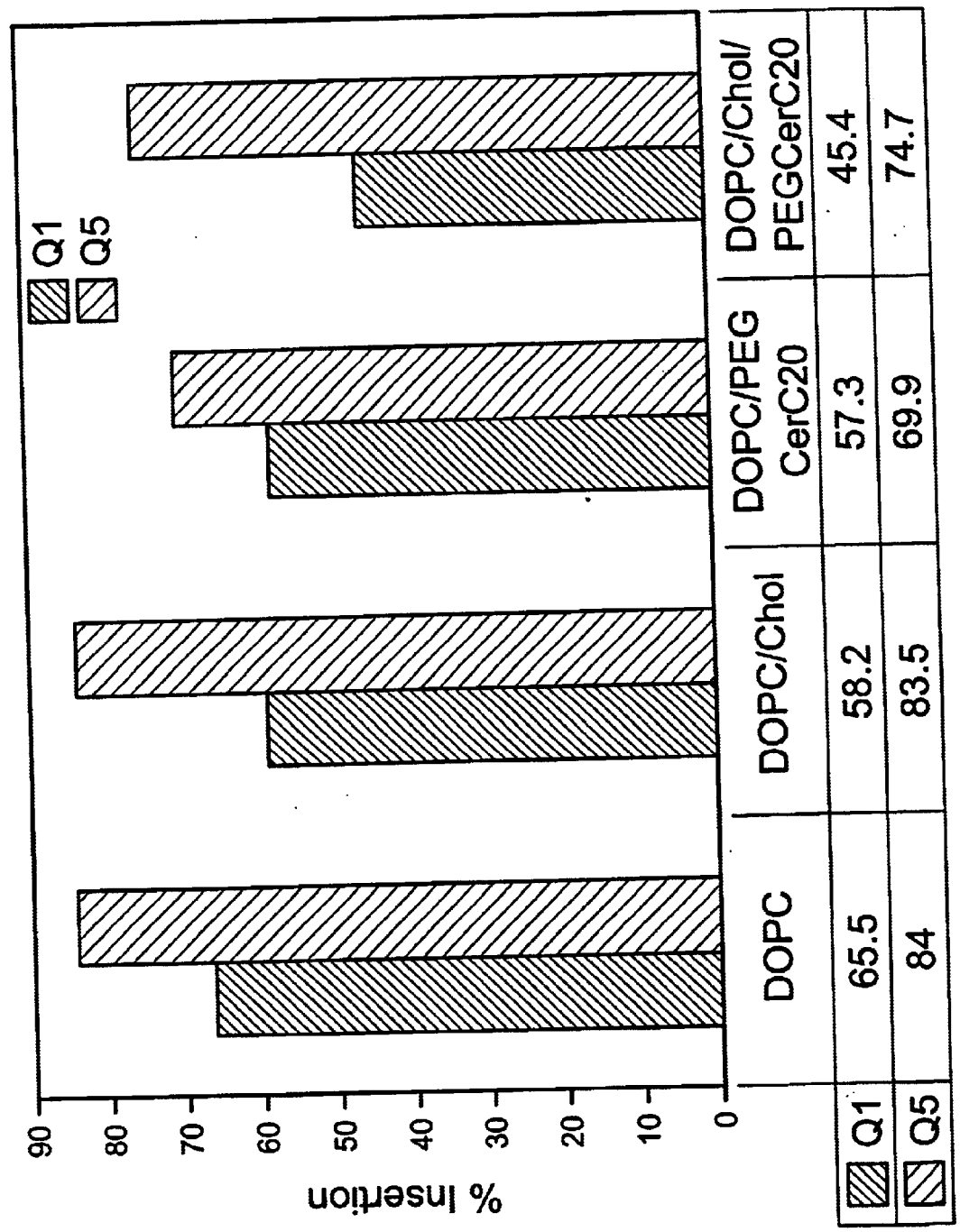
FIG. 12 illustrates the insertion of DSPE-CPL-Q1 and DSPE-CPL-Q5 into neutral vesicles. The initial CPL/lipid molar ratio was 0.065 for Q1 (2.5 μmol lipid and 0.21 μmol CPL) and 0.034 for Q5. Samples were incubated at 60° C. for 3 hours. The DOPC and DOPC/Chol LUVs were prepared by extrusion, while the others were prepared by detergent dialysis. As described herein, the presence of 4% methanol in the Q5 samples appear to account for the higher insertion observed for this sample. Sample compositions were as follows: DOPC/Chol (55/45), DOPC/PEG-Cer-C20 (90/10), DOPC/Chol/PEG-Cer-C20 (45/45/10).

Similar results were obtained for other vesicle systems, including DOPE/DODAC/PEGCerC14 and DOPE/DODAC/PEGCerC8. In general, the insertion levels obtained with DODAC-containing samples fell in the range of 70–80% for initial CPL/lipid<0.1. In order to see whether the insertion levels were effected by the presence of cationic lipid, several experiments were performed on neutral vesicles containing DOPC. The compositions examined were: (1) DOPC, (2) DOPC/Chol, (3) DOPC/PEGCerC20, and (4) DOPC/Chol/PEGCerC20. The results, shown in FIG. 12, reveal that for the DSPE-CPL-Q1, somewhat less insertion was achieved in the neutral systems: between 45–65%. This may be due to reduced attraction between the negatively-charged DSPE anchor and the membrane surface. Regardless, the results demonstrate that significant insertion can be achieved for both neutral and positive vesicles.

Figure 13:
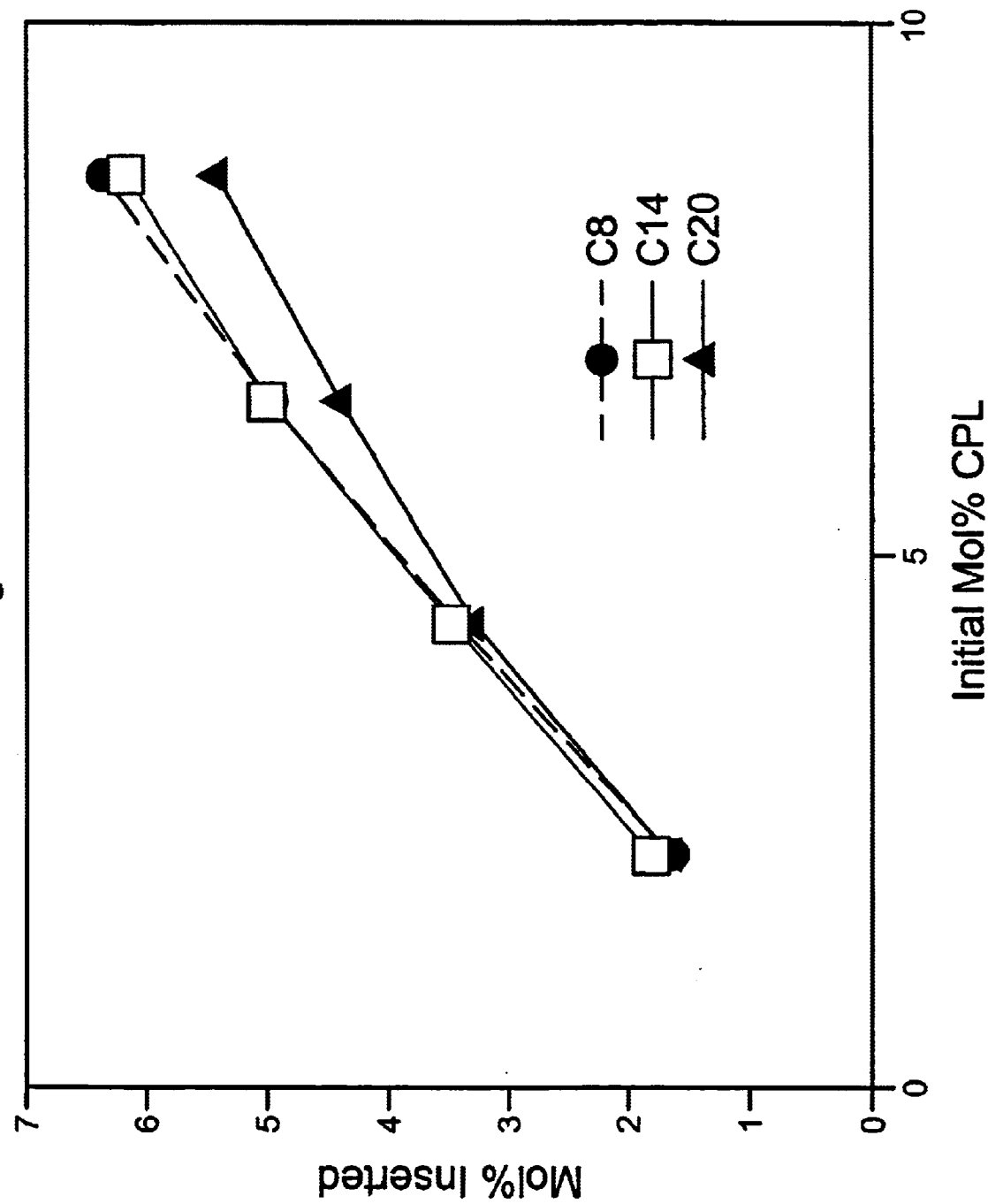
FIG. 13 illustrates the effect of chain length of PEG-Cer on mol-% CPL inserted. LUVs composed of DOPE/DODAC/PEG-Cer-C20 (84/6/10), DOPE/DODAC/PEG-Cer-C14 (84/6/10), and DOPE/DODAC/PEG-Cer-C8 (79/6/15) were incubated in the presence of between 2–8.6 mol % d-DSPE-CPL-Q1 at 60° C. for 3 hrs.

It should be noted that the insertion levels for the DSPE-CPL-Q5 also shown in FIG. 13 are much higher than for the Q1 (70–84%). There is a reason for the differential behavior of the Q1 and Q5 CPLs in these systems, when in prior experiments they behaved very similar. This particular batch of Q5 was prepared in methanol, a solvent in which the lipids may exhibit greater storage stability. As explained herein, it has been found that the presence of methanol in the incubation mixture leads to higher insertion.

A large number of insertions have been performed using other CPLs in addition to the Q5 and Q1. These results are summarized in Tables 7 and 8, (FIGS. 23 and 24) where some composition-dependent trends can be ascertained. First, the same trend seen above in FIG. 11 with the Q5 hold for several CPLs with differing charge. As the initial ratio of CPL/lipid is increased, the percentage of CPL inserted decreases. If we look at the T1, Q1, and Q5 incubations where CPL/lipid=0.022–0.024, the %-insertion ranges from 76–80%. However, for CPL/lipid=0.086–0.095, the %-insertion range decreases to 62–68%.

Figure 14:
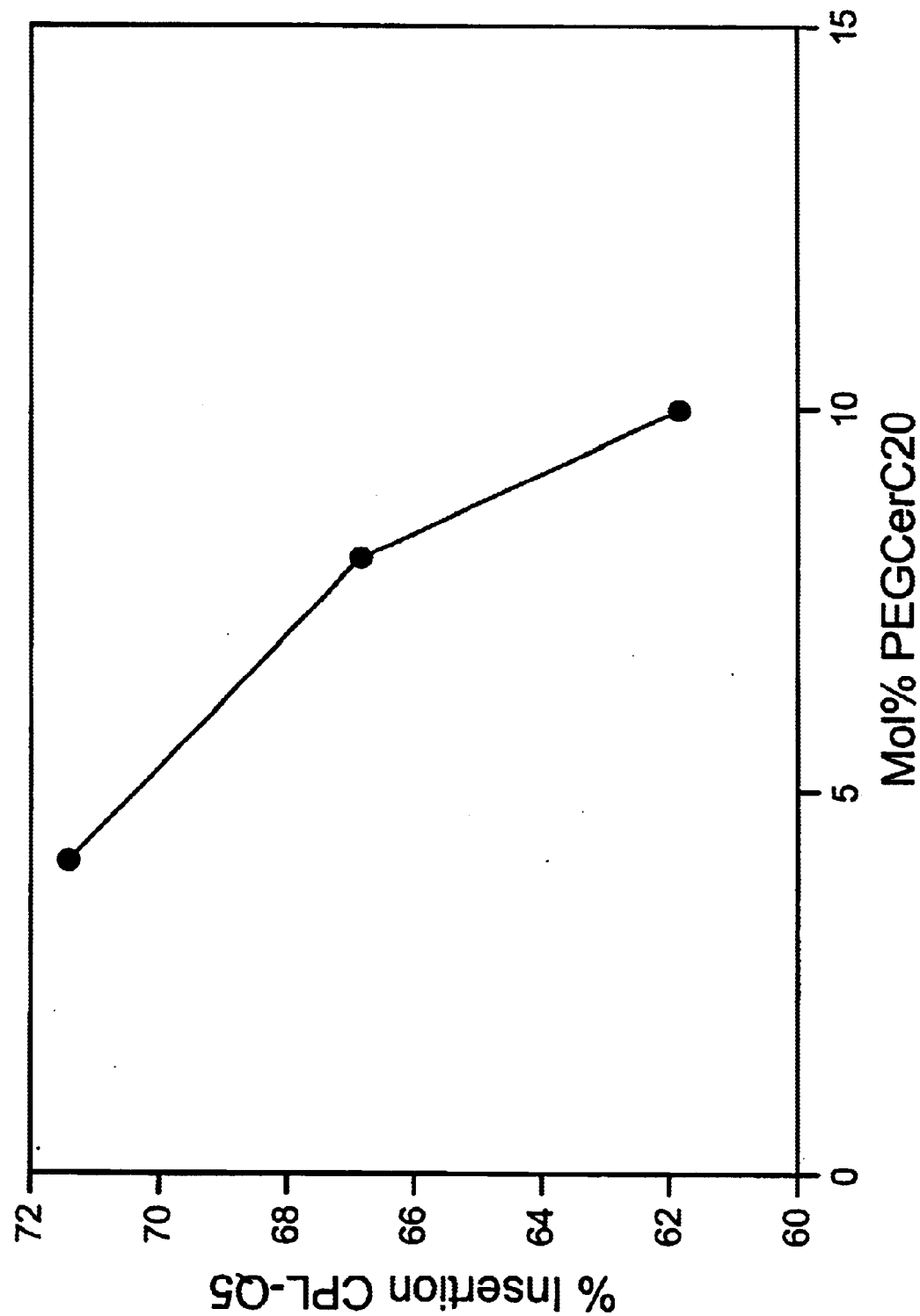
FIG. 14 illustrates the effect of PEG-Cer-C20 content on insertion of d-DSPE-CPL-Q5. Vesicles composed of DOPC/DODAC/PEGCerC20, with the latter lipid ranging from 4–10 mol %, were incubated in the presence of CPL-Q5 (initial CPL/lipid molar ratio=0.071).

Another trend is illustrated in FIG. 13. For initial CPL/lipid ratios>0.04, slightly less CPL-Q1 is inserted into LUVs containing PEG-Cer-C20 than into those containing either of the shorter chain PEGs. In addition to the type of PEG anchor present, the quantity of PEG-Cer also has an effect on insertion, as seen in FIG. 14. As the PEG-Cer-C20 content is increased from 4 to 10 mol %, the insertion levels of CPL-Q5 fall from 71 to 62%.

As those of skill in the art will readily appreciate, the lipid anchor can be varied and the insertion levels may vary depending on the lipid used as the lipid anchor. For instance, some experiments were performed with CPL containing a DSG (distearoylglycerol) anchor: in all cases the insertion levels were much lower, from 17–40%, than in CPL containing a DSPE anchor. Using the methods and assays of the present invention, those of skill in the art can readily identify suitable lipid anchors.

In order to check for possible aggregation following CPL insertion, quasi-elastic light scattering (QELS) was used to examine the effect of insertion on particle diameter. DOPE/DODAC/PEG-Cer-C20 vesicles were found to have a diameter of 119±39 nm. Following insertion of 18 mol % CPL4b, a slight increase in diameter to approx. 135±42 nm was observed, but both the mean diameter and standard deviation remained constant up to 7 mol % CPL. The increase from 120 nm to 135 nm could reflect a slightly larger diameter resulting from the presence of the longer CPL PEG chains or it could indicate a small amount of vesicle aggregation. To differentiate between these two possibilities, CPL-LUVs were examined by fluorescence microscopy, using a rhodamine filter. While control LUVs exhibited no signs of aggregation, significant levels were observed for CPL-LUVs. However, it was found that addition of 40 mM $CaCl_2$ completely prevented this effect.

As described in Materials & Methods, estimates were obtained for the uptake of various CPL-LUVs on BHK cells incubated on PBS/CMG. The data, shown in FIG. 15, reveals that the presence of positive charge on the CPLs can lead to significant enhancement in uptake by BHK cells. LUVs composed of DOPE/DODAC/PEGCerC20 (and thus exhibiting a net positive charge) showed little uptake on the BHK cells. LUVs containing 8 mol % of DSPE-CPL-D showed similar low uptake values. Uptake was only slightly increased by the presence of 7 mol % of DSPE-CPL-T1. However, a significant increase in uptake was realized for DSPE-CPL-Q5 present at only 4.1 mol %. Several points can be surmised from this data. While it is clear that an increase in the positive charge present at some distance from the LUV surface leads to an increase in uptake, it is not total charge alone that plays a role in enhanced cell binding. The quantity of positive charge present for the DSPE-CPL-D and DSPE-CPL-Q5 samples is approximately equal, and yet the former shows little binding compared to the latter. The DSPE-CPL-T1 sample has a greater positive charge than the DSPE-CPL-Q5 sample, and yet exhibits only ⅓ the uptake. It would appear that localization of a sufficient positive charge density at the distal end of the CPL molecule is an important parameter in ensuring interaction with cells. In a preferred embodiment, at least four charges are used to achieve efficient cell binding.

The dramatic effect of CPL insertion on LUV binding to BHK cells is most clearly visualized using fluorescence microscopy. In the absence of CPL, vesicles composed of DOPE/DODAC/PEG-Cer-C20 and containing a trace of rhodamine-PE exhibit little binding to cells. Incorporation of 3 mol % CPL4b leads to high levels of vesicle binding and uptake. Although much of the lipid appears to be binding to the cell surface, some small punctate structures can be seen, indicating that uptake of vesicles is also occurring. An important point to note is that the cells appear healthy following incubation in the presence of the CPL-LUVs. In contrast, DNA-cationic lipid complexes are known to display significant toxicity.

One of the major remaining hurdles in liposomal drug delivery is the problem of how to ensure that the contents of a carrier system are taken up and utilized by a specific target cell. It is now believed that the cellular uptake of liposomes involves adsorption or binding at the cell surface, followed by endocytosis. Thus factors which interfere with cellular binding will lead to low levels of intracellular delivery. This is of particular importance for 'stealth' or long-circulating liposomes that are coated with a surface layer of a hydrophilic polymer such as PEG. The very characteristic of the PEG coating which imparts long-circulation lifetimes—the formation of a steric barrier that prevents interaction with serum proteins, will also minimize interactions with cells. On the other hand, factors that enhance surface binding may be expected to lead to increased cellular uptake. One approach involves attaching molecules specific for membrane receptors to liposomal surfaces. Possible candidates include oligopeptides (see, Zalipsky et al., *Bioconjugate Chemistry* 6, 705–708 (1995); Zalipsky et al., *Bioconjugate Chemistry* 8, 111–118 (1997)) oligosaccharides (see, Zalipsky et al., *Bioconjugate Chemistry* 8, 111–118 (1997)), folate (see, Gabizon et al., *Bioconjugate Chemistry* 10, 289–298 (1999); Lee et al., *Journal of Biological Chemistry* 269, 3198–3204 (1994); Reddy et al., *Critical Reviews in Therapeutic Drug Carrier Systems* 15, 587–627 (1998); Wang et al., *Journal of Controlled Release*, 53, 39–48 (1998)), riboflavin (see, Holladay et al., *Biochimica et Biophysica Acta* 1426, 195–204 (1999)), or antibodies (see, Meyer et al., *Journal of Biological Chemistry* 273, 15621–15627 (1998); Kao et al., *Cancer Gene Therapy* 3 250–256 (1996); Hansen et al., *Biochimica et Biophysica Acta* 1239, 133–144 (1995)]. An alternate approach is to modify the charge characteristics of the liposome. It is well known that inclusion of either negative (see, Miller et al., *Biochemistry* 37, 12875–12883 (1998); Allen et al., *Biochimica et Biophysica Acta* 1061, 56–64 (1991); Lee et al., *Biochemistry* 32, 889–899 (1993); Lee et al., *Biochimica et Biophysica Acta* 1103, 185–197 (1992)) or positive (see, Miller et al., *Biochemistry* 37, 12875–12883 (1998)) charges in liposomes can lead to enhanced cellular uptake. Cationic DNA-lipid complexes, which are efficient in vitro transfection agents (see, Felgner et al. *Nature* 337, 387–388 (1989); Felgner et al., *Proceedings of the National Academy of Sciences of the United States of America* 84, 7413–7417 (1987); Kao et al., *Cancer Gene Therapy* 3 250–256 (1996); Feigner et al., *Annals of the New York Academy of Sciences* 772, 126–139 (1995); Jarnagin et al., *Nucleic Acids Research* 20, 4205–4211 (1992)), are taken up via endocytosis.

This example describes a new approach for enhancing the interaction of liposomes with cells, a necessary step in the development of non-viral systems capable of intracellular delivery. The approach involves the insertion of novel cationic-PEG-lipids into pre-formed liposomes, leading to a cationic vesicle in which the positive charge involved in cell interaction is located some distance away from the vesicle surface. The process is illustrated in FIG. 16 for the insertion of a $CPL_4$ into sterically-stabilized LUVs composed of DOPE, the cationic lipid DODAC, and PEG-Cer-C20. This lipid composition was chosen for study for two reasons: first, it allows for efficient entrapment of plasmid DNA within small vesicular structures by virtue of the presence of positively charged DODAC (see, Wheeler et al. *Gene Therapy* 6, 271–281 (1999)), and thus has potential as a gene delivery system (see below). Secondly, this composition is representative of the many sterically-stabilized drug delivery systems which contain PEG-lipids. Insertion of CPLs leads to localization of positive charge above the surface PEG layer, thereby allowing electrostatic interactions between the CPLs and cell surfaces. This should lead to increased cellular interactions for both conventional- and PEG-containing liposomes.

The CPLs are conjugates of DSPE, a dansyl-lysine moiety, the hydrophilic polymer $PEG_{3400}$, and a mono- or multivalent cationic headgroup. The PEG functions as a spacer, separating the charged headgroup from the lipid anchor and vesicle surface. Incubation of a wide variety of neutral and cationic LUVs with micellar CPLs resulted in the incorporation of up to 6–7 mol % (relative to total vesicle lipid) of CPL in the outer vesicle monolayer (see tables in FIGS. 23 and 24). The insertion efficiency was quite high, with approximately 70–80% of added CPL incorporating into the LUVs (see tables in FIGS. 23 and 24). The most important factors influencing the CPL insertion levels were the incubation temperature FIG. 10) and initial CPL/lipid ratio (FIG. 11). The composition of the liposome was found to affect the final CPL levels to a lesser degree (see tables in FIGS. 23 and 24). Following insertion, the CPL-LUV could be efficiently separated from free CPL by gel exclusion chromatography. Similar insertion levels were obtained for all CPLs, with headgroup charges ranging from one to four charges per molecule. With this knowledge, vesicles could be prepared containing a desired level of CPL with reasonable accuracy.

High insertion levels (up to 7 mol %) could be achieved for vesicles containing as much as 10 mol % PEG-Cer-C20. It is possible that a portion of the PEG-Cer's are lost during the insertion process, as PEG-Cer's will exchange from vesicles during circulation. This may explain why the highest insertion levels are achieved with PEG-Cer-C8, which has the greatest propensity to exchange. However, analysis of LUVs and SPLPs containing PEG-Cer-C20 by HPLC before and after insertion of CPL4 reveal only a slight loss of PEG-Cer-C20 (from about 10 mol % to 8 mol %).

Figure 15:
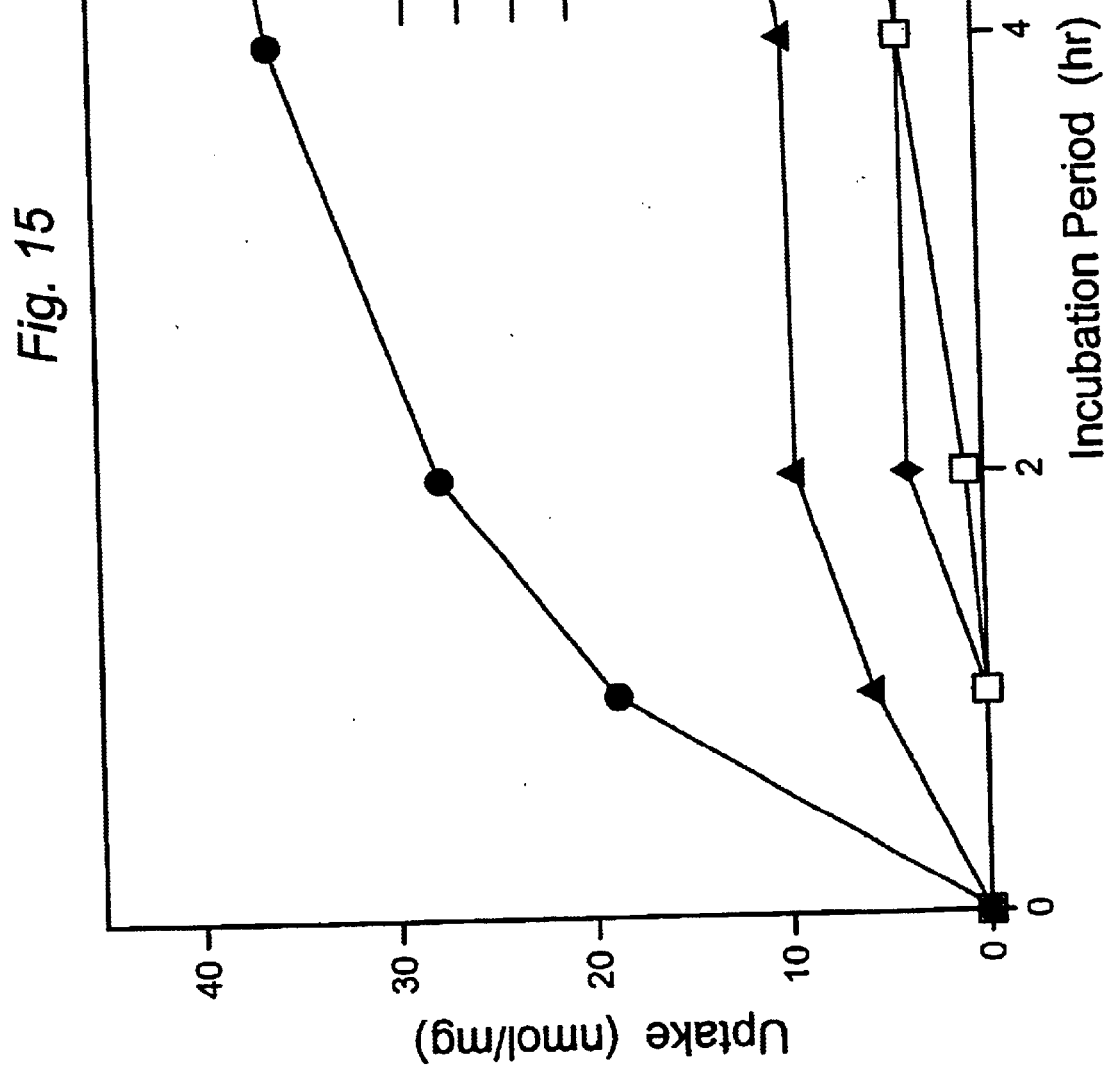
FIG. 15 illustrates the uptake of CPL-LUVs incubated in PBS/CMG on BHK cells. Approximately $10^5$ BHK cells were incubated with 20 nmol of DOPE/DODAC/PEGCerC20 (84/6/10) LUVs containing (1) no CPL, (2) 8% DSPE-CPL-D, (3) 7% DSPE-CPL-T1, and (4) 4% DSPE-CPL-Q5. Incubations were performed at 4° C. and 37° C., the former giving an estimate of cell binding, and the latter of binding and uptake. By taking the difference of the two values, an estimate of lipid uptake at 37° C. was obtained.

As shown in FIG. 15, cationic LUVs composed of DOPE/DODAC/PEG-Cer-C20 exhibit little uptake when incubated on BHK cells. Although positively charged vesicles exhibit enhanced binding to some cell lines, this can be attenuated by the presence of PEG on the liposome surface (see, Miller et al., Biochemistry 37, 12875–12883 (1998)). Clearly, for these systems, the presence of 6 mol % of positively charged DODAC leads to only low uptake levels after 6 hours. Incorporation of approximately 7 mol % of dicationic-CPL has little effect on uptake, which was only slightly improved in the presence of approx. 7 mol % tricationic-CPL. The best results were obtained with the CPL4b (at 4 mol %), which possessed 4 positive charges. At 6 hours incubation, a ten-fold increase in uptake was observed relative to the starting vesicles. Several points can be surmised from this data. The first is that the presence of positively charged groups at some distance from the LUV surface can lead to significant increases in cellular uptake. In this case, the positive charges of the CPL (PEG MW=3400) are located above the surface coating of PEG (MW=2000), and thus are available for interactions with cells. However, it is not total charge alone that plays a role in enhanced cell binding. The quantity of positive charge present for the $CPL_2$ and $CPL_{4b}$ samples is approximately equal, and yet the former shows little uptake compared to the latter. The $CPL_3$ sample has a greater positive charge than the $CPL_{4b}$ sample, and yet exhibits only ⅓ the uptake. It would appear that localization of a sufficient positive charge density at the distal end of the CPL molecule is an important parameter in ensuring interaction with cells. At least four charges seem to be required for efficient cell binding to occur.

The protocol described for insertion of CPL into conventional and sterically-stabilized CPL is ideal for demonstrating the methodology using in vitro applications. In both cases, the added positive charge is physically distant from the surface, and is available for interactions with cells. This is particularly important for polymer-coated vesicles that are designed for minimal interactions with serum proteins and cells such as macrophages. However, this system may not be ideal for in vivo applications, where it may be desirable to initially hide or screen the CPL charge to reduce clearance and allow accumulation of the vesicles at the tissue of choice. Thus, alternative embodiments employ shorter PEG spacer chains in the CPL, or longer PEG chains in the PEG-Cer molecules. The PEG-Cer molecules are known to exchange out of the particle during circulation see, Webb et al., Biochimica et Biophysica Acta 1372, 272–282 (1998)], which would leave the CPL exposed for cellular interactions.

As mentioned above, the cationic liposomes employed in the present study are composed of a fusogenic lipid (DOPE), a cationic lipid (DODAC), and a stabilizing lipid (PEG-Cer-C20), the latter of which imparts long-circulating properties to the vesicles. This lipid composition was modeled after a new class of lipid-based DNA carrier systems known as stabilized plasmid-lipid particles (SPLPs) see, Wheeler et al. Gene Therapy 6, 271–281 (1999)). SPLPs are small (70 nm) particles that encapsulate a single plasmid molecule. The presence of a PEG coating on the liposome surface imparts long-circulation properties as well as protecting the plasmid from degradation by serum nucleases. SPLPs thus represent the first carrier systems with real potential for systemic in vivo gene therapy applications. The approach described here greatly enhances the tranfection potency of these particles by increasing cellular binding and uptake, which leads to increased intracellular delivery of plasmids. The inclusion of CPL in conventional formulations (e.g., anticancer drugs) also leads to increased efficacy.

IV. Example IV

A. Overview

This example employs CPLs incorporated into stable plasmid-lipid articles (SPLPs) for in vitro transfection of cells.

Incubation of these particles on BHK cells for up to 8 hours resulted in an increase in uptake as the amount of inserted CPL increased from 2–4 mol %. Transfection of the SPLP system increased with the addition of CPL with 15 mM $CaCl_2$ in the transfection media. The SPLP alone showed very low transfection at both a 4 and a 9 hour transfection followed by 24 hour complete incubation in fresh media. The addition of 15 mM $CaCl_2$ final concentration in the media to the SPLPs, increased transfection on BHK cells by 10-fold at both time points. In the presence of 15 mM $CaCl_2$, SPLP+2%, 3% and 4% CPL transfect 2000- to 5000-times higher than that of the SPLP alone at both time points. The 4 mol % CPL shows the greatest increase in transfection: approximately 4500 times higher, followed by the 3% and then the 2% CPL samples. Therefore, the presence of the CPL, DSPE-Quad5 in the SPLP increased in both uptake and transfection to levels comparable to or above those achieved with the complexes.

B. Materials and Methods

1. Synthesis of the DSPE-Quad5: The dansylated DSPE-Quad5 (CPL) was prepared in our laboratory as described by Chen et al (2000).

2. Incorporation of DSPE-Quad5 Into SPLP: Inex Pharmaceuticals, Inc. supplied the SPLP. The incorporation of the CPL into the SPLP was performed by incubation of the CPL with the SPLP at 60° C. for 2–3 hours in HBS. The resulting mixture was then passed down a Sepharose CL-4B column equilibrated with HBS, 75 mM $CaCl_2$, pH 7.5 to remove the unincorporated CPL from the SPLP with the incorporated CPL. Fractions (1 mL) were collected and assayed for CPL (dansyl assay), phospholipid, and DNA (PicoGreen assay). The final samples were prepared to contain 2, 3, or 4 mol % of the CPL. The dansyl assay involved preparing a standard curve of 0.5 to 2.5 mol % of dansylated CPL in BBS and determining the concentration of the CPL in the sample. The phospholipid was extracted from the SPLP by extracting the lipid using the Bligh-Dyer extraction technique (Bligh & Dyer, 1952) and then performing a Fiske-Subarrow assay on the organic phase of the extraction. The PicoGreen assay was performed by comparing the sample in the presence of PicoGreen and Triton X-100 using a DNA standard curve. The final % insertion of the CPL was determined by dividing the CPL concentration by the lipid concentration.

The optimal time for insertion of the CPL into the SPLP was determined using SPLP prepared with 0.5 mol %

Rh-DSPE. 15 nmol of the dansylated CPL (DSPE-Quad5) was mixed with 200 nmol of the labeled SPLP and the sample was incubated at 60° C. for various time points (0.5, 1, 2, 3, and 4 hours). At these time points the sample was removed from the water bath and was passed down a Sepharose CL-4B column. The major fraction was collected from the column and the dansyl to rhodamine fluorescence ratios were measured. The parameters used for the rhodamine fluorescence were a $\lambda_{ex}$ of 560 nm and a $\lambda_{em}$ of 600 nm and for the dansyl fluorescence were a $\lambda_{ex}$ of 340 m and a $\lambda_{em}$ of 510 nm. The excitation and emission slit widths for both of these were 10 nm and 20 nm, respectively. By comparison of the dansyl/rhodamine ratio for the sample before the column to that after the column, the % insertion was determined at each time point.

3. QELS of CPL-SPLP: The diameter of these particles was determined using a Nicomp Particle Sizer.

4. Freeze-Fracture EM: Freeze-fracture EM was performed on the 2%, 3%, and 4% CPL samples by methods which will be described by K. Wong 5. Serum Stability of Particles: The stability of the DNA within these CPL-SPLP was determined by incubating the samples (25 μL), containing 6 μg of plasmid DNA (pLuc) for various time periods (0, 1, 2, and 4 hours) in 50% mouse serum (25 μL) at 37° C. At each time point, other than the zero time point, 11 μL of the mixture was removed, the volume was made up to 45 μL using water and the samples were placed on ice. The DNA was then extracted from the lipid using one volume of phenol:chloroform (1:1). Following a 20 min centrifugation in a microfuge, the top aqueous phase was removed. The zero time point was obtained by removing 5.5 μL of the sample prior to serum addition and performing the extraction. Twenty microliters of the aqueous phase was then mixed with 2 μL of loading buffer and the sample was run on a 1% agarose gel in TAE buffer. Following one hour, the gel was placed on a transilluminator and a photograph was taken.

6. Lipid Uptake Studies: For the uptake studies, $1 \times 10^5$ BHK cells were grown on 12 well plates overnight in 2 mL of complete media (DMEM+10% FBS) at 37° C. in 5% $CO_2$. Then 20 nmol of the 2, 3, and 4 mol % CPL-SPLP samples containing 0.5% rhodamine-DSPE were mixed with HBS+75 mM $CaCl_2$ to a final volume of 200 μL and this was added to the top of the cells followed by the addition of 800 μL of complete media. This was allowed to incubate on top of the cells for 2, 4, 6, and 8 hours at which time the cells were washed three times with PBS and were lysed with 600 μL of 0.1% Triton X-100 in PBS, pH 8.0. The rhodamine fluorescence of the lysate was then measured on a fluorometer using a $\lambda_{ex}$ of 560 nm and a $\lambda_{em}$ of 600 nm using slit widths of 10 and 20 nm, respectively. An emission filter of 430 nm was also used. A 1.0 mL microcuvette was used. The lipid uptake was determined by comparison of the fluorescence to that of a lipid standard (5 nmol). This value was then normalized to the amount of cells present by measuring the protein in 50 μL of the lysate using the BCA assay.

Fluorescence micrographs were taken on a Zeiss fluorescence microscope.

7. Transfection Studies: For the in vitro transfection studies, $5 \times 10^4$ BHK cells were plated in 24-well plates in complete media. These were incubated overnight at 37° C. in 5% $CO_2$. SPLP, SPLP+75 mM $CaCl_2$, DOPE:DODAC (1:1)/DNA complexes, and CPL-SPLP systems (2, 3, and 4 mol % CPL) containing 2.5 kg of DNA were made up to 100 μL using HBS or HBS+75 mM $CaCl_2$ and were placed on the cells. Then 400 μL of complete media was added to this. At 4 and 9 hours, the transfection media was removed and replaced with complete media containing penicillin and streptomycin for a complete 24 hour transfection. At the end of the transfection period, the cells were lysed with lysis buffer containing Triton X-100. Following this lysis, 10–20 μL of the lysated was transferred to a 96-well luminescence plate. The luminescence of the samples on the plate were measured using a Luciferase reaction kit and a plate luminometer. The luciferase activity was determined by using a luciferase standard curve and was normalized for the number of cells by measuring the protein with the BCA assay on 10–20 μL of the lysated.

C. Results and Discussion

Figure 18A:
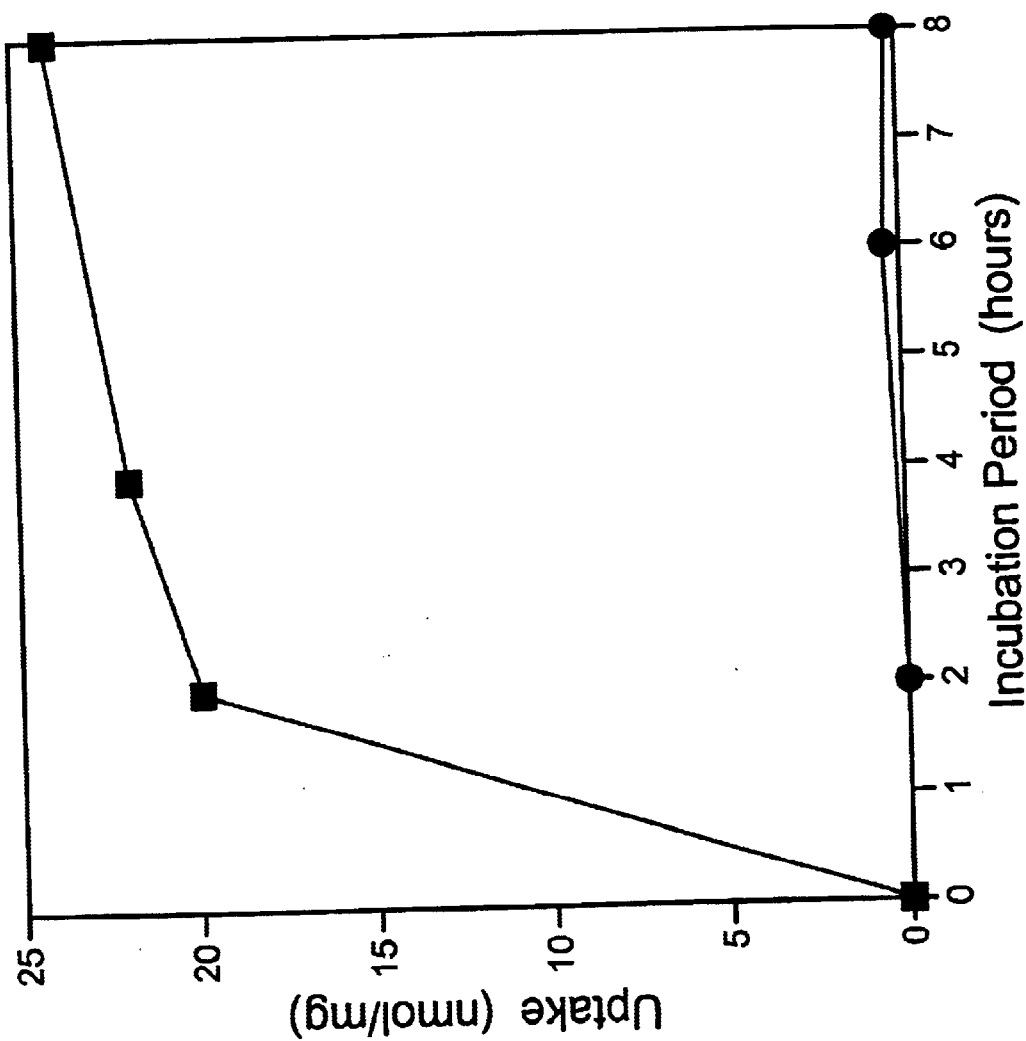
FIG. 18A illustrates a time-course for the uptake of SPLP system (●) compared to DOPE:DODAC (1:1) liposomes complexed to pLuc (■) on BHK cells. Lipid concentration was 20 μM.
Figure 18B:
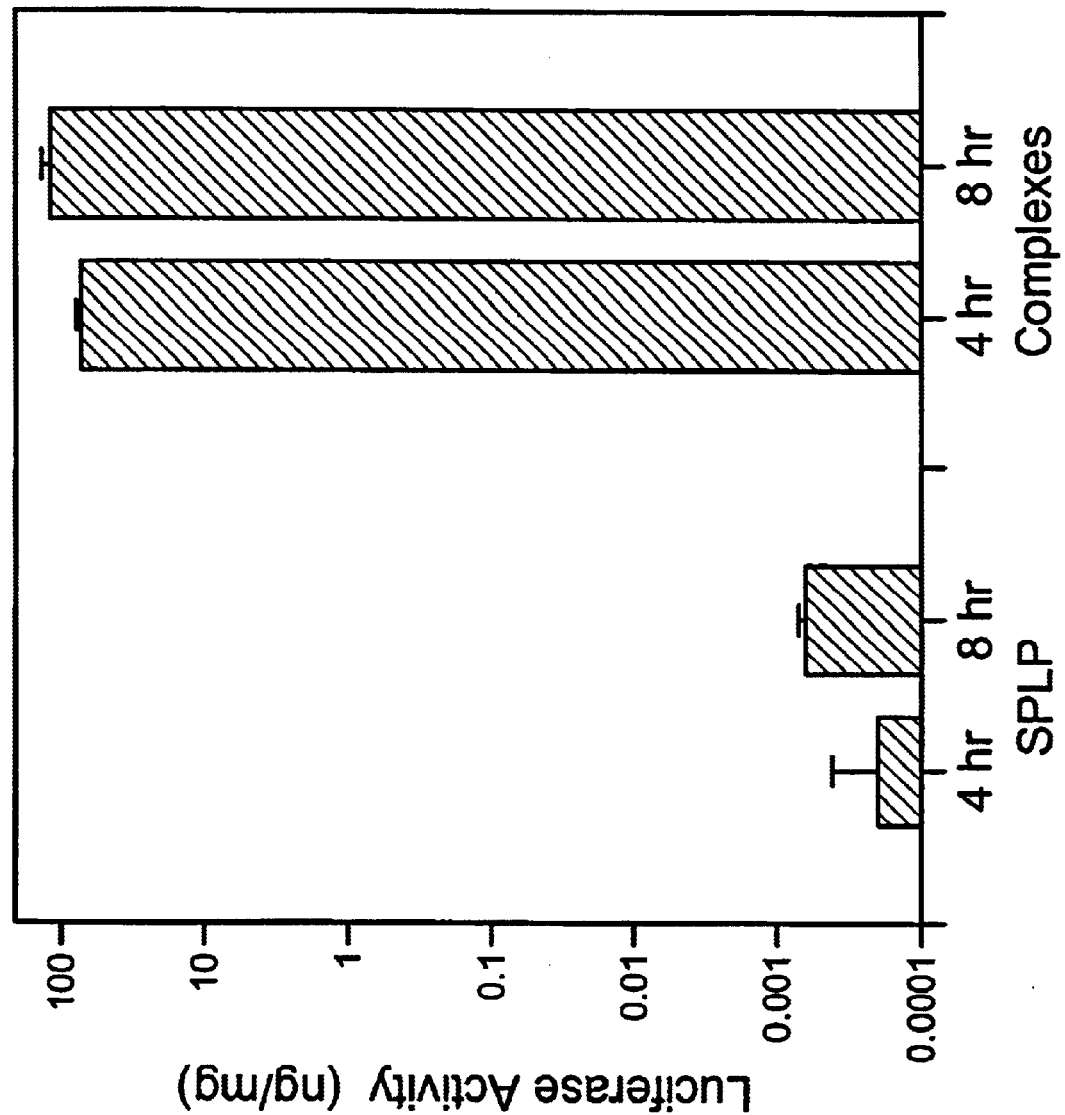
FIG. 18B illustrates transfection efficiencies of 1.5 μg/mL pLuc obtained using the SPLP system compared to those obtained using complexes after 4 hour (■) or 8 hour (■) incubations.

FIGS. 18A and B show that the uptake and transfection of the SPLP system is on the order of $10^5$ times lower than complexes.

Figure 16A:
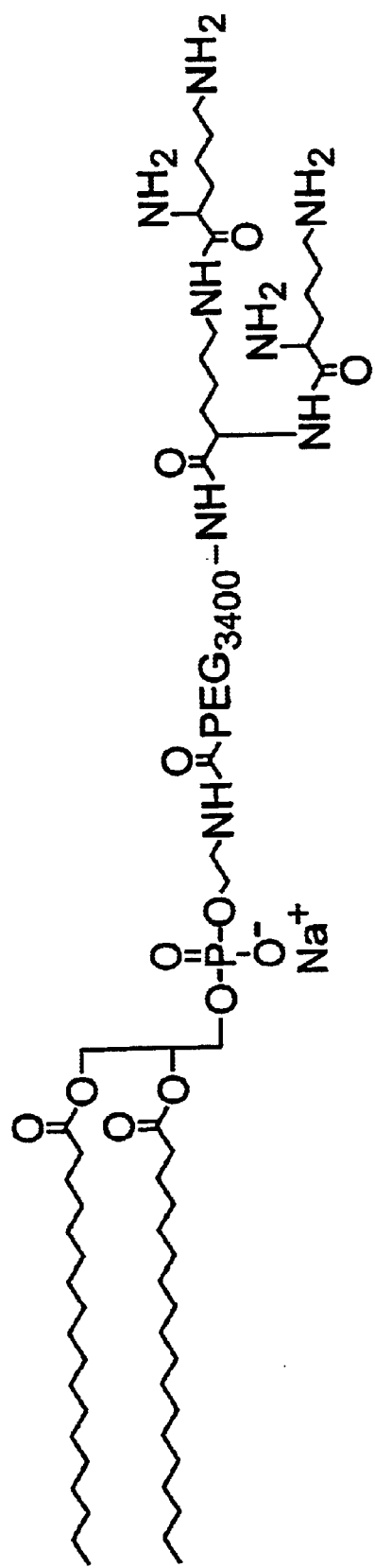
FIG. 16 Panel A illustrates a structure of the $CPL_4$. Panel B illustrates a protocol for the insertion of $CPL_4$ into the SPLP system.

The CPL, DSPE-Quad5, will be used in the following studies. Its structure is shown in FIG. 16A. This molecule possesses four positive charges at the end of a $PEG_{3400}$ molecule, which has been covalently attached to the lipid DSPE. The incorporation of this CPL into empty liposomes of the same composition as the SPLP has been described previously in the above examples.

Figure 16B:
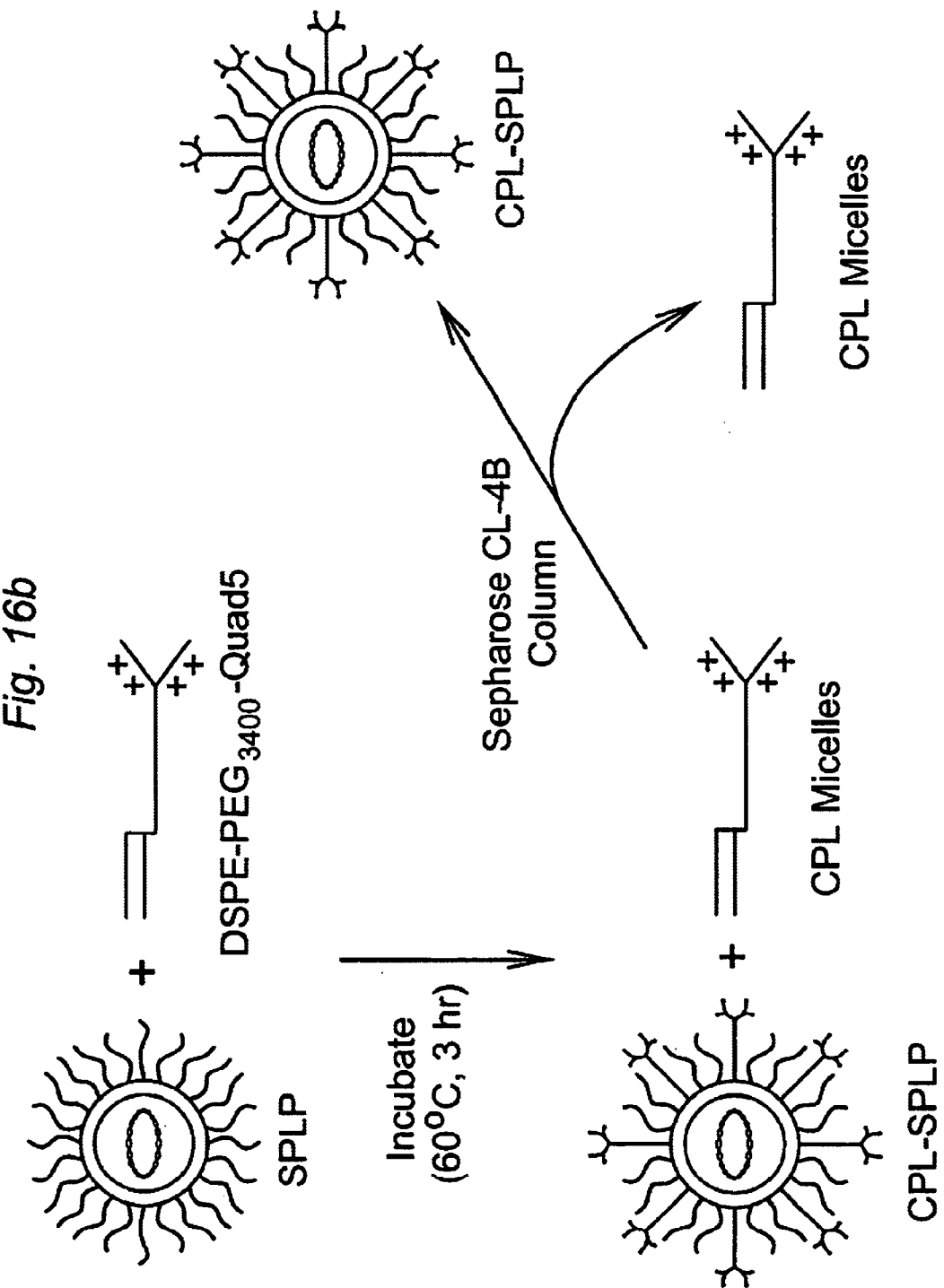

The incorporation of the CPL into the SPLP involves only a few steps. These steps are shown in FIG. 16B.

Figure 19A:
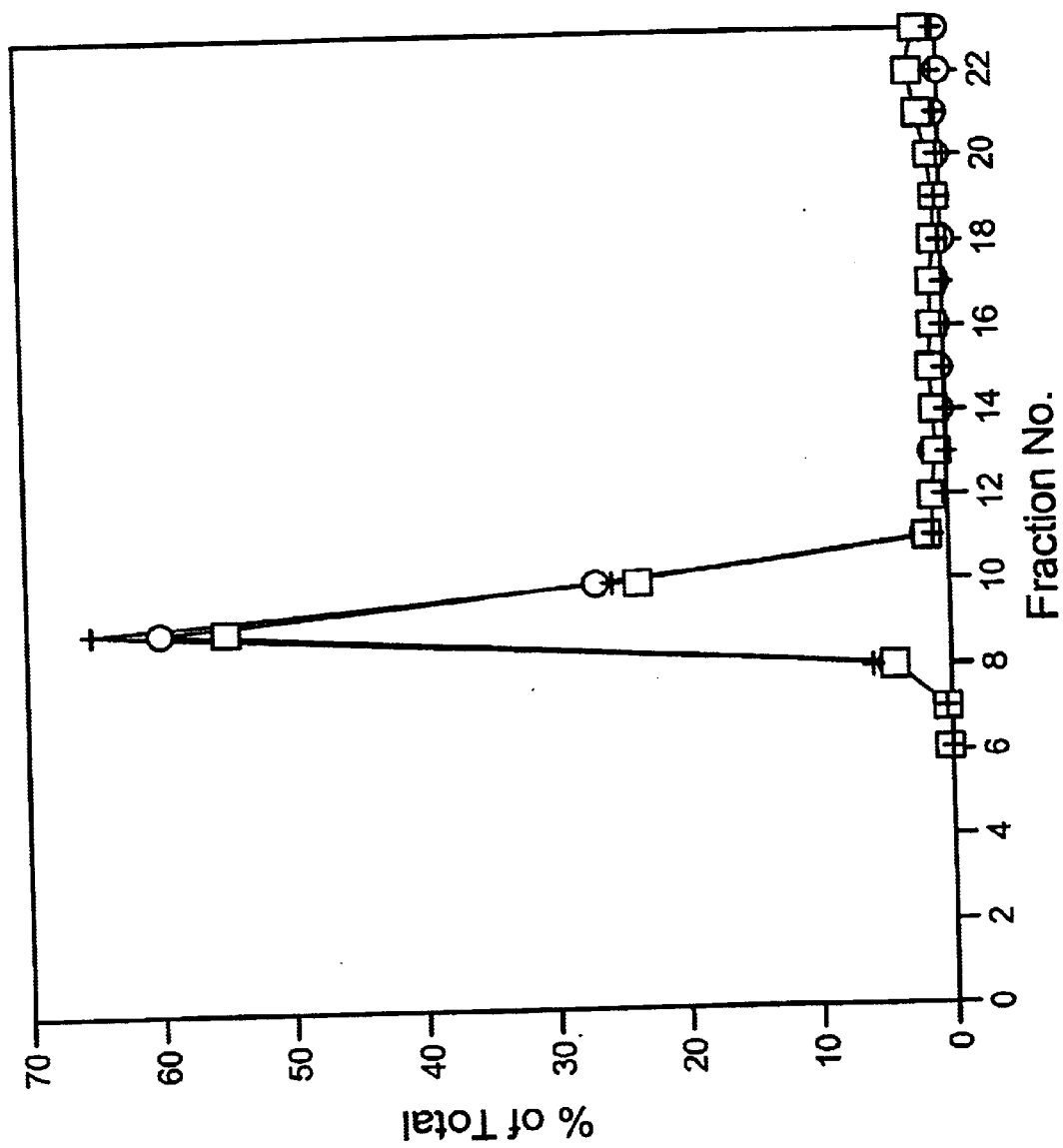
FIGS. 19A–19B illustrate a column profile, following insertion of 3.5 mol %$_{initial}$(3 mol %$_{final}$) $CPL_4$ into SPLP, for the separation of CPL-SPLP from free CPL. Profiles for lipid (●), CPL (□), and DNA (◇) with respect to the total amount applied to a Sepharose CL-4B column are shown.
Figure 19B:
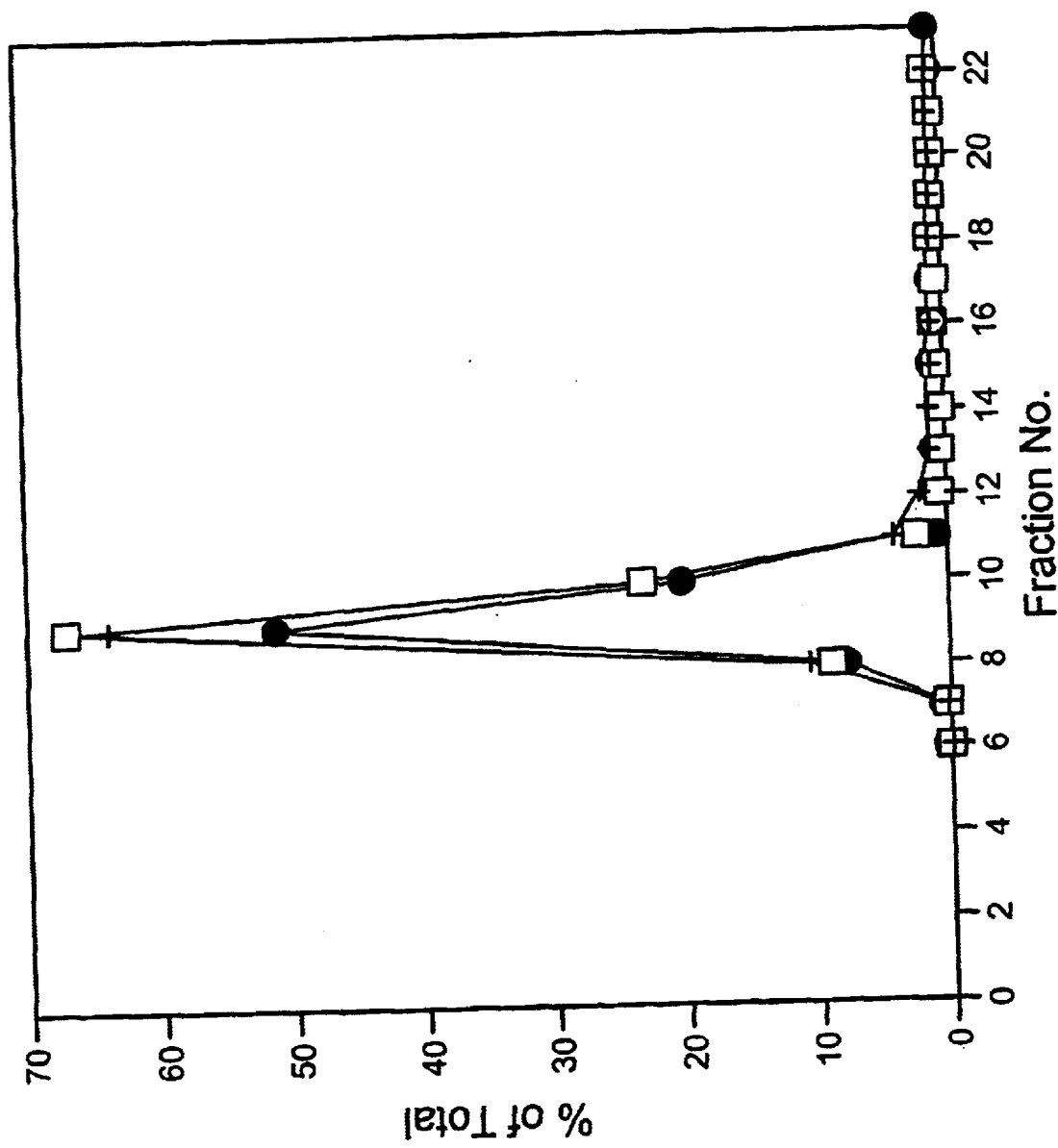

The DSPE-Quad5 was incorporated into SPLPs containing DOPE:PEG-CerC20:DODAC (84:10:6) at various concentrations of the CPL (from 2–4 mol %). The incorporation efficiencies for the various CPL percentages were between 70 and 80% of the initial. In order to separate the SPLPs possessing the CPL from the unincorporated CPL, gel filtration chromatography was employed. A typical column profile for the 3% DSPE-Quad5 is shown in FIG. 19A. The CPL, lipid, and DNA all eluted from the column at the same time in a single peak. There was however a small amount of unincorporated CPL that eluted at a later stage. To show that the incorporated CPL remains incorporated, the sample is re-eluted from the column (FIG. 19A). As it can be seen in FIG. 19B, no CPL is eluted in the later fractions of the column indicating that the CPL remains associated with the lipid.

Figure 20:
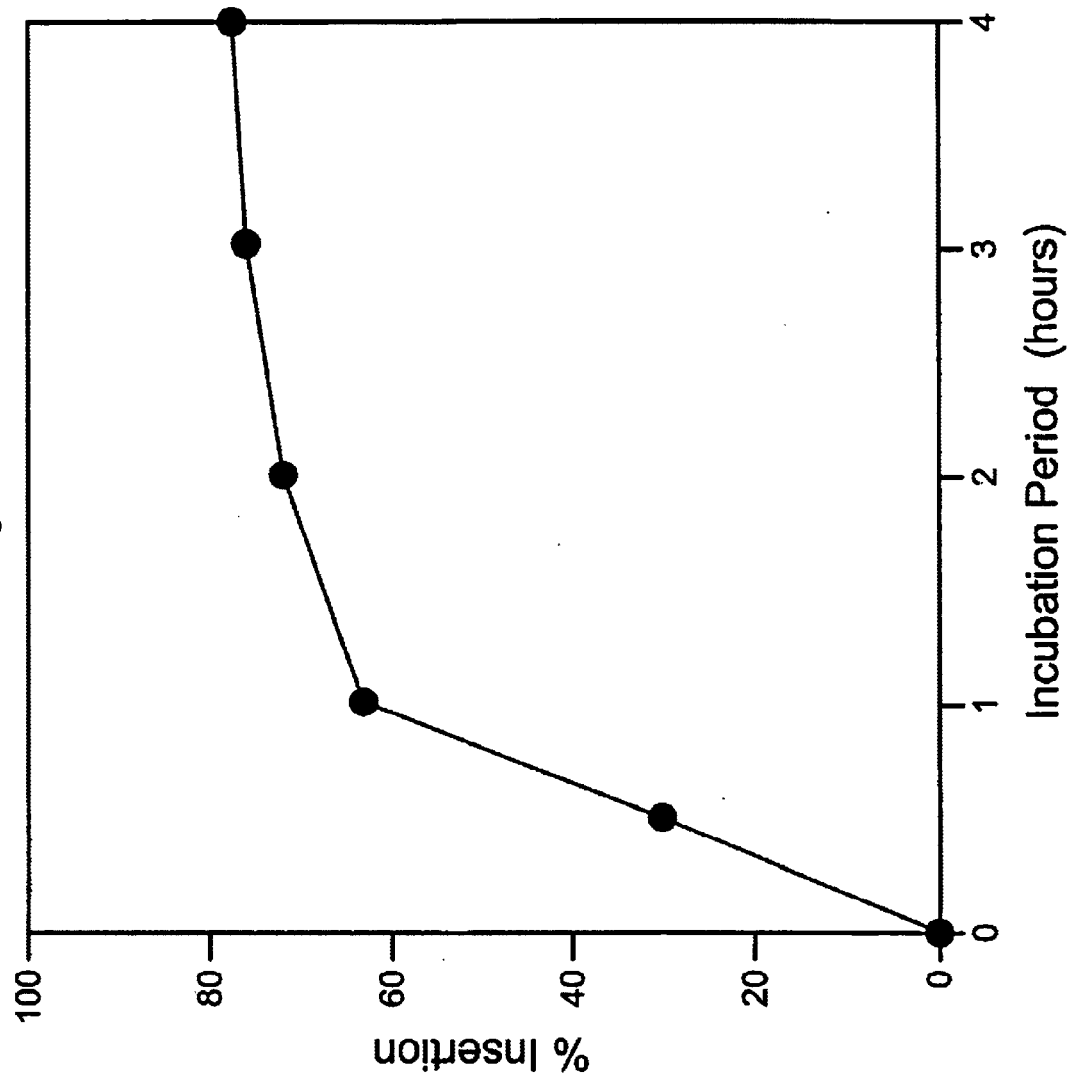
FIG. 20 illustrates a time course for the insertion of $CPL_4$ (15 nmol) into SPLP (200 nmol).

To determine the optimal incubation period for the insertion of the CPL, a time course at 60° C. was performed (FIG. 20). From this figure, it can be determined that the optimal insertion occurs between 2 and 3 hours.

The diameter of these particles containing the CPL was determined by QELS to be 125 mn compared to the SPLP, which had a diameter of 109 nm. To observe the structure of these particles compared to the SPLP in the absence of the CPL, freeze-fracture EM was performed.

The serum stability of the SPLP in the presence and absence of various amounts of the CPL was assayed (data not shown). Incubating free DNA with 50% mouse serum for only 1 hour results in its complete degradation. The serum stability of the CPL-SPLPs was similar to that for the SPLP system. This indicates that the DNA in the CPL-SPLP is as protected as that in the SPLP system without CPL.

Figure 21:
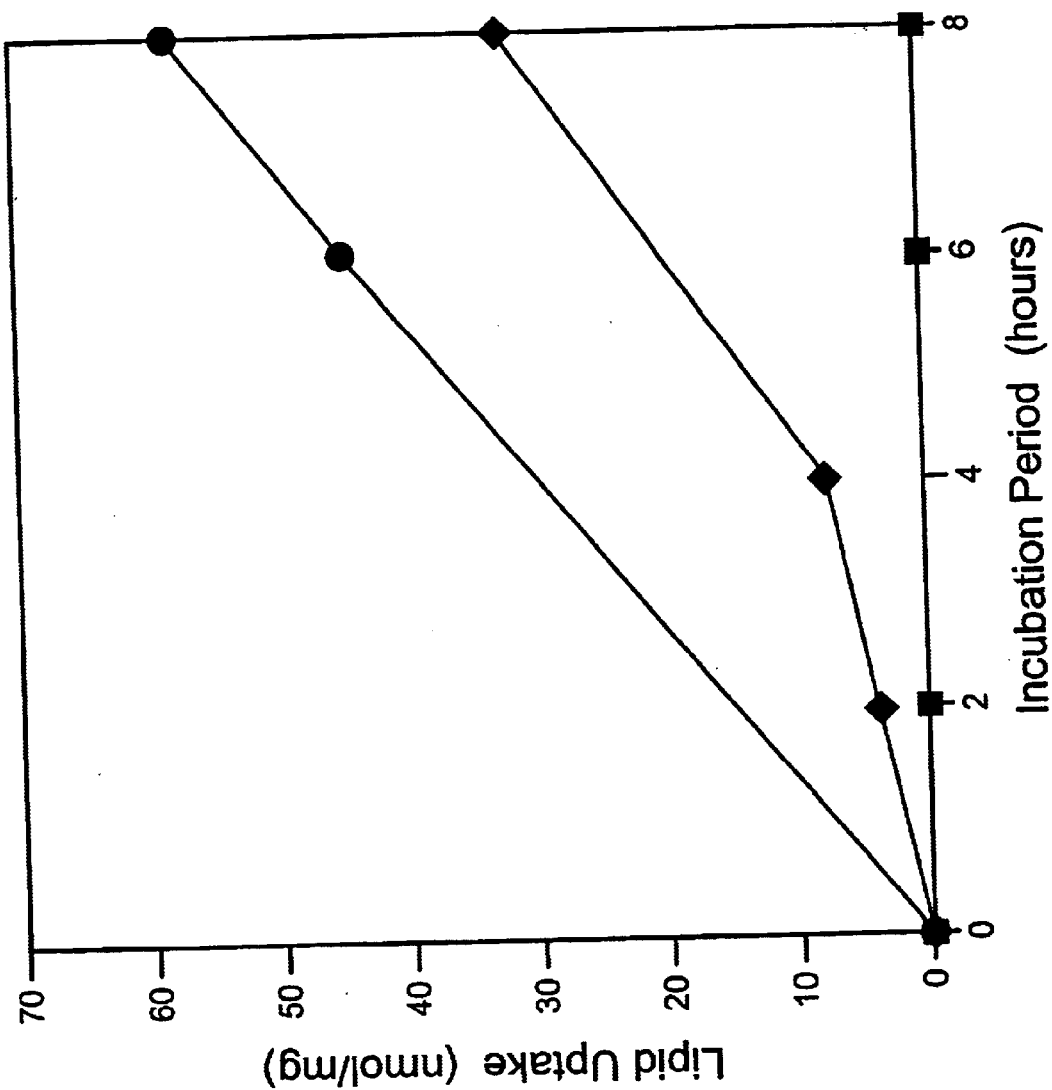
FIG. 21 illustrates a time course for the uptake of 20 μM of SPLP possessing 0% (■), 3% (◇), or 4% (●) $CPL_4$ in BHK cells.
Figure 22:
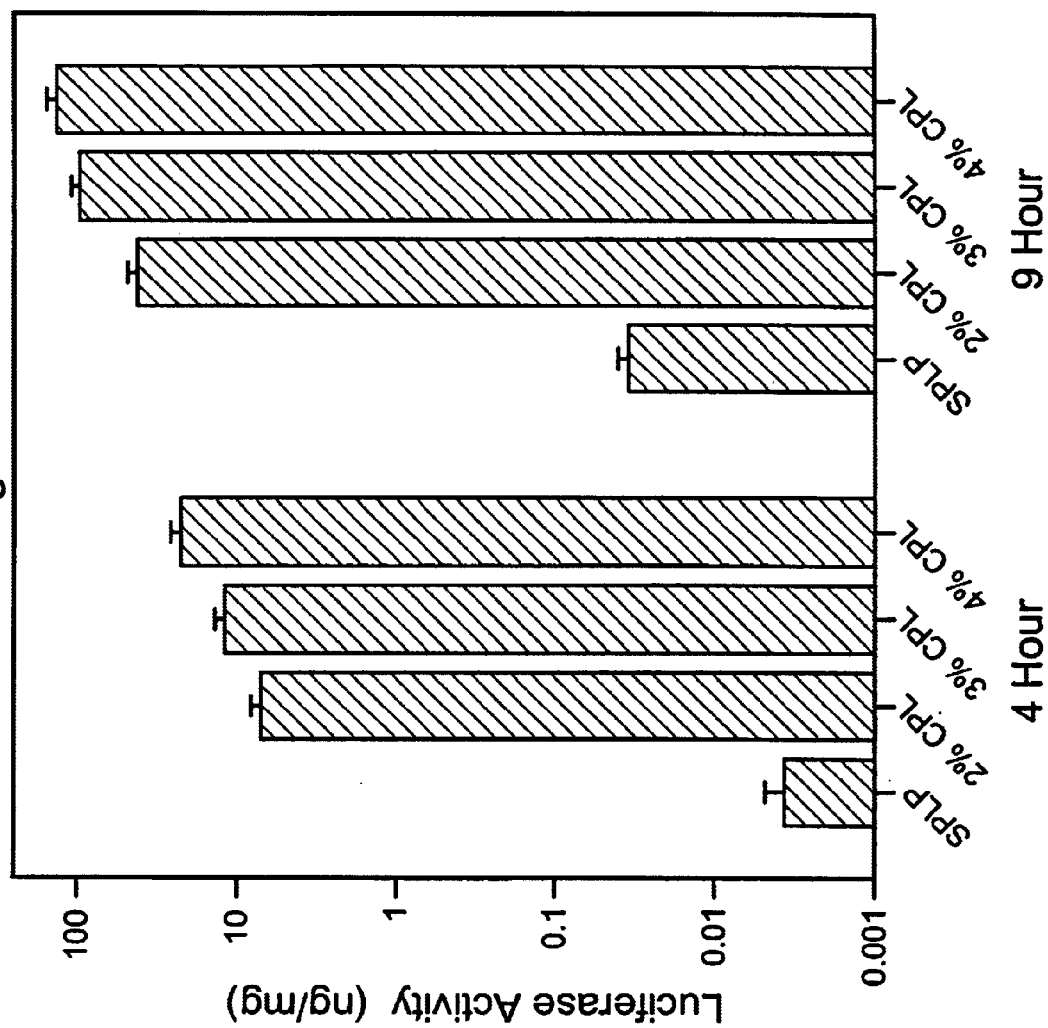
FIG. 22 illustrates transfection of BHK cells by SPLP (2.5 μg/mL pLuc) following insertion of various mol % of the $CPL_4$ compared to SPLP alone (0% CPL). Transfections were carried out by incubating the samples on top of the cells for 4 or 9 hours and replacing with complete media for a complete 24 hours incubation (see also FIG. 33).
Figure 25A:
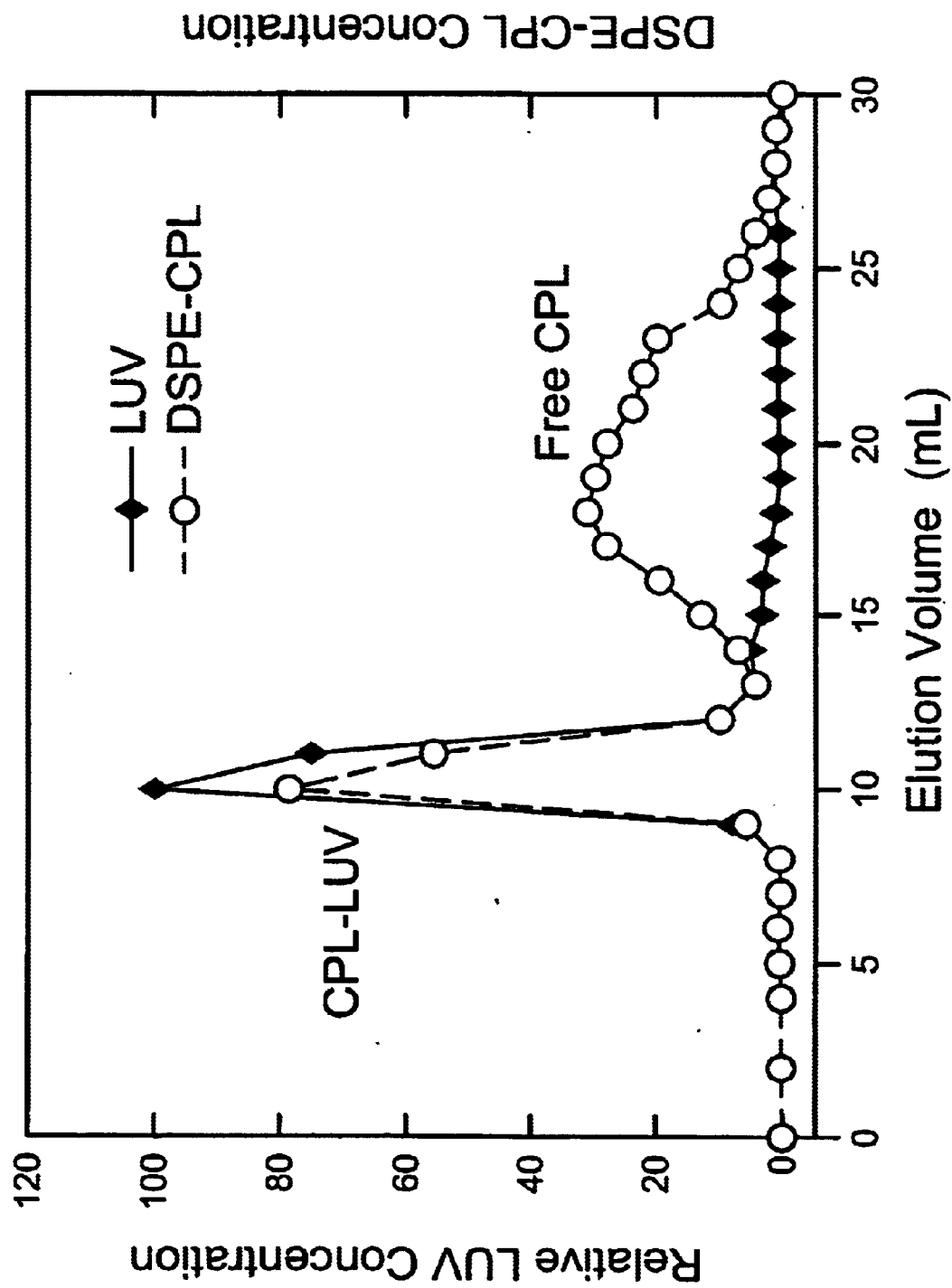
FIGS. 25A–25B illustrate the post-insertion method for preparation of CPL-containing liposomes. The preformed liposomes were made of DSPC/Chol (55:45, mol:mol). The CPL was incubated with the preformed liposomes at 60° C. for 2 hour. Panel A illustrates separation of free CPL and CPL-LUVs by gel filtration after post-insertion. Panel B illustrates elution of fraction 10 (Panel A) on a Sepharose CL-4B column.
Figure 25B:
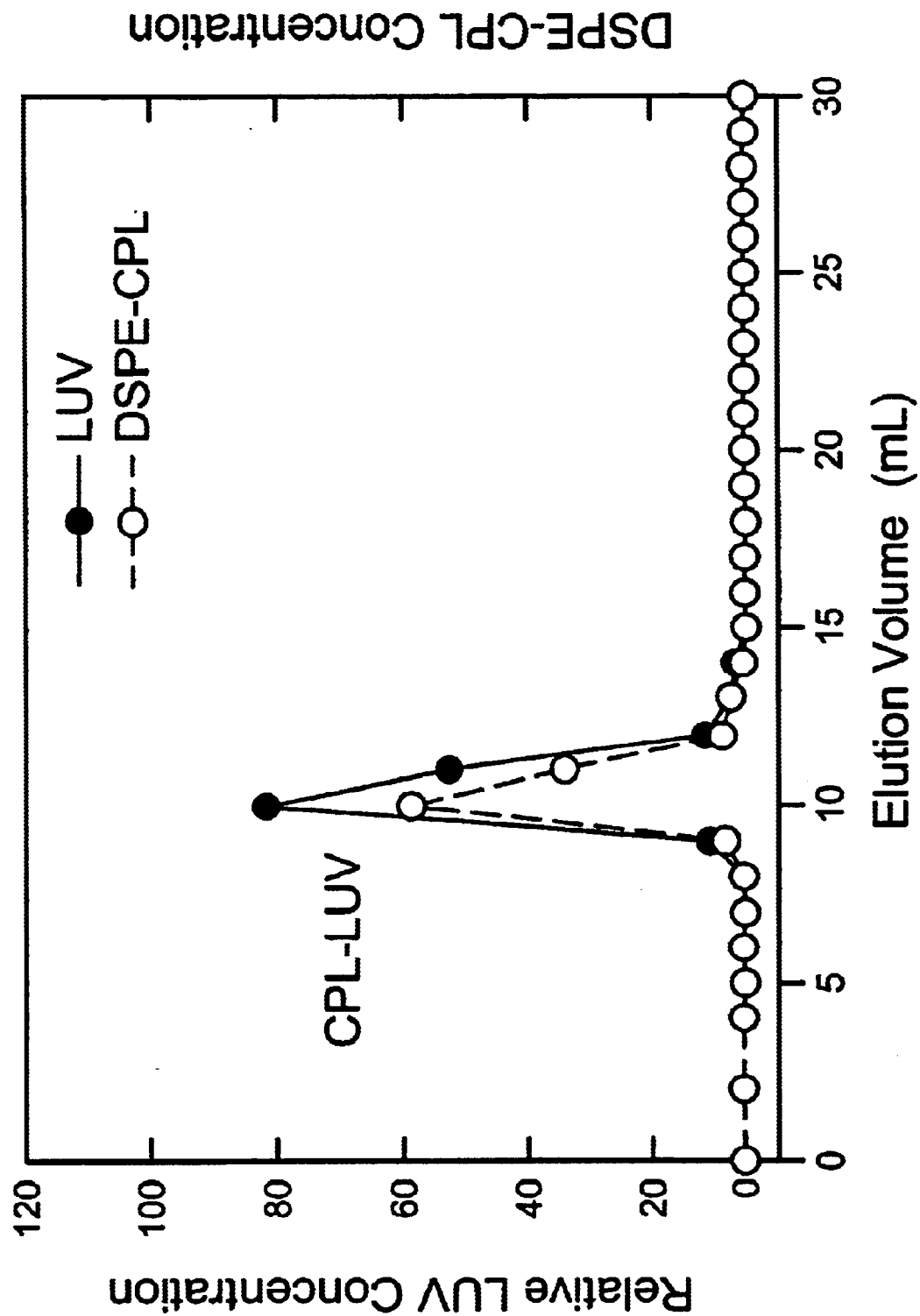

The major objective of this study is to increase both the uptake and transfection of the SPLP system using CPLS. FIG. 21 shows the time course for the uptake of rhodamine labeled SPLP in the presence (2, 3, or 4 mol %) and absence of the DSPE-Quad5 (0%). The uptake of the 4% system is higher than the 3% system, which is higher than the 2% system, and all three are much higher than the system without CPL. FIG. 22 shows 4 h and 9 h time points of the same formulations.

V. Example V

This example illustrates the incorporation of a CPL into a Stabilized Antisense-Lipid Particle ("SALP").

A. Materials and Results

Distearoylphosphatidylcholine (DSPC), was purchased from Northern Lipids (Vancouver, Canada). 1,2-dioleoyloxy-3-dimethylammoniumpropane (DODAP or AL-1) was synthesized by Dr. Steven Ansell (Inex Pharmaceuticals) or, alternatively, was purchased from Avanti Polar Lipids. Cholesterol was purchased from Sigma Chemical Company (St. Louis, Mo., USA). PEG-ceramides were synthesized by Dr. Zhao Wang at Inex Pharmaceuticals Corp. using procedures described in PCT WO 96/40964, incorporated herein by reference. [$^3$H] or [$^{14}$C]-CHE was purchased from NEN (Boston, Mass., USA). All lipids were>99% pure. Ethanol (95%), methanol, chloroform, citric acid, HEPES and NaCl were all purchased from commercial suppliers. Lipid stock solutions were prepared in 95% ethanol at 20 mg/mL (PEG-Ceramides were prepared at 50 mg/mL).

SALPs are first prepared according to the methods set out in PCT Patent Application No. WO 98/51278, published 19 Nov. 1998, and incorporated herein by reference. See also, J. J. Wheeler et al., (1999), *Gene Therapy*, 6, 271–281. Briefly, a 16mer of [3H]-phosphorothioate oligodeoxynucleotide Inx-6295 (human c-myc) having sequence 5' T AAC GTT GAG GGG CAT 3' (SEQ ID. No: 1) (in 300 mM citrate buffer, pH 3.80) was warmed to 65° C. and the lipids (in ethanol) were slowly added, mixing constantly (DSPC:CHOL:DODAP:PEG-CerC14; 25:45:20:10, molar ratio). The resulting volume of the mixture was 1.0 mL and contained 13 mmol total lipid, 2 mg of antisense oligodeoxynucleotide, and 38% ethanol, vol/vol. The antisense-lipid mixture was subjected to 5 cycles of freezing (liquid nitrogen) and thawing (65° C.), and subsequently was passed 10× through three stacked 100 nm filters (Poretics) using a pressurized extruder apparatus with a thermobarrel attachment (Lipex Biomembranes). The temperature and pressure during extrusion were 65° C. and 300–400 psi (nitrogen), respectively. The extruded preparation was diluted with 1.0 mL of 300 mM citric acid, pH 3.8, reducing the ethanol content to 20%. The extruded sample was dialyzed (12000–14000 MW cutoff, SpectraPor) against several liters of 300 mM citrate buffer, pH 3.8 for 3–4 hours to remove the excess ethanol. The sample was subsequently dialyzed against HEPES-buffered saline (HBS), pH 7.5, for 12–18 hours to neutralize the DODAP and release any antisense that was associated with the surface of the vesicles. Encapsulation was assessed either by analyzing the pre-column and post-column ratios of [$^3$H]-antisense and [$^{14}$C]-lipid or by determining the total pre-column and post-column [$^3$H]-antisense and [$^{14}$C]-lipid radioactivity.

CPL is incorporated after the SALPs are prepared. Approximately 5 μmol SALP were mixed with 3–10 mol % CPL (i.e., 0.15–0.5 μmol CPL). CPL were stored as micellar solutions in HBS, or in methanol. When CPL was added in methanol, the final methanol concentration of 3–4%. The mixtures were incubated overnight at room temperature or at 40° C. Unincorporated CPL was removed from the SALP preparation by column separation (Sepharose CL-4B equilibrated with HBS, 75 mM $CaCL_2$ at pH 7.5). Incorporation efficiency was between 34 and 60%. It is anticipated that other organic solvents may improve incorporation efficiency.

VI. Example VI

A. General Overview

In the present example, distal positively charged cationic poly(ethylene glycol) lipid conjugates (CPL) were synthesized and assessed for their efficacy at enhancing the cellular uptake of CPL-incorporated liposomes. It was confirmed that distal charged polymer conjugates bound to a liposome surface enhanced liposome uptake in mammalian cells in vitro.

B. Methods

Determination of the Critical Micelle Concentration (CMC)

The CMCs of the CPLs were determined using the NPN assay as previously reported by Brito and Vaz (see, Brito, R. M. M., and Vaz, W. L. C. (1986) Determination of the critical micelle concentration of surfactants using the fluorescent probe N-phenyl-1-naphthylamine. *Anal. Biochem.* 152, 250–255.). A series of different concentrations of CPLs were prepared in HBS buffer (25 mM Hepes, 150 mM NaCl, pH 7.4). 5 μM of NPN (from a stock NPN solution in 95% ethanol) was added into the above CPL solutions. After incubation of the mixtures at room temperature for 30 min, the fluorescence intensities at $\lambda_{em}$=410 nm using $\lambda_{ex}$=356 nm on a Perkin Elmer LS 50 Luminescence Spectrometer.

C. Results

Uptake Enhancement of CPL-LUVs in vitro. Cellular Uptake of Conventional CPL-liposomes.

Figure 6:
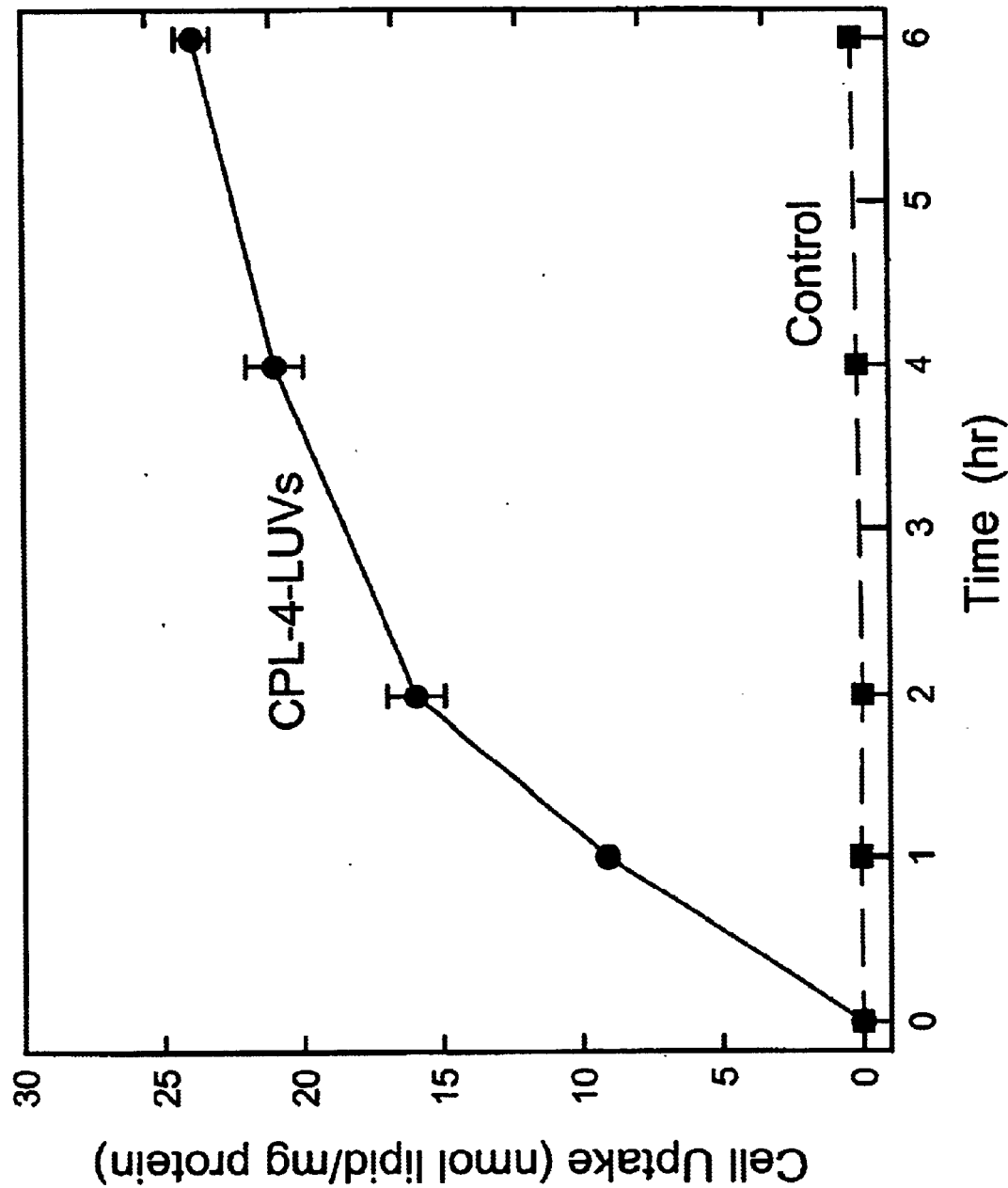
FIG. 6 illustrates cellular uptake of CPL-4-LUVs in BHK cells in DMEM (with 10% FBS). The control used LUVs (DSPC/Chol, 60:40). CPL-4-LUVs (DSPC/Ch/DSPE-CPL-4, 55:40:5), which were prepared by extrusion as described herein.
Figure 7:
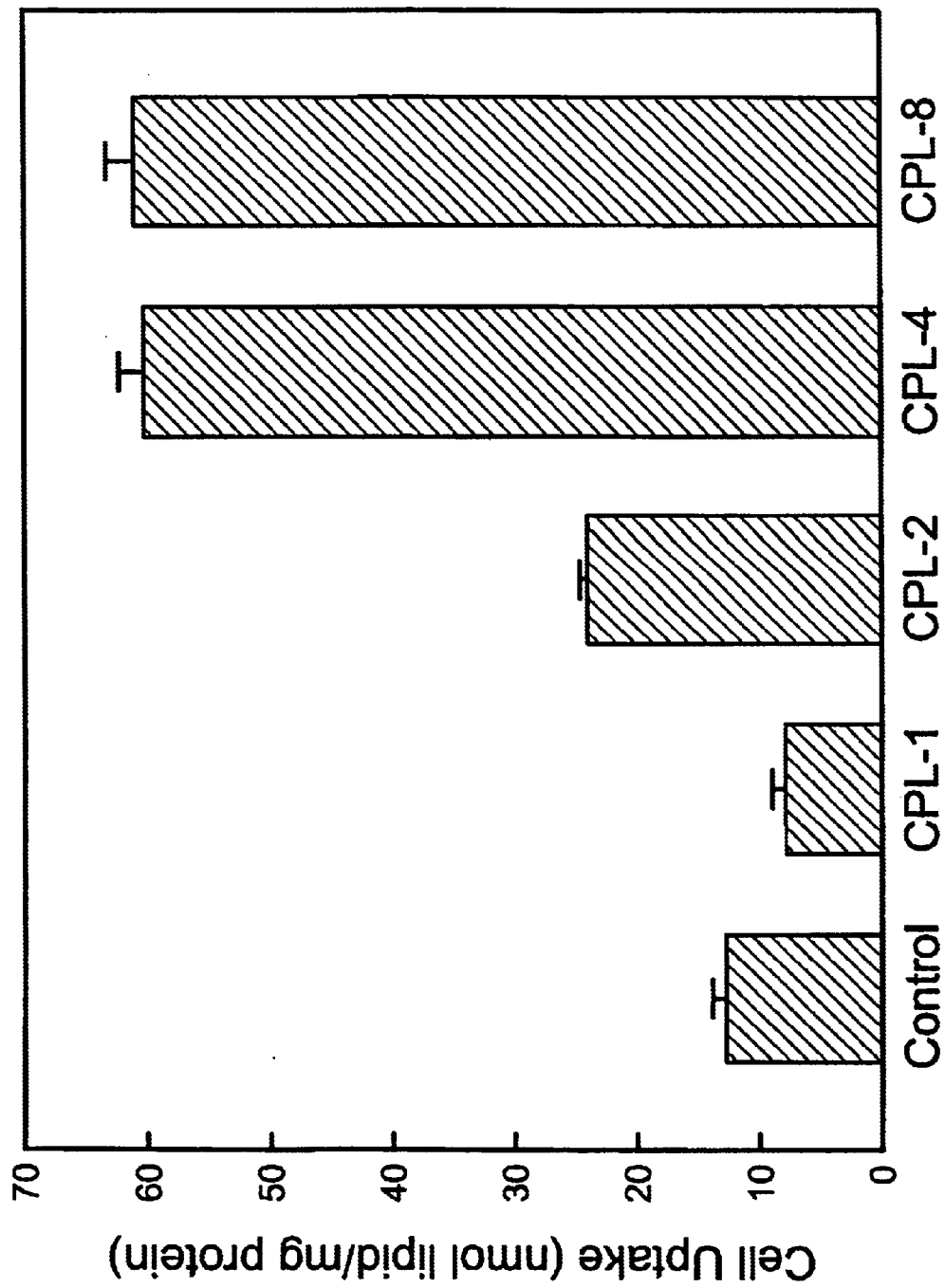
FIG. 7 illustrates a cellular uptake of CPL-liposomes in BHK cells in PBS-CMG after 4 hr incubation. LUVs (DSPC/Chol, 60:40) and CPL-LUVs (DSPC/Chol/DSPE-CPL, 55:40:5) were prepared by extrusion as described herein.
Figure 26:
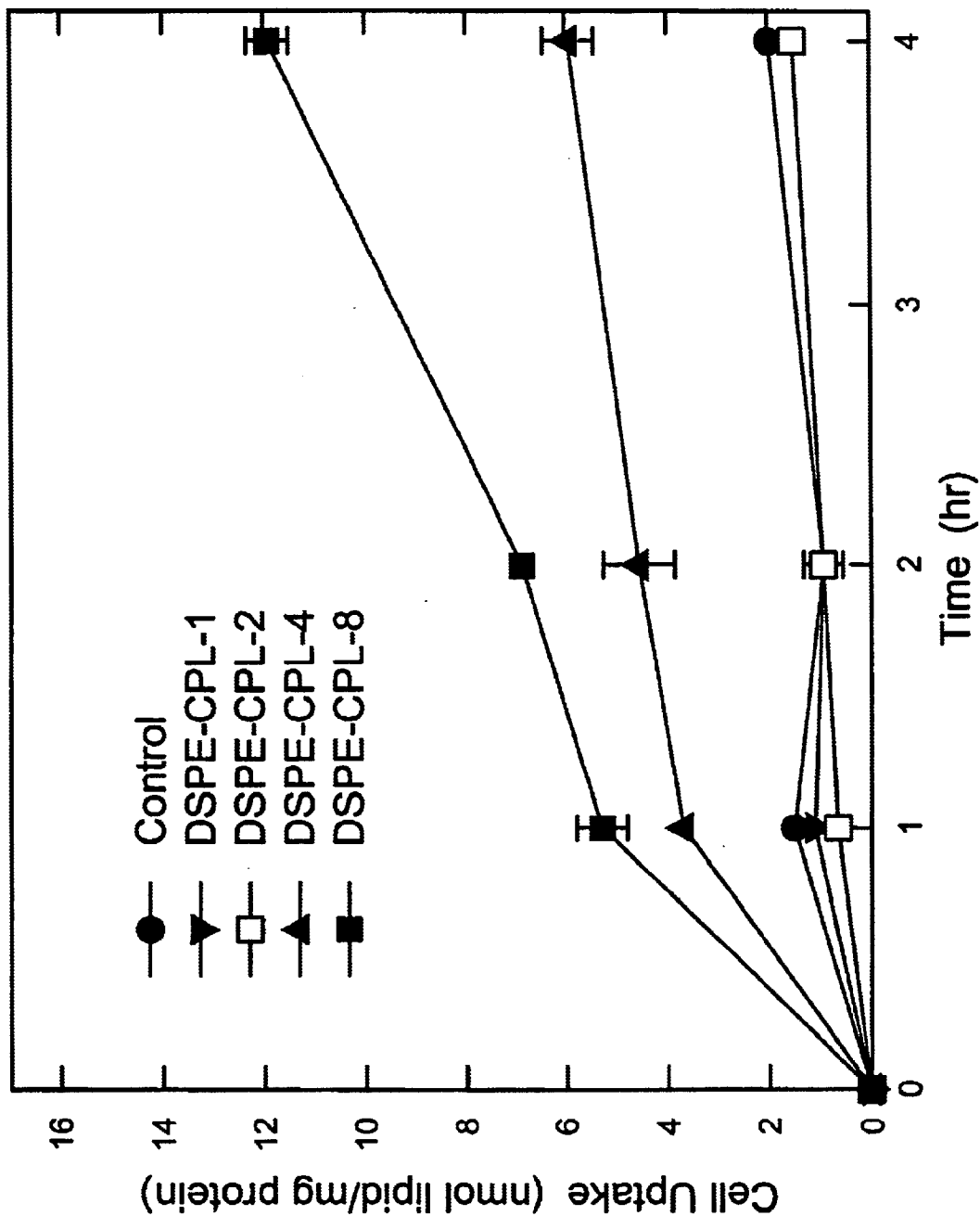
FIG. 26 illustrates cellular uptake of the stealth liposomes containing DSPE-CPLs in BHK cells in DMEM (10% FBS). Control LUVs (DSPC/Chol/PEG-PE, 56:40:4) and CPL-LUVs (DSPC/Chol/PEG-PE/CPL, 55.5:40:2:2) were prepared by extrusion as described herein.
Figure 27:
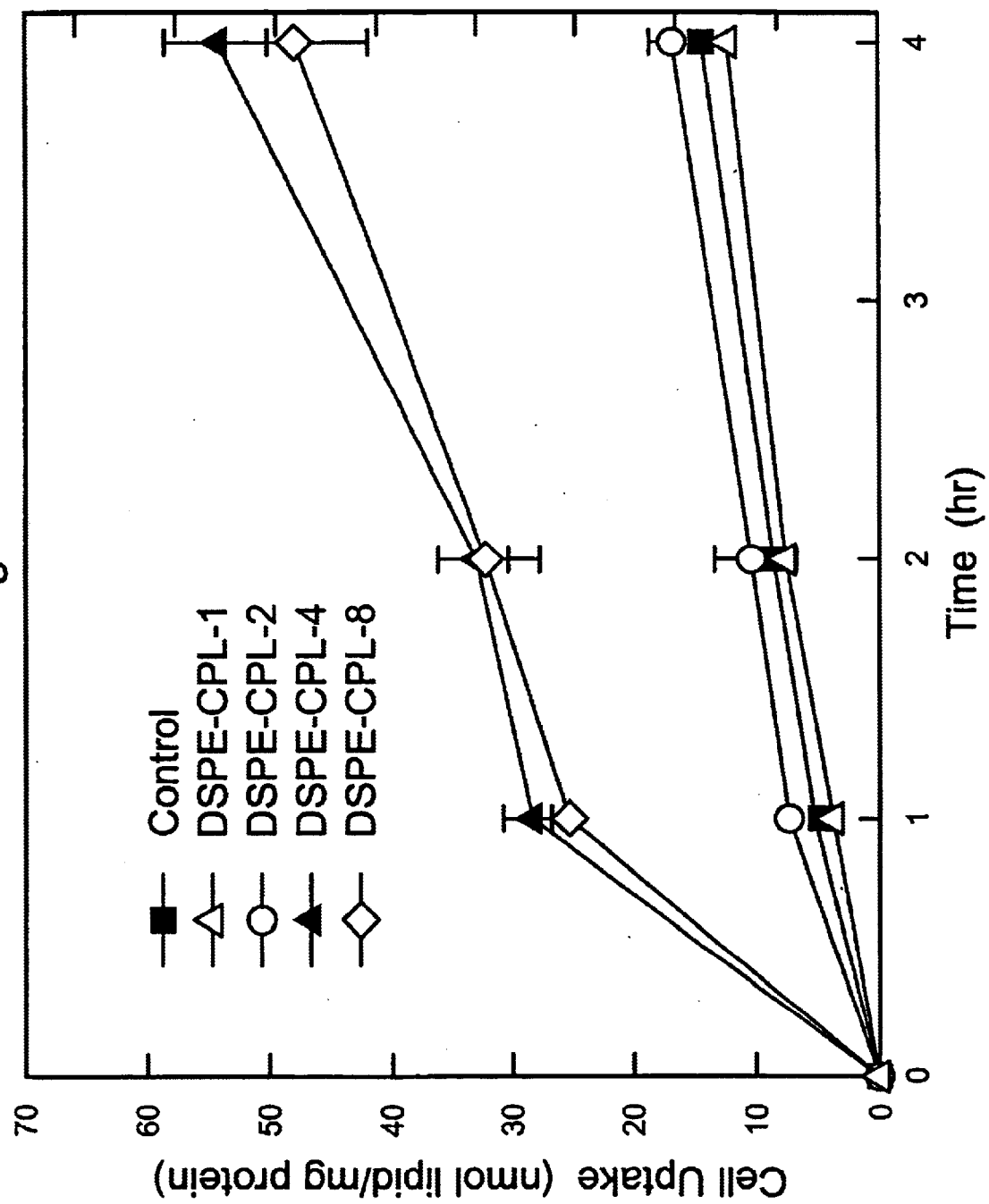
FIG. 27 illustrates cellular uptake of stealth liposomes containing DSPE-CPLs in BHK cells in PBS-CMG. Control LUVs (DSPC/Chol/PEG-PE, 56:40:4) and CPL-LUVs (DSPC/Chol/PEG-PE/CPL, 55.5:40:2:2) were prepared by extrusion as described herein.
Figure 28A:
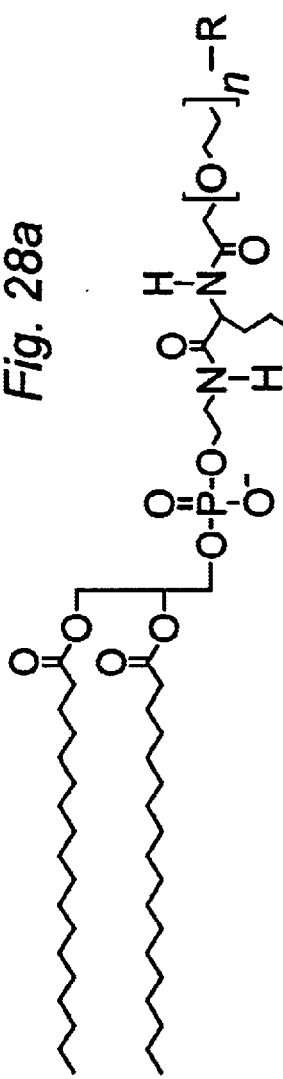
FIGS. 28 Panels A–D show chemical structures of various CPLs. Note that $CPL_4$ (Panel A) is identical to $CPL_{4b}$ (Panel B).
Figure 28A:
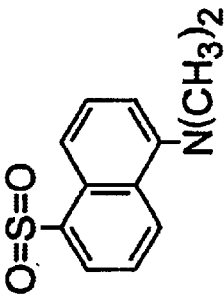
Figure 28A:
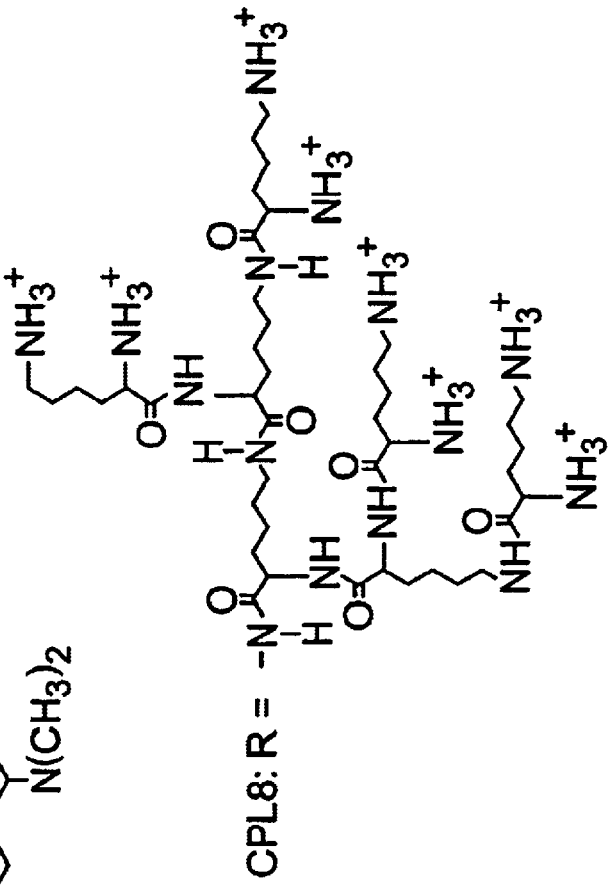
Figure 28B:
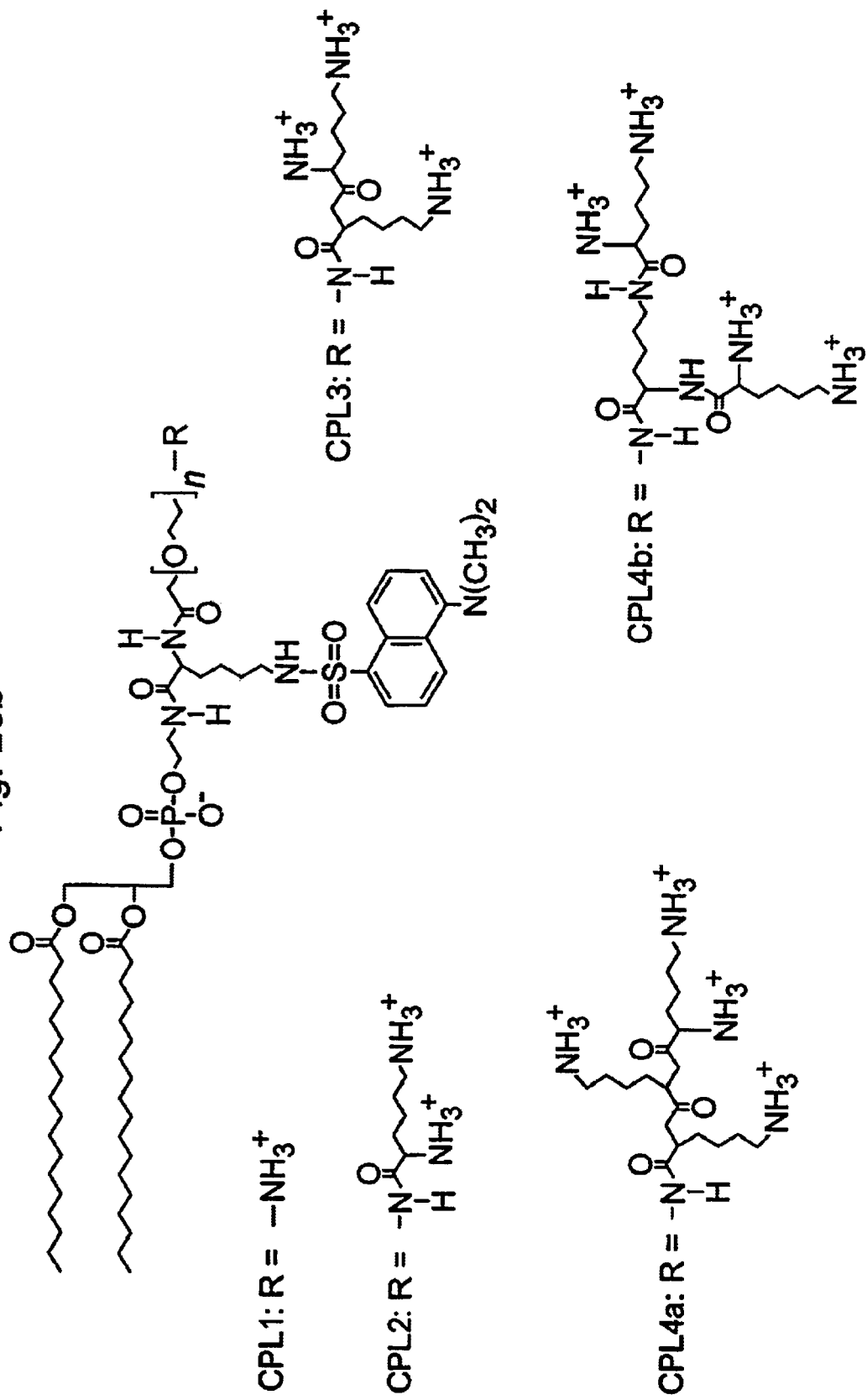
Figure 28C:
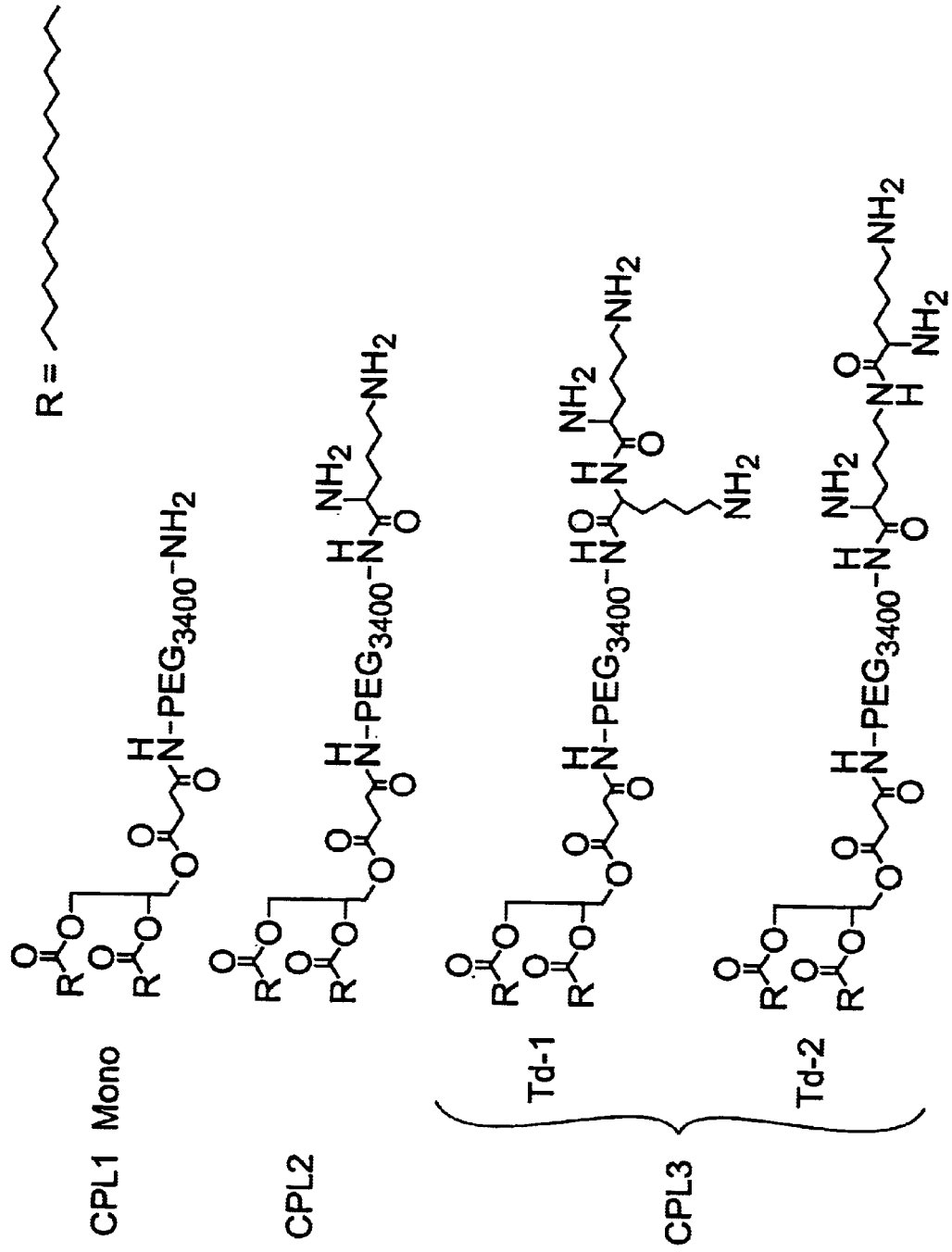
Figure 28D:
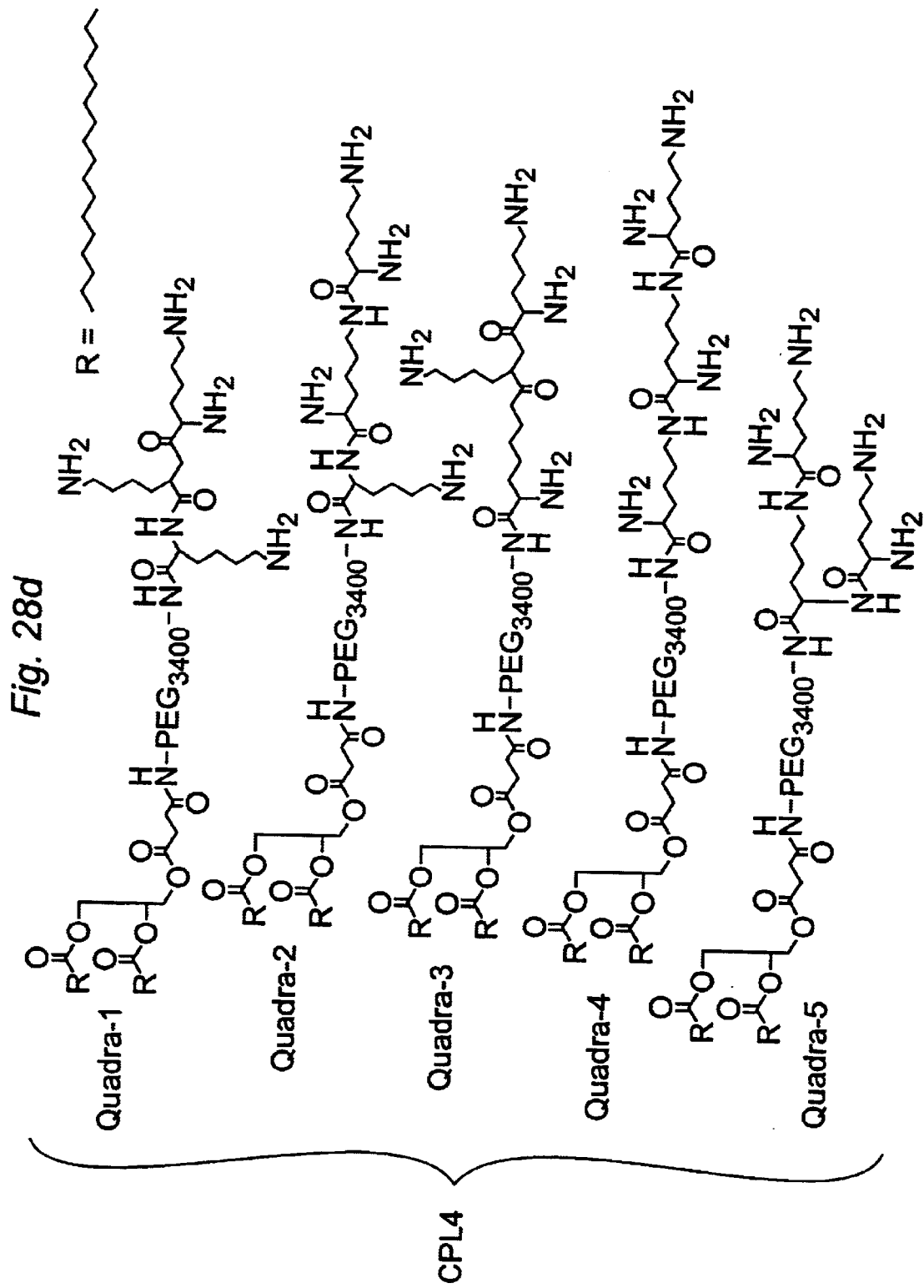

The in vitro cellular uptake of CPL-containing liposomes was studied on baby hamster kidney (BHK) cells. The liposome-associated fluorescent lipid marker (Rh-PE) was used as a marker for lipid uptake. As shown in FIGS. 26 and 27, $CPL_4$ significantly enhances the cellular uptake compared to control samples (no CPL) using both PBS-CMG and serum containing medium. The time dependent uptake of CPL-LUVs reaches a maximum after 3 hr. FIG. 6 summarized the cell uptake of the different CPL-containing vesicles after a four hour incubation. Compared to a control, reduced cell uptake was observed for $CPL_1$, a moderate increase for $CPL_2$ (2 fold), and a large increase for both $CPL_4$ and $CPL_8$. The similar degree of increase resulting from $CPL_4$ and $CPL_8$ indicates a charge density of four in the CPLs satisfies the requirement for maximum enhanced cellular uptake.

VII. Example VII

A. General Overview

This experiment describes the synthesis of a new class of cationic lipids designed to enhance non-specific targeting by increasing the electrostatic attraction between liposomes and cells.

B. Materials and Reagents tBoc-NH-$PEG_{3400}$-$CO_2$-NHS was obtained from Shearwater Polymers (Huntsville, Ala.). $N_\alpha,N_\epsilon$-i-tBoc-L-lysine-N-hydroxysuccinimide ester, $N_\epsilon$-dansyl-L-lysine, N-hydroxysuccinimide (NHS), and N,N'-dicyclohexylcarbodiimide (DCC) were purchased from Sigma-Aldrich Canada (Oakville, ON). 1,2-Distearoyl-sn-glycero-3-phosphocholine (DSPC) and 1,2-distearoyl-sn-glycero-3-phosphoethanolamine (DSPE) were obtained from Northern Lipids (Vancouver, BC). Fluorescamine and Rhodamine-DSPE (Rh-PE) were obtained from Molecular Probes (Eugene, Oreg.). Cholesterol (Chol) was obtained from Sigma Aldrich Canada (Oakville, ON). Trifluoroacetic acid, diethyl ether, methanol, triethylamine, and chloroform were obtained from Fisher Scientific (Vancouver, BC). All reagents were used without further purification.

1. General Methods

All reactions were performed in 16×100 mm glass test tubes. $^1$H NMR spectra were obtained employing a Bruker MSL 200 spectrometer operating at 200 MHz. Deuterated chloroform ($CDCl_3$) was used as the solvent in the NMR experiments. Proton chemical shifts (δ) were referenced to $CHCl_3$ set at 7.24 ppm. When signals were reasonably resolved, their intensities were integrated to allow an estimation of the number of protons. The chemical shifts of exchangeable amino group protons, observed between 7–8 ppm, are not given. These peaks were assigned on the basis of their removal by a $D_2O$ exchange.

Phosphorus and fluorescamine assays were performed to confirm the ratio of primary amine per phosphate in each CPL as follows.

The phosphate concentration of the CPL was determined using the Fiske-Subarrow phosphorus assay (see, Fiske, C. H., and Subbarow, Y. (1995) The calorimetric determination of phosphorous. *J. Biol. Chem.* 66, 375–400.). The primary amine concentration in the CPL was determined using the fluorophore, fluorescamine. A fluorescamine solution (0.6 mg/mL) in acetone was prepared. An aliquot of CPL solution in HBS (2–4 μL) was made up to 250 μL with 200 mM sodium borate, pH 8.0. To this mixture, 50 L of the fluorescamine solution was added dropwise with vortexing, followed by 1700 μL of water. The fluorescence of this solution was measured using a Perkin-Elmer LS50 Luminescence Spectrometer with $\lambda_{ex}$ of 397 nm and $\lambda_{em}$ of 475 nm, and excitation and emission slit widths of 10 nm. The primary amine concentration of the CPL was determined from a lysine standard curve.

tBoc-NH-$PEG_{3400}$-$CO_2$-($N_\epsilon$-dansyl)lysine (1). tBoc-NH-$PEG_{3400}$-$CO_2$-NHS (500 mg, 147 μmol) in 3 mL of dry chloroform was added slowly to a solution of $N_\epsilon$-dansyl-L-lysine (65 mg, 171 μmol) in 1 mL of methanol and 200 μL of triethylamine. After the reaction mixture was stirred at room temperature for 3 h, the solvent was removed under a $N_2$ stream and further dried under vacuum. The crude product was washed by first dissolving it in a minimum amount of chloroform with warming and then precipitating it out with the addition of 10 mL of diethyl ether. The ether was added while vortexing. Precipitation of 1 was accelerated by cooling. The precipitate was then pelleted by centrifugation and the ether was discarded. This chloroform/ether wash and precipitation procedure was repeated. The dry solid was then dissolved in 4 mL of chloroform and cooled in an ice bath for 15 min. Methanol (2 mL) was added if this cooled solution was clear. If a precipitate (excess dansyl lysine) developed, it was filtered off prior to the addition of methanol. The chloroform/methanol solution was washed with 1.2 mL of 0.1 M HCl. The chloroform phase was extracted, dried, and the solid redissolved in 6 mL of chloroform/methanol (2:1 v/v) and washed with 1.2 mL of distilled water. The chloroform phase was extracted, dried to a thick paste and tBoc-NH-PEG-$CO_2$-($N_\epsilon$-dansyl)lysine (1) was precipitated with 10 mL of ether. After centrifugation and the removal of ether, the dried product is a light yellow solid. Yield: 520 mg (93%). TLC (silica gel) chloroform/methanol (85:15 v/v): $R_f$ 0.56. $^1$H NMR ($CDCl_3$): δ 1.08 (t), 1.40 (s, 11H), 2.66 (s, 1H), 2.86 (s, 8H), 3.27 (q), 3.50 (t), 3.60 (s, 309H), 3.96 (t), 4.19 (m[broad]), 5.03 (s[broad], 1H), 5.22 (t, 1H), 5.43 (d, 1H), 7.16 (d, H), 7.51 (q, 2H), 8.19 (d, 1H), 8.27 (d), 8.50 (d, 1H) ppm.

Dansylated $CPL_1$-tBoc (3). First, tBoc-NH-$PEG_{3400}$-$CO_2$-($N_\epsilon$-dansyl)lysine-NHS (2) was prepared as follows. A solution of tBoc-NH-$PEG_{3400}$-$CO_2$-($N_\epsilon$-dansyl)lysine (1) (500 mg, 132 μmol) and NHS (31.5 mg, 274 μmol) in 2 mL of dry chloroform was added to DCC (42.8 mg, 207 μmol) dissolved in 1 mL of dry chloroform. The reaction mixture was stirred for 2 h at room temperature. The by-product, dicyclohexyl urea (DCU), was filtered using a Pasteur pipette with a cotton plug. The filtrate, containing tBoc-NH-$PEG_{3400}$-$CO_2$-($N_\epsilon$-dansyl)lysine-NHS (2), was slowly added to a solution of DSPE (120.6 mg, 161 μmol) in 2 mL of dry chloroform and 200 μL of triethylamine. The dissolution of DSPE in dry chloroform and triethylamine required warming to 65° C. After the reaction mixture was stirred at room temperature for 3 h, it was dried, and chloroform/ether washed and precipitated as described earlier until the disappearance of DSPE on TLC as visualized with ninhydrin. This removal of excess DSPE required at least three washings. The product, dansylated $CPL_1$-tBoc (3), was dissolved in chloroform/methanol (2:1), washed with dilute HCl and water, and precipitated using ether as described for (1). Yield: 575 mg (96%). TLC (silica gel) chloroform/methanol (85:15) $R_f$ 0.58. $^1$H NMR ($CDCl_3$): δ 0.85 (t, 4H), 1.22 (s, 48H), 1.41 (s, 10H), 1.55 (t), 2.27 (m[broad], 6H), 2.90 (m[broad], 6H), 3.04 (s, 8H), 3.27 (q), 3.61 (s, 275H), 4.14 (m[broad]), 4.32 (d), 4.38 (d), 5.05 (s[broad]), 5.23 (s[broad]), 5.58 (m[broad]), 7.37 (d, 1H), 7.49 (s[broad], 1H), 7.59 (t, 2H), 8.24 (d, 1H), 8.50 (d, 1H), 8.59 (d, 1H) ppm.

Dansylated $CPL_1$ (4). Trifluoroacetic acid (TFA) (2 mL) was added to a solution of dansylated $CPL_1$-tBoc (3) (550 mg, 121 μmol) in 2 mL of chloroform and stirred for 4 h at room temperature. The solution was concentrated to a thick paste and chloroform/ether washed three times. After the removal of ether, the solid was dissolved in 6 mL of chloroform/methanol (2:1) and washed with 1.2 mL of 5% sodium bicarbonate. The chloroform phase was extracted, dried and redissolved in 6 mL chloroform/methanol (2:1) and washed with 1.2 mL distilled water. The chloroform phase was concentrated to a thick paste and the purified $CPL_1$ (4) was obtained through a chloroform/ether wash and vacuum dried. Yield: 535 mg (97%). TLC (silica) chloroform/methanol/water (65:25:4) $R_f$ 0.76. $^1$H NMR ($CDCl_3$). δ 0.85 (t, 4H), 1.22 (s, 46H), 1.54 (m[broad], 8H), 2.23 (t, 6H), 2.84 (s, 9H), 3.16 (m[broad], 3H), 3.26 (t, 3H), 3.61 (s, 263H), 3.98 (q), 4.17 (t), 4.33 (d), 4.38 (d), 5.19 (s[broad]), 5.93 (d, 1H), 7.13 (d, 1H), 7.46 (t, 1H), 7.52 (t, 1H), 8.15 (d, 1H), 8.43 (t, 2H) ppm.

Dansylated $CPL_2$-tBoc (5). A solution of $N_\alpha$,$N_\epsilon$-di-tBoc-L-lysine-N-hydroxysuccinimide ester (105 mg, 236 μmol) in 2 mL dry chloroform was gradually added to a solution of dansylated $CPL_1$ (4) (510 mg, 112 μmol) in 2 mL chloroform containing 200 μL triethylamine and stirred at room temperature for 3 h. The completion of the reaction was indicated by the disappearance of primary amine as visualized by ninhydrin assay on TLC. The reaction mixture was concentrated to a thick paste and chloroform/ether washed (3 times) until the disappearance of excess $N_\alpha$,$N_\epsilon$-di-tBoc-L-lysine-N-hydroxysuccinimide ester as checked by TLC. The product was dissolved in 6 mL chloroform/methanol (2:1) and washed with 1.2 mL 0.1 M HCl. The chloroform phase was extracted, dried, redissolved in 6 mL chloroform/methanol (2:1) and washed with 1.2 mL distilled water. The chloroform phase was concentrated to a thick paste and the purified compound was obtained through a chloroform/ether wash and vacuum dried. Yield: 510 mg (96%). TLC (silica gel) chloroform/methanol (85:15) $R_f$ 0.58. $^1$H NMR ($CDCl_3$). δ 0.85 (t, 3H), 1.22 (s, 44H), 1.41 (s, 20H), 1.56 (m[broad]), 1.78 (m[broad]), 2.27 (m, 5H), 2.88 (s), 2.91 (s), 2.97 (s), 3.06 (s, 7H), 3.26 (t), 3.44 (t), 3.62 (s, 252H), 3.97 (t), 4.05 (d), 4.13 (m), 4.33 (d), 4.38 (d), 4.68 (s[broad]), 5.22 (s[broad]), 5.51 (s[broad]), 6.57 (t[broad], 1H), 7.39 (d, 1H), 7.51 (s[broad], 1H), 7.60 (t, 2H), 8.26 (d, 1H), 8.53 (d, 1H), 8.61 (d, 1H) ppm.

Dansylated CPL$_2$ (6). The synthesis of CPL$_2$ (6) was the same as that of CPL$_1$ (4) by deprotecting dansylated CPL$_2$-tBoc (5) (490 mg, 103 μmol). Yield: 478 mg (97%). TLC (silica) chloroform/methanol/water (65:25:4) R$_f$0.63. $^1$H NMR (CDCl$_3$). δ 0.85 (t, 3H), 1.22 (s, 42H), 1.55 (m, 10H), 1.93 (s[broad], 4H), 2.24 (t, 5H), 2.85 (s, 8H), 3.26 (t, 3H), 3.61 (s, 271H), 3.95 (q), 4.17 (s), 4.34 (s), 5.18 (s[broad], 1H), 6.31 (d, 1H), 6.89 (s, 1H), 7.10 (d, 1H), 7.49 (m, 1H), 8.15 (d, 1H), 8.34 (d, 1H), 8.47 (d, 2H) ppm.

Dansylated CPL$_4$-tBoc (7). The synthesis of CPL$_4$-tBoc (7) was the same as that of CPL$_2$-tBoc (5) by reacting N$_\alpha$,N$_\epsilon$-di-tBoc-L-lysine-N-hydroxysuccinimide ester (170 mg, 383 μmol) with dansylated CPL$_2$ (6) (455 mg, 95 μmol). Yield: 475 mg (96%). TLC (silica gel) chloroform/methanol (85:15) R$_f$0.58. $^1$H NMR (CDCl$_3$). δ 0.85 (t, 3H), 1.22 (s, 43H), 1.40 (s, 39H), 1.71 (m[broad], 262H), 2.27 (m, 5H), 2.88 (s), 2.90 (s), 3.05 (s, 10H), 3.25 (t, 3H), 3.43 (s), 3.61 (s, 262H), 3.97 (t), 4.05 (d), 4.15 (m), 4.32 (d), 4.37 (d), 4.51 (s[broad]), 4.75 (s[broad]), 4.90 (s[broad]), 5.23 (t[broad], 1H), 5.52 (s[broad]), 5.80 (s[broad], 1H), 7.15 (m[broad], 1H), 7.38 (d, 1H), 7.50 (s, 1H), 7.59 (t, 2H), 8.25 (d, 1H), 8.51 (d, 1H), 8.60 (d, 1H) ppm.

Dansylated CPL$_4$ (8). The synthesis of CPL$_4$ (8) was the same as that of CPL$_1$ (4) by deprotecting dansylated CPL$_4$-tBoc (7) (450 mg, 86 μmol). Yield: 440 mg (97%). TLC (silica) chloroform/methanol/water (65:25:4) R$_f$0.19. $^1$H NMR (CDCl$_3$). δ 0.85 (t), 1.22 (s), 1.53 (m[broad]), 2.34 (m[broad]), 2.86 (s), 3.26 (t), 3.62 (s), 3.87 (s[broad]), 3.97 (t), 4.17 (s[broad]), 4.33 (d), 5.18 (s[broad]), 7.15 (d), 7.43 (s), 7.51 (t), 8.15 (d), 8.32 (d), 8.48 (d), 9.05 (s[broad]) ppm.

Dansylated CPL$_8$-tBoc (9). The synthesis of CPL$_8$-tBoc (9) was the same as that of CPL$_2$-tBoc (5) by reacting N$_\alpha$,N$_\epsilon$-di-tBoc-L-lysine-N-hydroxysuccinimide ester (70 mg, 158 μmol) with dansylated CPL$_4$ (8) (100 mg, 19 μmol). Yield: 112 mg (96%). TLC (silica gel) chloroform/methanol (85:15) R$_f$0.58. $^1$H NMR (CDCl$_3$). δ 0.84 (t, 3H), 1.08 (s), 1.21 (s, 39H), 1.39 (s, 75H), 1.66 (m [broad]), 2.26 (m, 4H), 2.89 (s, 4H), 3.06 (s, 11H), 3.25 (t, 3H), 3.43 (s), 3.49 (s), 3.60 (s, 248H), 3.96 (t), 4.04 (d), 4.12 (t), 4.31 (d), 4.36 (m), 5.19 (m [broad]), 6.77 (m [broad], 1H), 6.91 (s [broad], 1H), 7.24 (CHCl$_3$), 7.41 (d), 7.50 (s [broad]), 7.60 (t), 8.25 (d, 1H), 8.53 (d, 1H), 8.63 (d, 1H) ppm.

Dansylated CPL$_8$ (10). The synthesis of CPL$_8$ (8) was the same as that of CPL$_1$ (4) by deprotecting dansylated CPL$_8$-tBoc (9) (50 mg, 8 μmol). Yield: 48 mg (96%). TLC (silica) chloroform/methanol/water (65:25:4) R$_f$0.13. $^1$H NMR (CDCl$_3$). δ 0.85 (t, 3H), 1.22 (s, 34H), 1.52 (s [broad]), 2.23 (s [broad]), 2.86 (d), 3.27 (d), 3.61 (s, 274H), 3.96 (t), 4.18 (m [broad]), 7.14 (s [broad]), 7.24 (CHCl$_3$), 7.50 (m [broad]), 8.12–8.27 (s [broad]), 8.47 (m [broad]) ppm.

C. Results and Discussion

Figure 29A:
Figure 30:
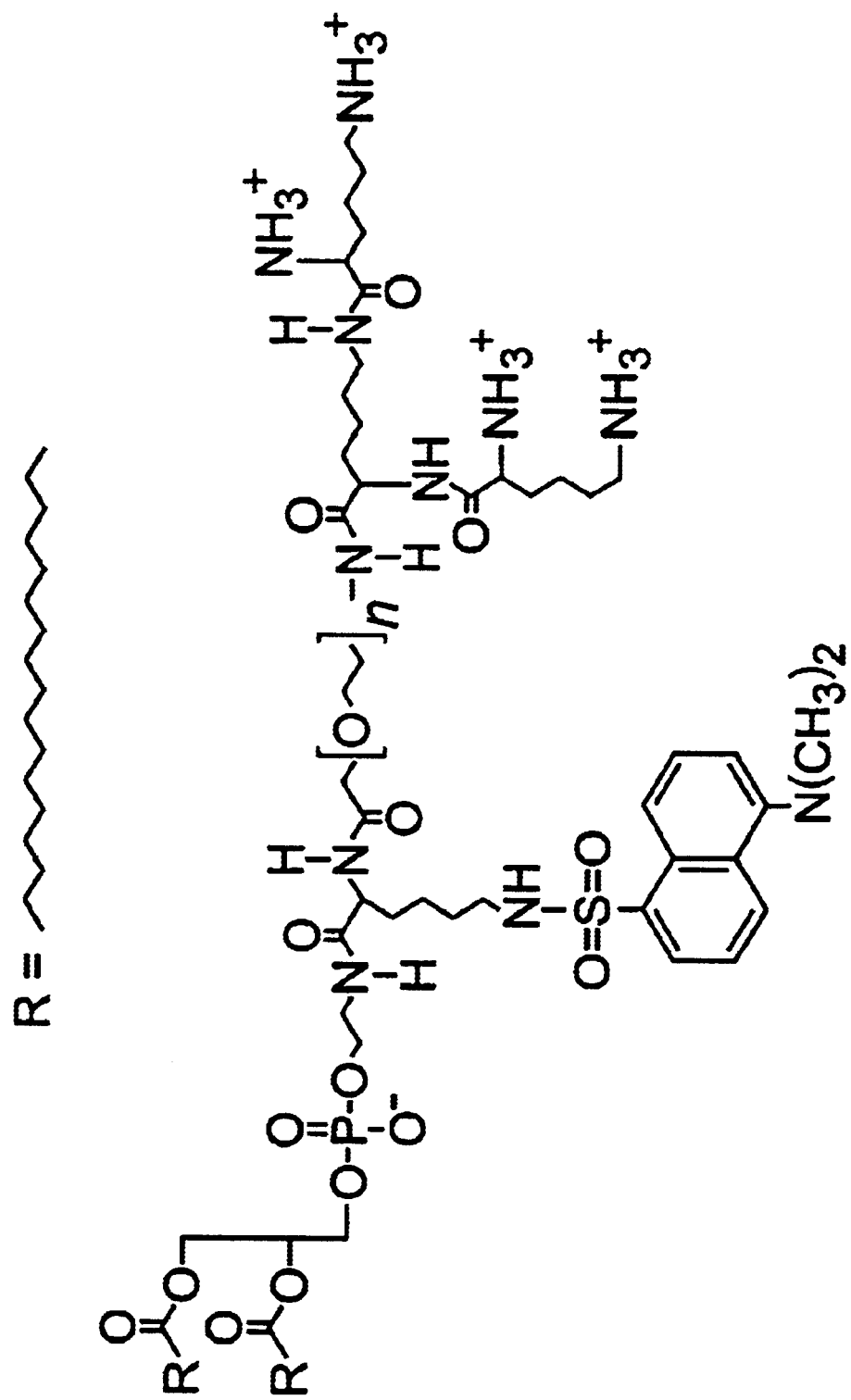
FIG. 30 illustrates a structure of dansylated $CPL_4$. $CPL_4$ possesses four positive charges at the end of a $PEG_{3400}$ molecule which is attached to a DSPE molecule. The $CPL_4$ is dansylated by incorporation of a dansylated lysine.

The CPL were synthesized by repeated coupling reaction steps involving amines and NHS-activated carbonate groups as outlined in FIG. 29. This consists of (a) incorporating the dansyl fluorescent label to the hydrophilic PEG spacer, (b) coupling of the DSPE anchor, and (c) attachment of the cationic headgroup to the lipid. The heterobifunctional PEG polymer tBoc-NH-PEG$_{3400}$-CO$_2$-NHS (MW 3400), was chosen for two reasons. Firstly, it was commercially available. Secondly, it is insoluble in ether that provided a very convenient means of purifying its derivatives, 1–10. Other reagents were used in excess to ensure the complete conversion of the PEG polymer to its derivatives. The excess reagents were soluble in ether and therefore could be removed by washing in ether during purification.

Incorporation of the fluorescent label, N$_\epsilon$-dansyl lysine, to the PEG polymer by coupling the α-amino group of dansyl lysine with the NHS activated carbonate of PEG gave the lysine derivative 1. The DSPE anchor was coupled via intermediate 2 that was formed by the esterification of 1 using NHS and DCC. The resulting PEG lipid, 3, was deprotected by removing the tBoc to form CPL$_1$, 4, with one positive charge. The positive charges in the other CPL are carried by the amino groups of lysine. Here, the NHS activated and di-tBoc protected lysine was attached to the free amino function of CPL$_1$ to form intermediate 5 which, upon deprotection, yielded CPL$_2$, 6, with two positive charges. The attachment of two lysine residues to the amino groups of CPL$_2$ via intermediate 7 gave CPL$_4$, 8, with four positive charges. Thus, CPL$_8$, 10, with eight positive charges was synthesized with the attachment of four lysine residues as the headgroup. As can be seen, this provides a very convenient means of synthesizing multivalent CPL that are of particular interest for non-viral drug delivery applications.

The structures of the purified intermediates and CPL in FIG. 29 were verified by $^1$H NMR spectroscopy and chemical analysis. The $^1$H NMR spectra showed well-resolved resonances for the PEG, tBoc and acyl chains of DSPE at approximately 3.61, 1.41 and 1.21 ppm, respectively, and for the resonances of the dansyl moiety (aromatic protons at 7.1–8.5 ppm; methyl protons at 2.8–3.0 ppm). From the integrated signal intensities of the former three peaks, it was found that the ratio of tBoc/PEG or tBoc/DSPE was 1.0, 2.1, 4.0, and 8.1 for CPL$_1$-tBoc, CPL$_2$-tBoc, CPL$_4$-tBoc, and CPL$_8$-tBoc, respectively. As each tboc is attached to an amino group, this gives the number of amino groups in the headgroup of each CPL relative to the CPL$_1$. That essentially identical results were obtained using the ratios of tBoc relative to both PEG and DSPE demonstrates the presence of lipid and polymer in correct proportion to the headgroup. The complete cleavage of the tBoc protecting groups was verified by the loss of tboc NMR peaks and chemical analysis which determined the ratio of primary amine to phosphate in each of the CPL by using the fluorescamine and phosphorus assays. The amine/phosphate ratios for CPL$_1$, CPL$_2$, CPL$_4$, and CPL$_8$ were found to be 1.0, 2.2, 3.7, and 8.0, respectively. These corresponded well with the expected number of positive charge bearing amino groups of the respective CPL.

The CPL described here possess several attributes which may increase their usefulness relative to other cationic lipids. Firstly, the phospholipid anchor will readily allow efficient incorporation of CPL into liposomal systems. Secondly, the dansyl label will permit accurate and convenient quantification of the CPL in the bilayer using fluorescence techniques. Finally, the valency of the cationic headgroup in the CPL can easily be modified using lysine residues.

VIII. Example VIII

A. General Overview

The synthesis of a fluorescent cationic poly(ethylene glycol) (MW 1000) lipid conjugates (CPL)[1] is described. The procedure is very similar to that of PEG 3400 described in detail previously. However the lower molecular weight PEG derivatives may not be insoluble in ether, and therefore could not be readily purified by ether wash as before. The synthetic procedure is similar to the one outlined in FIG. 29.

B. Abbreviations tBoc, tert-butyloxycarbonyl; tBoc-NH-PEG$_{1000}$-CO$_2$-NHS, tboc protected and NHS activated PEG$_{1000}$; CPL, cationic poly(ethylene glycol) lipid conjugate; CPL$_1$, CPL with one positive charge; CPL$_2$, CPL with two positive charges; CPL$_4$, CPL with four positive charges; DCC, N,N'-dicyclohexyl-carbodiimide; DCU, dicyclohexyl urea; NHS, N-hydroxysuccinimide; di-tBoc-lysine-NHS, $N_\alpha,N_\epsilon$-di-tBoc-L-lysine-N-hydroxysuccinimide ester; DSPE, 1,2-distearoyl-sn-glycero-3-phosphoethanolamine; $PEG_{1000}$, poly(ethylene glycol) with an average MW of 1000; TFA, trifluoroacetic acid.

C. Materials and Reagents tBoc-NH-$PEG_{1000}$-$CO_2$-NHS was obtained from Shearwater Polymers (Huntsville, Ala.). $N_\alpha,N_\epsilon$-di-tBoc-L-lysine-N-hydroxysuccinimide ester, $N_\epsilon$-dansyl-L-lysine, N-hydroxysuccinimide (NHS), and N,N'-dicyclohexyl-carbodiimide (DCC) were purchased from Sigma-Aldrich Canada (Oakville, ON). 1,2-Distearoyl-sn-glycero-3-phosphoethanolamine (DSPE) was obtained from Northern Lipids (Vancouver, BC). Fluorescamine was obtained from Molecular Probes (Eugene, Oreg.). Trifluoroacetic acid, diethyl ether, methanol, triethylamine, and chloroform were obtained from Fisher Scientific (Vancouver, BC). All other reagents were used without further purification.

tBoc-NH-$PEG_{1000}$-$CO_2$-($N_\epsilon$-dansyl)lysine (1). tBoc-NH-$PEG_{1000}$-$CO_2$-NHS (500 mg, 500 $\mu$mol) in 3mL of dry chloroform was added slowly to a solution of $N_\epsilon$-dansyl-L-lysine (200 mg, 536 $\mu$mol) in 1.5 mL of methanol and 300 $\mu$L of triethylamine. After the reaction mixture was stirred at room temperature for 3 h, the solvent was removed under a $N_2$ stream and further dried under vacuum. The crude product was dissolved in 6 mL of chloroform/methanol (2:1 v/v), washed once with 1.2 mL of 0.5 M HCl and twice with 1.2 mL of distilled water. The chloroform phase was extracted, dried to a thick paste and tBoc-NH-PEG-$CO_2$-($N_\epsilon$-dansyl)lysine (1) was obtained as a light yellow solid. Yield: 600 mg (95%). TLC (silica gel) chloroform/methanol (85:15 v/v): $R_f$ 0.50.

Dansylated $CPL_1$-tBoc (3), First, tBoc-NH-$PEG_{1000}$-$CO_2$-($N_\epsilon$-dansyl)lysine-NHS (2) was prepared as follows. A solution of tBoc-NH-$PEG_{1000}$-$CO_2$-($N_\epsilon$-dansyl)lysine (1) (600 mg, 474 $\mu$mol) and NHS (113 mg, 982 $\mu$mol) in 2 mL of dry chloroform was added to DCC (150 mg, 728 $\mu$mol) dissolved in 1 mL of dry chloroform. The reaction mixture was stirred for 5 h at room temperature. The by-product, dicyclohexyl urea (DCU), was filtered using a Pasteur pipette with a cotton plug. The filtrate, containing tBoc-NH-$PEG_{1000}$-$CO_2$-($N_\epsilon$-dansyl)lysine-NHS (2), was slowly added to a solution of DSPE (365 mg, 488 $\mu$mol) in 3 mL of dry chloroform and 300 $\mu$L of triethylamine. The dissolution of DSPE in dry chloroform and triethylamine required warming to 65° C. After the reaction mixture was stirred overnight at room temperature, it was filtered to remove some precipitate (unreacted DSPE) and dried to a viscous paste. The paste was dissolved in chloroform/methanol (2:1), washed with dilute HCl and water as before. The product, dansylated $CPL_1$-tBoc (3), was obtained after the removal of solvent and precipitated using 10 mL of ether. Yield: 900 mg (96%). TLC (silica gel) chloroform/methanol (85:15) $R_f$ 0.58.

Dansylated $CPL_1$ (4). Trifluoroacetic acid (TFA), 3 mL, was added to a solution of dansylated $CPL_1$-tBoc (3) (900 mg, 456 $\mu$mol) in 3 mL of chloroform and stirred for 4 h at room temperature. The solution was concentrated to a thick paste and chloroform/ether washed three times. After the removal of ether, the solid was dissolved in 6 mL of chloroform/methanol (2:1) and washed twice with 1.2 mL of 5% sodium bicarbonate and twice with 1.2 mL distilled water. The chloroform phase was concentrated to a thick paste and the purified $CPL_1$ (4) was obtained through a chloroform/ether wash and vacuum dried. Yield: 750 mg (88%). TLC (silica) chloroform/methanol/water (65:25:4) $R_f$ 0.72.

Dansylated $CPL_2$-tBoc (5). A solution of $N_\alpha,N_\epsilon$-di-tBoc-L-lysine-N-hydroxysuccinimide ester (350 mg, 789 $\mu$mol) in 3 mL dry chloroform was gradually added to a solution of dansylated $CPL_1$ (4) (750 mg, 400 $\mu$mol) in 3 mL chloroform containing 300 $\mu$L triethylamine and stirred at room temperature for 3 h. The completion of the reaction was indicated by the disappearance of primary amine as visualized by ninhydrin assay on TLC. The reaction mixture was concentrated to a thick paste, redissolved in 6 mL chloroform/methanol (2:1) and washed once with 1.2 mL 0.5 M HCl four times with 1.2 mL distilled water. The chloroform phase was extracted and dried. No further purification was performed. Yield: 700 mg (81%). TLC (silica gel) chloroform/methanol (85:15) $R_f$ 0.58.

Dansylated $CPL_2$ (6). The synthesis of $CPL_2$ (6) was the same as that of $CPL_1$ (4) by deprotecting dansylated $CPL_2$-tBoc (5) (700 mg, 318 $\mu$mol). Yield: 650 mg (92%). TLC (silica) chloroform/methanol/water (65:25:4) $R_f$ 0.63.

Dansylated $CPL_4$-tBoc (7). The synthesis of $CPL_4$-tBoc (7) was the same as that of $CPL_2$-tBoc (5) by reacting $N_\alpha,N_\epsilon$-di-tBoc-L-lysine-N-hydroxysuccinimide ester (500 mg, 1127 $\mu$mol) with dansylated $CPL_2$ (6) (650 mg, 292 $\mu$mol). Besides washing with dilute HCL and water no further attempts were made to purify $CPL_4$-tBoc before deblocking to generate $CPL_4$. Yield: 800 mg (Crude). TLC (silica gel) chloroform/methanol (85:15) $R_f$ 0.58 (dansyl peak only).

Dansylated $CPL_4$ (8). The synthesis of $CPL_4$ (8) was the same as that of $CPL_1$ (4) by deprotecting dansylated $CPL_4$-tBoc (7) (800 mg). The final product was purified by column chromatography using silica gel 60, 70–230 mesh, and chloroform/methanol/ammonia solution (65:25:4 v/v). Yield: 300 mg (38%). TLC (silica) chloroform/methanol/water (65:25:4) $R_f$ 0.15.

IX. Example IX

A. General Overview

We show here that $CPL_4$ can be inserted into preformed SPLP and that the resulting SPLP-$CPL_4$ exhibit improved uptake and markedly improved in vitro transfection potency in BHK cells. These results establish that the SPLP system is intrinsically a highly potent transfection vector.

B. Materials and Methods

1. Preparation of SPLP, SPLP-$CPL_4$, and Complexes (i). SPLP: SPLP composed of DOPE:DODAC:PEG-$CerC_{20}$ (84:6:10) and containing the plasmid pLuc, a modified marker gene expressing luciferase, was supplied by INEX Pharmaceuticals Inc.

(ii) SPLP-$CPL_4$: Dansylated $CPL_4$ was prepared in our laboratory and incorporated into SPLP as follows: SPLP at a dose of 500 nmol lipid was incubated with different amounts of $CPL_4$ (12.5, 19, and 30 nmol) at 60° C. for 2 to 3 hours in Hepes Buffered Saline, pH 7.5 (HBS) to achieve a final incorporation of 2, 3, and 4 mol %, respectively. SPLP-CPL was separated from unincorporated CPL by gel filtration chromatography on a Sepharose CL-4B column equilibrated in HBS. Fractions (1 mL) were collected and assayed for CPL, phospholipid and DNA contents. Fractions containing all three components were pooled and concentrated for use in transfection and uptake studies. The samples from the column were greatly aggregated. To deaggregate the systems, addition of $CaCl_2$ or $MgCl_2$ was required. Experiments to determine the optimal amount of cation for deaggregation will be described later in the Methods.

CPL Assay: The presence of CPL was determined by measuring the fluorescence of the dansyl group in CPL on a Perkin Elmer LS52 Luminescence spectrophotometer using $\lambda_{ex}$=340 nm and $\lambda_{em}$=510 nm with excitation and emission slit widths of 10 and 20 nm, respectively. Fluorescence of the dansyl was quantified using a standard curve of dansylated CPL in HBS.

Phospholipid Assay: Phospholipid was determined by first extracting the lipids from SPLP using the Bligh-Dyer technique and then measuring phosphate in the organic phase according to the Fiske-Subbarow method (see, Bligh E G, Dyer W J A rapid method of total lipid extraction and purification. *Can J Biochem Physiol* 1959; 37: 911–917; and Fiske C H, Subbarow Y. The colorimetric determination of phosphorous. *J Biol Chem* 1925; 66: 375–400.).

DNA Assay: DNA content was measured using the PicoGreen Assay kit (Molecular Probes, Eugene, Oreg.) as previously described. (see, Mok K W C, Lam A M I, Cullis P R. Stabilized plasmid-lipid particles: factors influencing plasmid entrapment and transfection properties. *Biochim Biophys Acta* 1999; 1419: 137–150).

(iii) Complexes: The complexes were prepared, at a charge ratio of 1.5:1 +ve/–ve, by mixing 25 μL of DOPE::DODAC (0.8 mM), kindly supplied by Inex, with 25 μL of 88 μg/mL pLuc, also supplied by Inex, followed by incubation for 30 min before addition to cells.

2. Preparation of SPLP Containing 0.5 mol % of Rh-PE for Optimal Insertion Time Determination and Lipid Uptake Experiments SPLP were prepared as described by Wheeler et al. (see, Wheeler et al., *Gene Therapy*; 6:271–281 (1999)) with a few modifications. The lipids DOPE, PEG-CerC$_{20}$, DODAC, and rhodamine-DOPE (Rh-PE), all stocks in CHCl$_3$, were mixed together in a molar ratio of (83.5:10:6:0.5) and the CHCl$_3$ was completely evaporated. The resulting lipid film was dissolved in 20 mM octyl glucopyranoside (OGP) and 200 μg/mL of plasmid DNA was added to a total volume of 1 mL. The OGP was dialysed from the sample in a dialysis bag with two changes of buffer (HBS) over 48 hours. The resulting sample was passed down a DEAE Sepharose column and the effluent was run on a discontinuous sucrose gradient as described previously. (see, Gabizon A, Papahadjopoulos D. Liposome formulations with prolonged circulation time in blood and enhanced uptake by tumors. *Proc Natl Acad Sci USA* 1988; 85: 6949–6953.). The resulting rhodamine-labeled SPLP possessed a DNA/Lipid ratio of ~60 μg/mol.

3. Determination of Optimal Incubation Time for Insertion of CPL4 into SPLP

To determine the time required for optimal insertion of CPL$_4$ into SPLP, 5 mol % of CPL$_4$ (0.3 nmol) was mixed with 6 nmol of SPLP (containing 0.5 mol % Rh-PE) in a total volume of 1.5 mL and incubated in a 60° C. water bath. At time points (30 min. 1 h, 2 h, 3 h, and 4 h), 250 μL of the mixture was run down a Sepharose CL-4B column equilibrated with HBS. The fractions possessing fluorescent dansyl were combined and the dansyl fluorescence was measured using the parameters described above while the rhodamine fluorescence was measured using $\lambda_{ex}$=560 nm, $\lambda_{em}$=590 nm, and excitation and emission slit widths of 10 and 20 nm, respectively. These measurements were also made on a small fraction of the original solution before the column. The dansyl/rhodamine ratios are calculated for both the initial and final samples to determine the percentage of the initial 5 mol % that was inserted.

4. Deaggregation of SPLP-CPL$_4$ Using CaCl$_2$ and MgCl$_2$

As stated above, the preparation of SPLP-CPL$_4$ results in aggregation of the particles. To deaggregate the system an increase in ionic strength is required. This was achieved by the addition of increasing amounts of CaCl$_2$ or MgCl$_2$ (500 mM stock solution) to a solution of SPLP-CPL$_4$. To 60 μL of SPLP-CPL$_4$ (3 mM lipid) was added a 360 μL of HBS in a Nicomp tube. The mean diameter±standard deviation of the SPLP-CPL$_4$ (0 mM Cation) was then determined by QELS using a Nicomp Model 270 Submicron Particle Sizer, Then the salt (CaCl$_2$ or MgCl$_2$) was added to concentrations from 20 mM to 70 mM. At each interval the mean diameter standard deviation was determined by QELS. The mean diameter of the particles hardly changes with increasing [Cation] however, the QELS Gaussian distribution gets broader. Therefore, the standard deviations were used as a measure of deaggregation.

5. Size Determination of SPLP-CPL4 and SPLP

Freeze-fracture EM was performed on the SPLP-CPL$_4$ (no CaCl$_2$), SPLP-CPL$_4$+40 mM CaCl$_2$, and SPLP, according to Wheeler et al. (see, Wheeler J J et al. Stabilized plasmid-lipid particles: construction and characterization. *Gene Therapy* 1999; 6: 271–281.). The SPLP-CPL$_4$ contained 4 mol % CPL$_4$. The micrographs of SPLP-CPL$_4$, in the presence and absence of CaCl$_2$, were compared to show the visual effect of Ca$^{2+}$ on the aggregation. Vesicle diameters of the SPLP-CPL$_4$+40 mM CaCl$_2$ and SPLP were analyzed by QELS using a Nicomp Model 270 Submicron Particle Sizer.

6. Serum Stability of SPLP-CPL4 Particles

The serum stability of the SPLP-CPL containing various % of CPL were determined by mixing the particles with mouse serum to a final serum concentration of 50%$_v$. These mixtures were then incubated for 0, 1, 2, or 4 hours at 37° C. At these time points, a volume of the mixture containing about 1 μg of plasmid DNA was removed and the DNA was extracted from the lipid and protein using a phenol:chloroform extraction. The resulting DNA solutions were then run on a 1% agarose gel following which the DNA was transferred to nitrocellulose and a Southern blot was performed.

7. Lipid Analysis of SPLP-CPL$_4$

To determine the loss of PEG-CerC$_{20}$ from the SPLP during the insertion of CPL$_4$, lipid was extracted for the SPLP sample and SPLP-CPL$_4$ sample by the Bligh-Dyer extraction. The mixtures were then passed through an HPLC and were assayed for DOPE and PEG-CerC$_{20}$ by Northern Lipids, Inc (Vancouver, BC). The DOPE:PEG-CerC$_{20}$ ratios for the SPLP-CPL was compared to that for the SPLP and the amount of PEGylated lipid in the outer monolayer of the SPLP was determined.

8. Uptake Studies

For all in vitro experiments, the cells used were a transformed BHK cell line (tk-). For the uptake studies, 1×10$^5$ BHK cells were grown on 12-well plates overnight in 2 mL of complete media (DMEM+10% FBS) at 37° C. in 5% CO$_2$. SPLP, SPLP-CPL$_4$+40 mM CaCl$_2$, or DOPE:DODAC complexes (200 μL), each containing 0.5 mol % Rh-PE as lipid marker were mixed with 800 μL of complete media and this mixture was added to the top of the cells at a lipid dose of 20 μM. After incubation at 37° C. for 2, 4, 6, or 8 hours, the cells were washed with PBS and lysed with 600 μL of lysis buffer (0.1% Triton X-100 in PBS). The rhodamine fluorescence of the lysate was measured in a 1.0 mL microcuvette on a Perkin-Elmer LS52 Luminescence Spectrophotometer using a $\lambda_{ex}$ of 560 nm and a $\lambda_{em}$ of 600 nm with slit widths of 10 and 20 nm, respectively. An emission filter of 430 nm was also used. Lipid uptake was determined by comparison of the fluorescence in the lysate to that of a lipid standard and normalized to the amount of cells as determined by the BCA protein assay (Pierce, Rockford, Ill.). Where indicated, fluorescence micrographs were taken on an Axiovert 100 Zeiss Fluorescent microscope (Carl Zeiss Jena GmbH) using a rhodamine filter from Omega Opticals (Brattleboro, Vt.) with the following specifications, $\lambda_{ex}$=560±20 nm, 600 nm LP, and DC 590 nm.

9. Effect of Type and Concentration of Cation on Lipid Binding and Uptake

This uptake experiment was performed with the same SPLP-CPL$_4$ (containing 0.5 mol % Rh-PE) as above. 5×10$^4$ BHK cells were plated overnight in 1 mL of complete media in 24-well plates. The SPLP-CPL$_4$ (40 nmol) was mixed with CaCl$_2$ or MgCl$_2$ at various initial concentrations of 20 mM to 70 mM in a total volume of 100 μL. To this was added 400 μL of complete media resulting in final [Cation] of 4 mM to 14 mM. This mixture was then added to the top of the cells and the cells incubated for 4 hours. After incubation the cells were washed twice with PBS and 600 μL of lysis buffer (0.1% Triton X-100 in PBS) was added. As above, the rhodamine fluorescence was measure and the lipid uptake was determined comparing the resulting fluorescence to that of a standard sample containing a known amount of lipid. The resulting values were then normalized to the number of cells by measuring the protein content using the BCA protein assay kit.

10. Transfection Studies

1×10$^4$ BHK cells were plated in 96-well plates in 150 μL complete media and incubated overnight at 37° C. in 5% CO$_2$. SPLP and SPLP-CPL, containing between 2 and 4 mol % CPL, were prepared to deliver 0.5 μg of DNA in a total volume of 20 μL using HBS (SPLP), or HBS+40 mM CaCl$_2$ (SPLP-CPL$_4$) and were added to 90 μL of complete media. Samples were incubated with the cells for 4 hours. The transfection media was then replaced with complete media for a complete 24 hour incubation. Cells were then lysed with 100 μL of lysis buffer, and 40 μL of the lysate was transferred to a 96-well luminescence plate. Luciferase activity was determined using a Luciferase reaction kit (Promega, Madison, Wis.), a luciferase standard (Boehringer-Manheim), and a ML3200 microtiter plate luminometer from Molecular Dynamics (Chantilly, Va.). Activity was normalized to the number of cells as measured by the BCA protein assay (Pierce, Rockford, Ill.). From the uptake and transfection experiments above, it was determined that 4 mol % CPL$_4$ in SPLP-CPL$_4$ gave optimal results. Thus, the rest of the experiments were performed with SPLP-CPL$_4$ containing 4 mol % CPL$_4$.

11. Time Course for the Transfection of SPLP-CPL Versus SPLP and Complexes

Samples and cells were prepared as described for the above transfection study, and incubated together at 37° C. As well, Lipofectin (Gibco BRL) complexes containing pLuc were prepared at a charge ratio of 1.5:1. At 4, 9, and 24 hours, the transfection media was removed and in the case of the 4 and 9 hour transfections, replaced with complete media for a complete 24-hour incubation. At 24 h, all cells were lysed and assayed for luciferase activity and protein content (BCA assay), as above.

12. Transfection Potency and Toxicity of SPLP-CPL4

BHK cells were incubated with SLPP, SPLP-CPL$_4$+40 mM CaCl$_2$, and Lipofectin complexes for 24 or 48 hours. After the incubation period the cells were immediately lysed and the luciferase activity was measured and was normalized to the amount of protein present, as above.

As a rough measure of cell survival at the above time points, the protein concentration after cell lysis at 24 and 48 hours was measured and compared for the SPLP-CPL$_4$+40 mM CaCl$_2$ and the Lipofectin complexes.

13. Comparison of Effect of Ca2+ and Mg2+ on Transfection of BHK Cells

Cells were plated and used as above. SPLP-CPL$_4$ (5.0 μg/mL) with either CaCl$_2$ or MgCl$_2$ at concentrations of 20 mM to 70 mM were combined in a volume of 20 μL and mixed with complete media, resulting in final [Cation] of 4 mM to 14 mM. Following incubation on the cells for 48 hours, the cells were washed and lysed, and the luciferase activity and protein content were measured as above.

14. Measurement of Transfection Efficiency of SPLP-CPL4

The transfection efficiency of the SPLP-CPL was measured by preparing SPLP-CPL$_4$ containing encapsulated pEGFP (kindly supplied by Inex), that expresses GFP (green fluorescence protein), using the detergent dialysis procedure. (see, Wheeler et al. supra). 400 μg/mL of pEGFP was encapsulated within 10 mM DOPE:PEG-CerC20:DODAC (84:10:6), followed by the insertion of 4 mol % of CPL$_4$. DOPE:DODAC complexes and Lipofectin complexes containing pEGFP were also prepared at a charge ratio of 1.5:1. The transfections were performed as described earlier at a DNA dose of 5.0 μg/mL. Following incubation of the samples for 24 and 48 hours, the transfection media was removed, the cells were washed, and fresh media was added to the cells. The cells were then viewed under the Zeiss fluorescence microscope. The total number of cells within the frame were counted; then the number of cells expressing the GFP were counted using a fluorescein filter (Omega Opticals) with the following specifications, $\lambda_{ex}$=470±20 nm, $\lambda_{em}$=535±22.5 nm, and DC ~500 nm. The efficiency of transfection is the number of cells expressing the GFP divided by the total number of cells.

C. Results and Discussion

1. SPLP-CPL$_4$ Aggregate Following Insertion of CPL4 and De-aggregate Following Addition of Divalent Cations.

Figure 31:
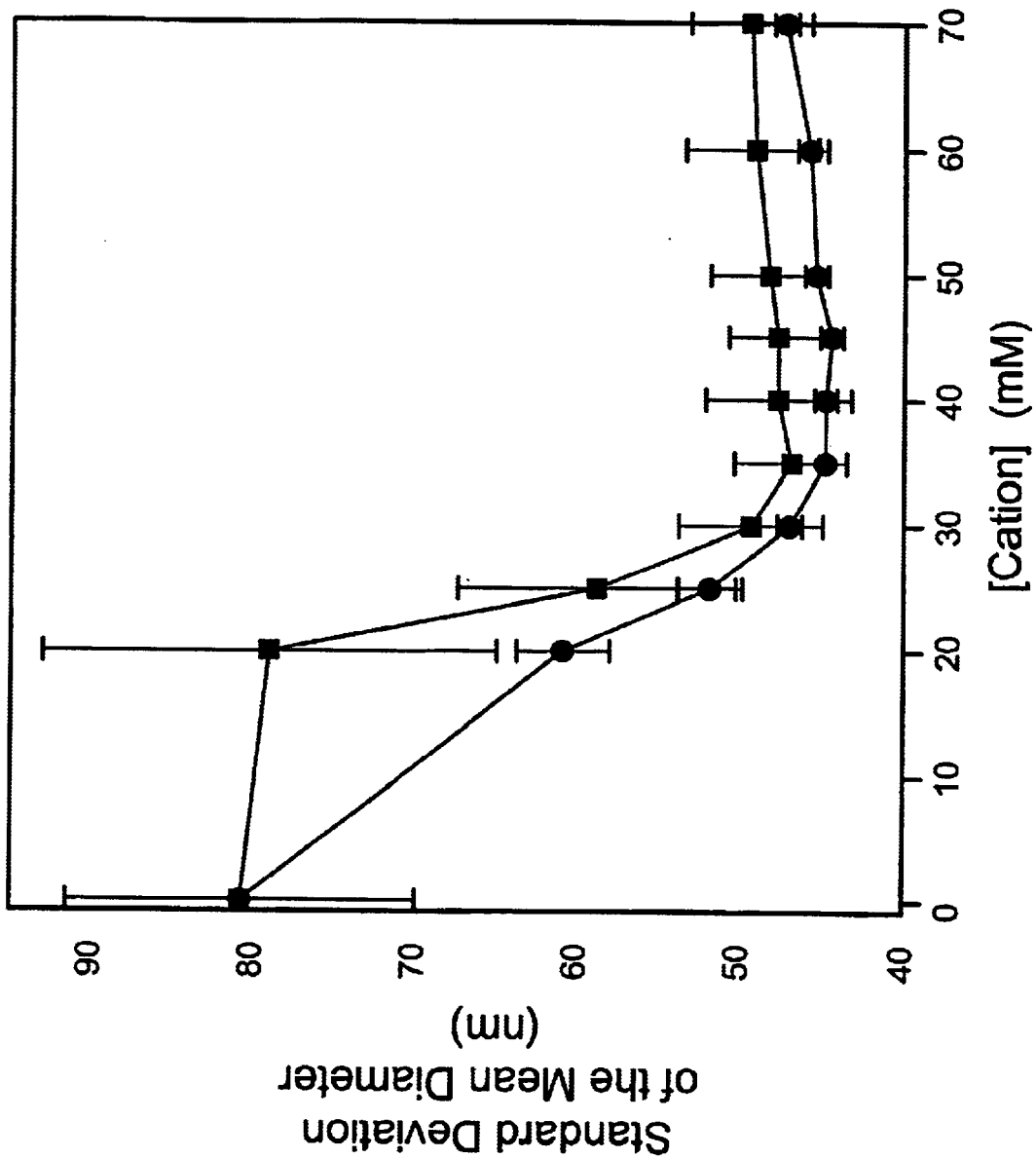
FIG. 31 illustrates an effect of cation concentration on the deaggregation of SPLP-$CPL_4$. The mean diameter and standard deviation of the particles in the presence of increasing [Cation], $Ca^{2+}$ (●) and $Mg^{2+}$ (■), from 0 mM to 70 mM, was measured using quasi-elastic light scattering (QELS). To ~180 nmol of SPLP-$CPL_4$ in 400 mL in a Nicomp tube was added small quantities of either $CaCl_2$ or $MgCl_2$ (500 mM stock solutions). Measurement of the mean diameter±standard deviation of the particles in the presence of differing amounts of the cation were made using a Nicomp Model 270 Submicron Particle Sizer. The diameters of the particles do not dramatically change, however, the Gaussian distributions do get broader. Thus, the standard deviations were used as a measure of deaggregation with smaller deviations indicating less aggregation.

LUV containing CPL tend to aggregate, and that this aggregation can be inhibited by increasing the ionic strength of the medium. It was found that SPLP-CPL$_4$ were also susceptible to aggregation, and that this aggregation could be reversed by adding NaCl, CaCl$_2$ or MgCl$_2$ to the SPLP-CPL$_4$ formulation. This effect is illustrated in FIG. 31 which shows the effect of the addition of CaCl$_2$ and MgCl$_2$ on aggregation of SPLP-CPL$_4$ as monitored by the change in the standard deviation of the mean diameter of the particles measured by quasi-elastic light scattering (QELS). For both cations the standard deviation decreases with increasing cation concentration with optimal de-aggregation occurring above 30 to 40 mM. This behavior could also be visualized by freeze-fracture electron microscopy. Freeze-fracture micrographs of SPLP reveal small monodisperse particles, whereas SPLP-CPL$_4$ prepared in the absence of CaCl$_2$ are highly aggregated. The addition of 40 mM CaCl$_2$ reverses this aggregation to produce monodisperse particles similar to the SPLP preparation. For details of sample preparation and electron microscopy, (see, Wheeler et al., *Gene Therapy*; 6:271–281 (1999)).

The sizes of SPLP and SPLP-CPL$_4$ in the presence of CaCl$_2$ were compared using QELS and freeze-fracture electron microscopy. QELS studies revealed the mean diameter of SPLP and SPLP-CPL$_4$ to be 80±19 nm and 76±15 nm, respectively, whereas the freeze-fracture studies indicated to diameters of 68±11 nm and 64±14 nm. These values for SPLP are in close agreement with previous studies.

2. Chemical Composition and Stability of SPLP-CPL4.

The lipid composition of SPLP-CPL$_4$ and SPLP are given in Table 9 below:

TABLE 9

Loss of PEG-CerC$_{20}$ from SPLP following CPL$_4$ insertion.

| | [DOPE] (mM) | [PEG-CerC$_{20}$] (mM) | DOPE: PEG-C$_{20}$ | % PEG-CerC$_{20}$ after insertion |
|---|---|---|---|---|
| | 0.786 | 0.0714 ± 0.0004 | 11.0 ± 0.1 (81.6:7.4; mol) | 79.7 ± 0.9% |
| SPLP-CPL$_4$ | 0.790 ± 0.007 | 0.0572 ± 0.0003 | 13.8 ± 0.1 (81.6:x; mol) | (x = 5.9 ± 0.1 mol %) |

By analysis of the SPLP itself, the molar ratio of DOPE:PEG-CerC$_{20}$ was 11.0(±0.1):1. This corresponds to a system of DOPE:PEG-CerC$_{20}$:DODAC of (81.6:10.9:7.4). From the results, 79.7±0.9% of the PEG-CerC$_{20}$ remains following CPL$_4$ insertion. This corresponds to a final mol % of PEG-CerC$_{20}$ of 5.9±0.1 mol %. This means that about 1.5±0.1 mol % of PEG-CerC$_{20}$ was replaced during the insertion of CPL$_4$. If we assume that on the inner leaflet and outer leaflet the same amount of PEG-CerC$_{20}$ is initially present at 7.4 mol %, the outer leaflet will possess 4.4±0.1 mol % of PEG-CerC$_{20}$ after insertion. Since we inserted ~4.5 mol % CPL$_4$ into SPLP (9.0 mol % in the outer leaflet), resulting in a total of 13.4±0.1 mol % of total PEG in the outer leaflet.

The stability of SPLP and SPLP-CPL$_4$ in 50% mouse serum for up to 4 hours. In all cases, the DNA was completely protected from serum degradation.

3. SPLP-CPL$_4$ Exhibit Enhanced Uptake into BHK Cells and Dramatically Enhanced Transfection Potency.

Figure 32:
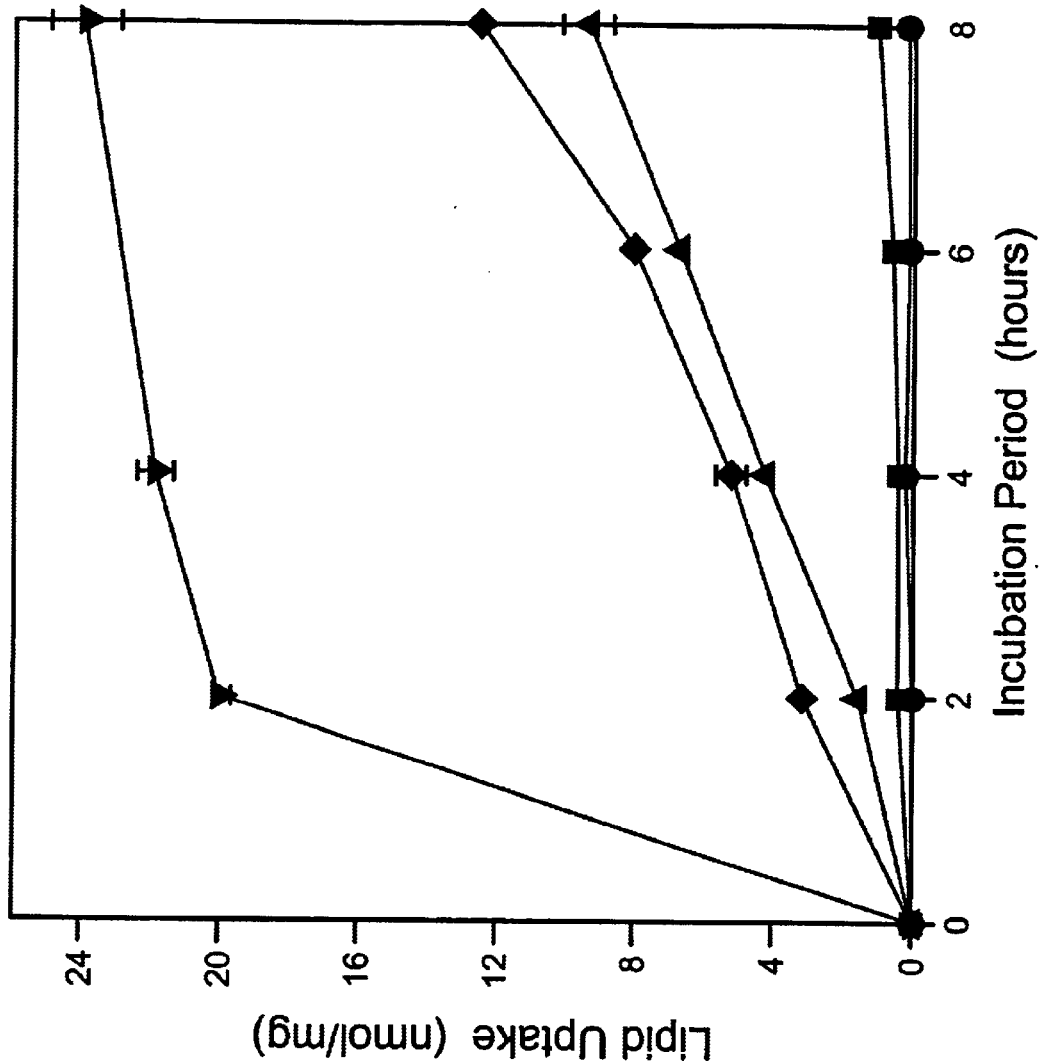
FIG. 32 illustrates uptake of SPLP containing various percentages of $CPL_4$. Panel A. Time course for the uptake of 20 μM SPLP possessing 0 mol % (-), 2 mol % (■), 3 mol % (▲), or 4 mol % (♦) $CPL_4$ and DOPE:DODAC complexes (▼) by BHK cells. The insertion of the $CPL_4$ into SPLP and the preparation of complexes was performed as described herein The mol % of $CPL_4$ in the SPLP-$CPL_4$ was also determined, as described herein. BHK cells were plated in 12-well plates at $1\times10^5$ cells/well. To 200 μL of sample (containing SPLP-$CPL_4$ or complex+$CaCl_2$) was added 800 μL of DMEM+10% FBS. The resulting $CaCl_2$ concentration was diluted to 20% of the original. Following incubation periods of 2, 4, 6 and 8 hours, the cells were lysed with 600 mL of lysis buffer and the rhodamine fluorescence and BCA assays were measured for the lysate, as described herein (see FIG. 21).

The next set of experiments was aimed at determining the influence of incorporated CPL$_4$ on the uptake of SPLP into BHK cells and the resulting transfection potency of the SPLP-CPL$_4$ system. SPLP containing up to 4 mol % CPL$_4$ were prepared in the presence of 40 mM CaCl$_2$ and were added to BHK cells (final CaCl$_2$ concentration 8 mM) and incubated for varying times. The cells were then assayed for associated SPLP-CPL$_4$ as indicated in Methods. As shown in FIG. 32, uptake of SPLP that contain no CPL$_4$ is minimal even after 8 h of incubation, however uptake is dramatically improved for SPLP containing 3 mol % or higher levels of CPL$_4$. For example, SPLP containing 4 mol % CPL$_4$ exhibit accumulation levels at 8 h that are approximately 50-fold higher than achieved for SPLP. This enhanced uptake can be visually detected using fluorescence micrographs of BHK cells following incubation with rhodamine-labeled SPLP and SPLP-CPL$_4$ for 4 h. The presence of 4 mol % CPL$_4$ clearly results in improved levels of cell-associated SPLP.

Figure 33:
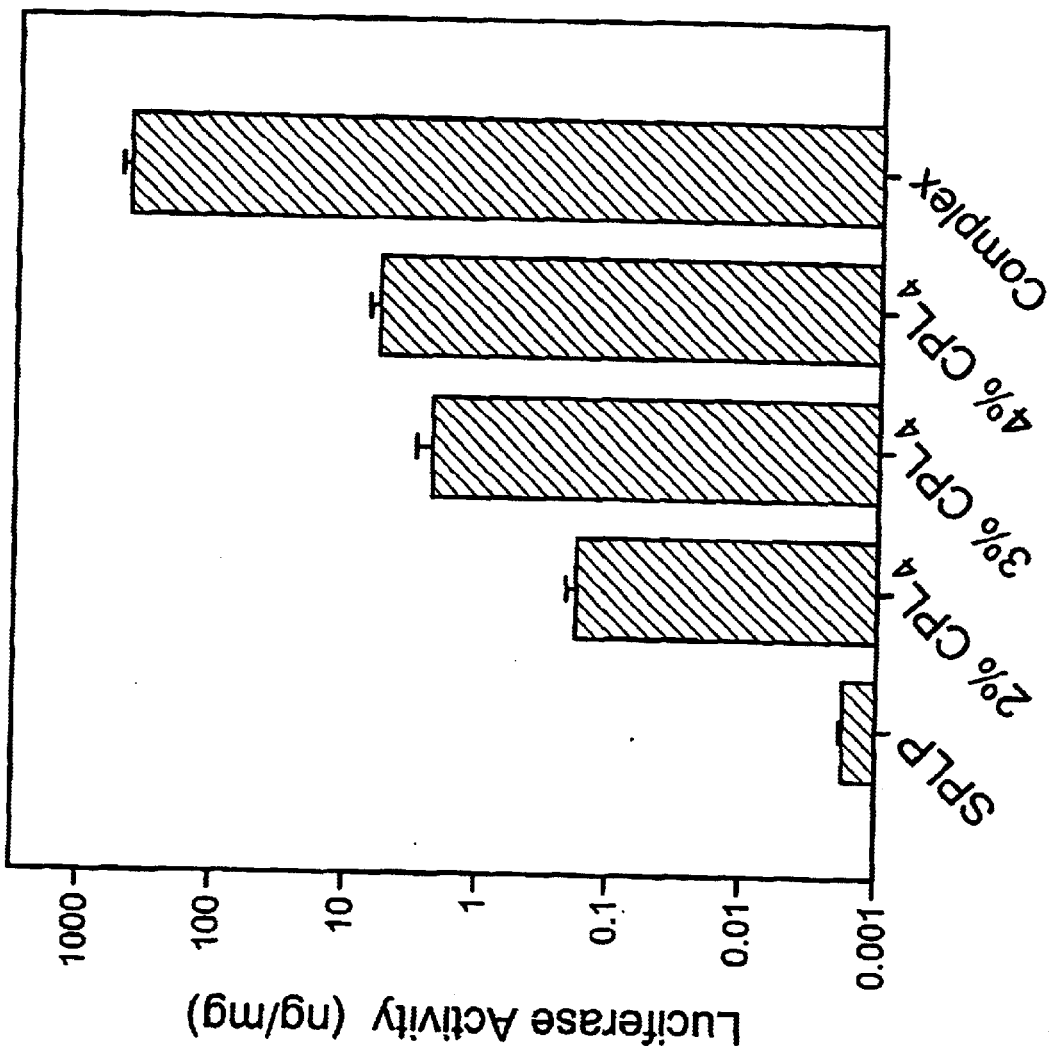
FIG. 33 illustrates tansfection of BHK cells by SPLP (5.0 μg/mL pLuc) following insertion of various mole percentages of $CPL_4$ (2, 3, and 4 mol %). The $CPL_4$ was inserted into SPLPs using the procedure described herein. As a comparison, SPLP (0 mol % CPL) and DOPE:DODAC (1:1) complex transfections were also performed. BHK cells were plated at $1\times10^4$ in 96-well plates. Transfections were carried out by incubating the samples [20 μL (SPLP-$CPL_4$+$CaCl_2$)+ 80 μL of complete media] on the cells for 4 hours followed by a 24 hour complete incubation. The $CaCl_2$ concentration again is diluted to 20% of the original concentration. Following the 24 hour incubation, the cells were lysed with lysing buffer and the luciferase and BCA assays were performed (see FIG. 22).

The transfection properties of SPLP, SPLP-CPL$_4$ and plasmid DNA-cationic lipid complexes (DODAC/DOPE; 1:1; 1.5:1 +ve/−ve c.r.) were examined using the incubation protocol usually employed for complexes. This consisted of incubation of 10$^4$ BHK cells with SPLP, SPLP-CPL$_4$ and complexes containing 0.5 μg pCMVLuc for 4 h, followed by removal of SPLP, SPLP-CPL$_4$ or complexes that are not associated with the cells, replacement of the media, incubation for a further 20 h and then assaying for luciferase activity. The SPLP-CPL$_4$ preparations contained 7 mM CaCl$_2$ in the incubation medium. As shown in FIG. 33, the presence of the CPL$_4$ resulted in dramatic increases in the transfection potencies of the SPLP system. SPLP-CPL$_4$ containing 4 mol % CPL$_4$ exhibited luciferase expression levels some 3×10$^3$ higher than achieved with SPLP. (see, Mok et al., *Biochim Biophys Acta*, 1419:137–150 (1999)).

Ca2+ is Required for Transfection Activity of SPLP-CPL$_4$.

Figure 34:
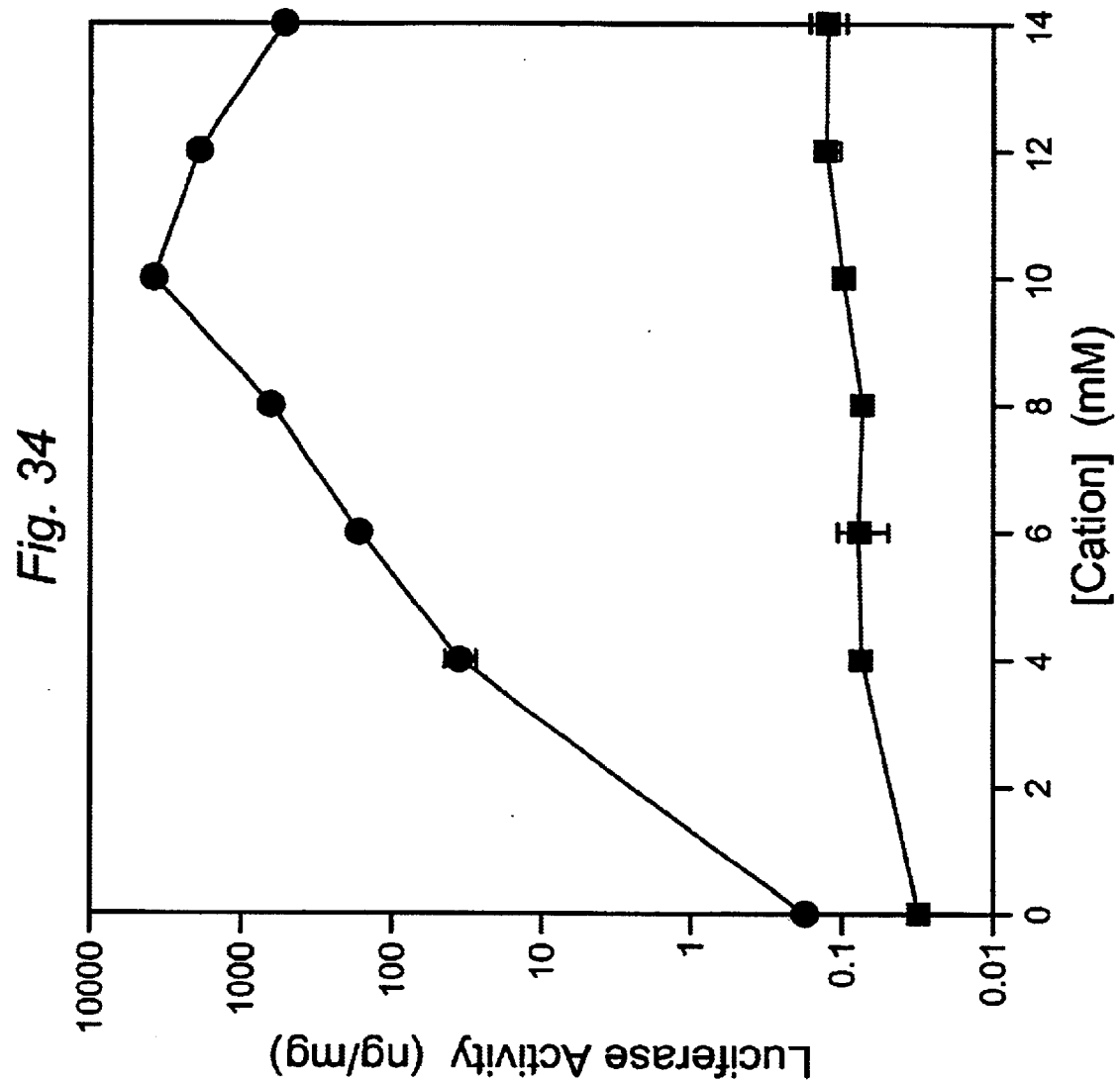
FIG. 34 illustrates the effect of [Cation], $Ca^{2+}$ (●) and $Mg^{2+}$ (■), on the transfection of SPLP-$CLP_4$ (5.0 μg/mL pLuc) on BHK cells. SPLP-$CPL_4$+$CaCl_2$ or $MgCl_2$ was mixed with DMEM+10% FBS and the mixtures were applied to $1\times10^4$ BHK cells plated in a 96-well plate. Following a complete 48 hour incubation, the transfection media was removed and the cells were lysed with lysing buffer and the luciferase activity and protein content were measured as described earlier.

It was of interest to determine the influence of Ca$^{2+}$ on the transfection activity of SPLP-CPL$_4$. SPLP containing 4 mol % CPL$_4$ were incubated with BHK cells for 48 h in the presence of 0–14 mM MgCl$_2$ and CaCl$_2$ and the luciferase activities then determined. As shown in FIG. 34, the transfection activity was influenced by the presence of Ca$^{2+}$ in the transfection medium. At the optimum CaCl$_2$ concentration of 10 mM, SPLP-CPL$_4$ exhibited transfection potencies that were more than 10$^4$ times higher than if MgCl$_2$ was present.

Figure 35:
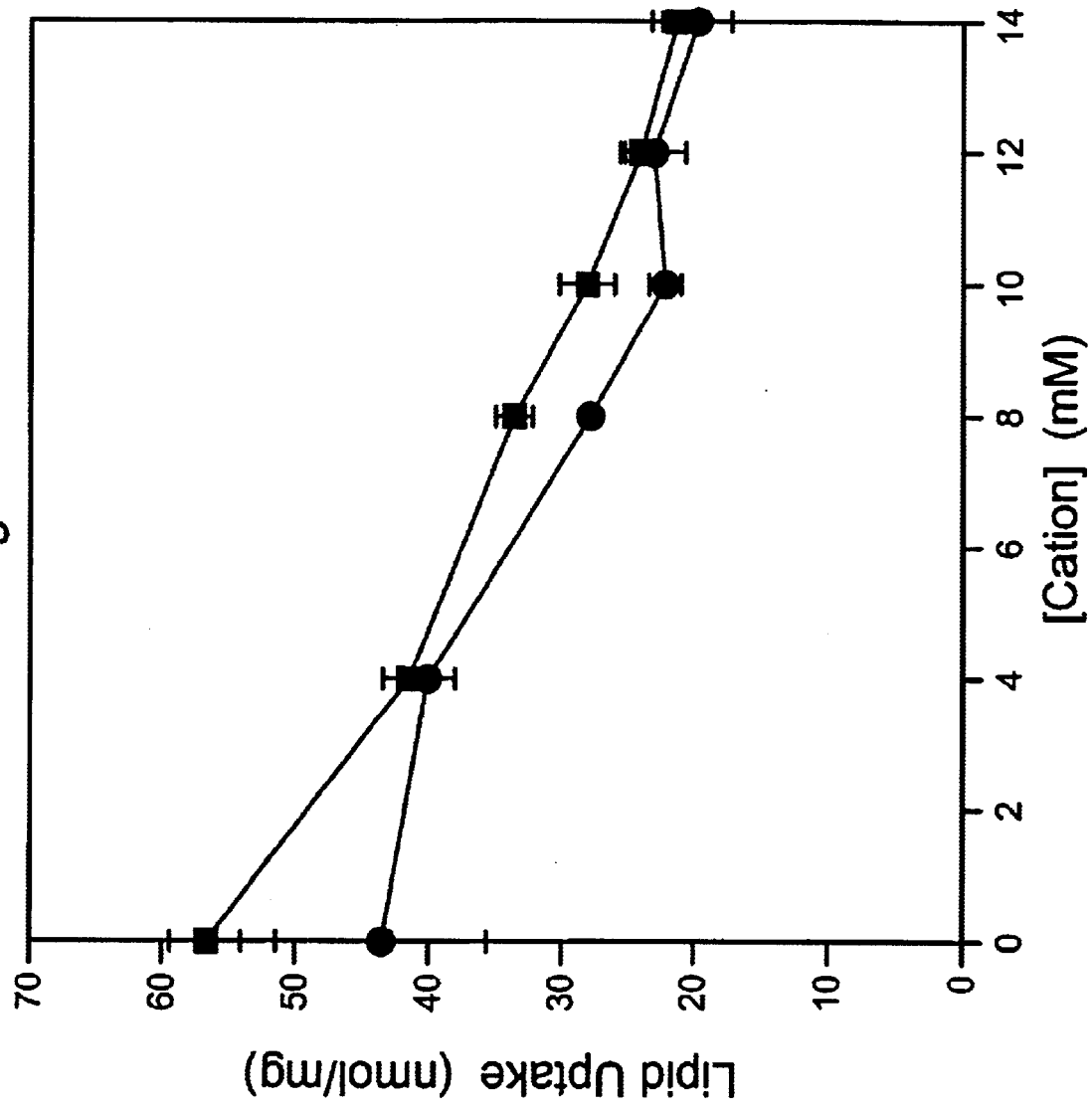
FIG. 35 illustrates the effect of [Cation], $Ca^{2+}$ (●) and $Mg^{2+}$ (■), on the lipid binding and uptake of 80 μM SPLP-$CPL_4$ on BHK cells. The samples possessing varying concentrations of the cation (0–14 mM final concentration) were incubated on $1\times10^5$ BHK cells for 4 hours at which time the cells were lysed and the rhodamine fluorescence and protein content were measured.

Uptake of SPLP-CPL$_4$ into BHK cells was monitored following a 4 h incubation in the presence of 0–14 MM MgCl$_2$ and CaCl$_2$. As shown in FIG. 35 the amount of SPLP-CPL$_4$ taken up by BHK cells is the same for both Mg$^{2+}$ and Ca$^{2+}$ containing media. The uptake of the SPLP-CPL$_4$ decreases as the concentration of divalent cations increases, which likely arises due to shielding of the negatively charged binding sites for the CPL$_4$ on the surface of the BHK cells.

5. SPLP-CPL$_4$ Exhibit Transfection Potencies in vitro that are Comparable to or Greater than Achieved Using Complexes.

Figure 36:
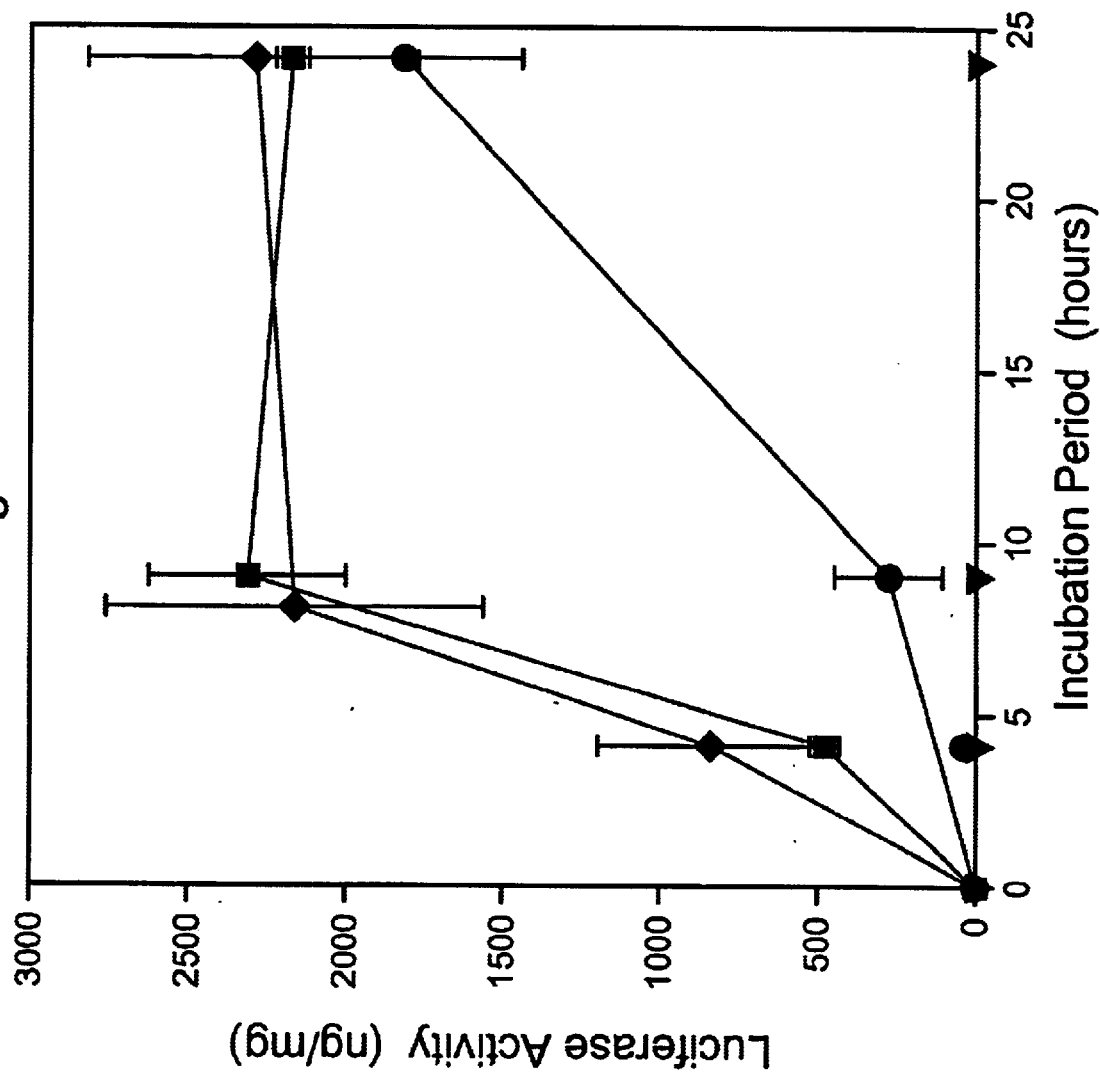
FIG. 36 illustrates transfection of SPLP-$CPL_4$, SPLP and complexes (each containing 5.0 μg/mL pCMVLuc) at longer time points. Transfection of SPLP-$CPL_4$ (4 mol % $CPL_4$)+ 40 $mM_{initial}$ $CaCl_2$ (●), SPLP (▼), DOPE:DODAC complexes (■), and Lipofectin complexes (♦) was performed on $1\times10^4$ BHK cells. The transfection media was incubated on the cells for 4, 8 or 24 hours, after which the transfection media was replaced by complete media for the 4 and 8 hour timepoints. Then at a total incubation time of 24 hours (20, 16, and 0 hours, respectively, after removal of the transfection media), the cells were lysed and the luciferase activity and protein content were measured.

The results shown in FIG. 33 indicating that complexes give rise to ~100-fold higher levels of transfection than SPLP-CPL$_4$ were obtained for a fixed 4 h incubation time with the BHK cells, followed by a 20 h hold time to achieve maximum expression. Given that the SPLP-CPL$_4$ are stable systems it is likely that uptake into the BHK cells would continue over extended time periods. The transfection levels achieved when the incubation time of the SPLP-CPL$_4$ and the complexes with the BHK cells was extended to 8 and 24 h, followed by hold times of 16 and 0 h respectively were examined. Two types of plasmid DNA-cationic lipid complexes were used, namely DOPE:DODAC (1:1) complexes (1.5:1, c.r.) and complexes obtained using the commercial transfection reagent Lipofectin (DOPE/DOTMA [1:1] complexes, 1.5:1 c.r.). As shown in FIG. 36, the transfection potency of the SPLP-CPL$_4$ increases markedly with increased incubation times, suggesting that a limiting factor for transfection achieved at a 4 h incubation time was the rate of uptake of the SPLP-CPL$_4$ system. At the 24 h incubation time transfection levels are achieved that are comparable to those achieved by Lipofectin or DOPE/DODAC complexes.

Figure 37A:
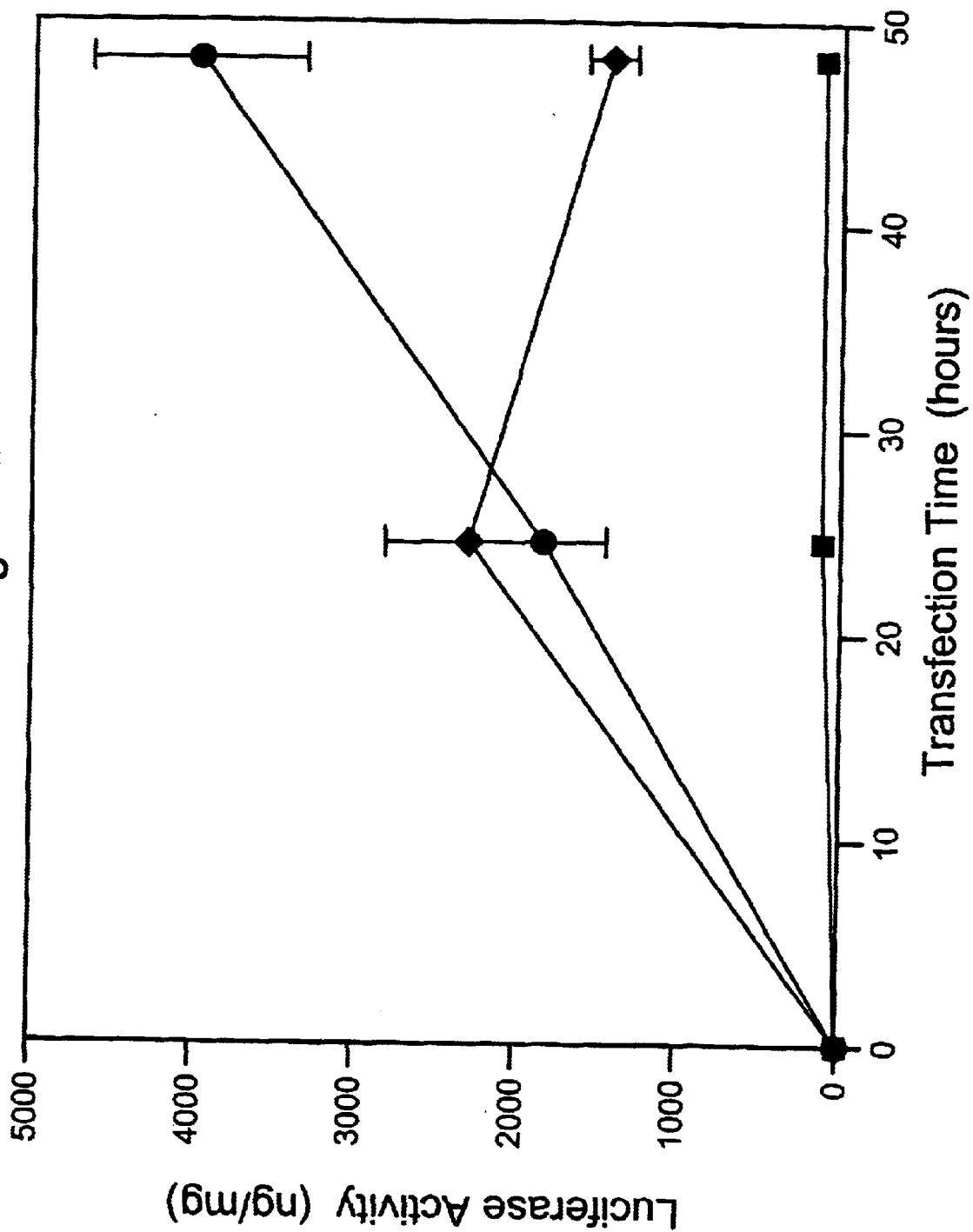
FIGS. 37A–37B illustrate transfection potency and toxicity of SPLP-$CPL_4$ compared to Lipofectin complexes. A. Transfection activity for SPLP-$CPL_4$+$CaCl_2$ (●), SPLP (■), and Lipofectin (♦) on $1\times10^4$ BHK cells incubated for 24 and 48 hours followed by immediate cell lysis, and measurement of luciferase activity and protein content. B. Measurement of the cellular survival following 24 and 48 hour incubations of the SPLP-$CPL_4$+$CaCl_2$ (●), Lipofectin (♦), and DOPE/ DODAC (1:1) complexes on $1\times10^4$ BHK cells. Following incubation, the cells were lysed and the protein content from the BCA assay was used as a measure of protein survival.

Further experiments were conducted to determine transfection levels after 24 and 48 h incubation times with luciferase activities assayed immediately following the incubation period. As shown in FIG. 37A the activity of Lipofectin (DOPE/DOTMA; 1:1) complexes leveled off at ~2000 ng/mg after 24 h. In contrast the activity of SPLP-CPL$_4$ formulation continued to increase as the incubation time was increased, achieving luciferase expression levels corresponding to 4000 ng/mg at 48 h. This activity is approximately 10$^6$ times higher than observed for SPLP (in the absence of Ca$^{2+}$) and almost double the levels that can be achieved by Lipofectin complexes. Similar results were obtained for the DOPE:DODAC complexes.

6. SPLP-CPL4 are Non-toxic and Efficient Transfection Agents.

Figure 37B:
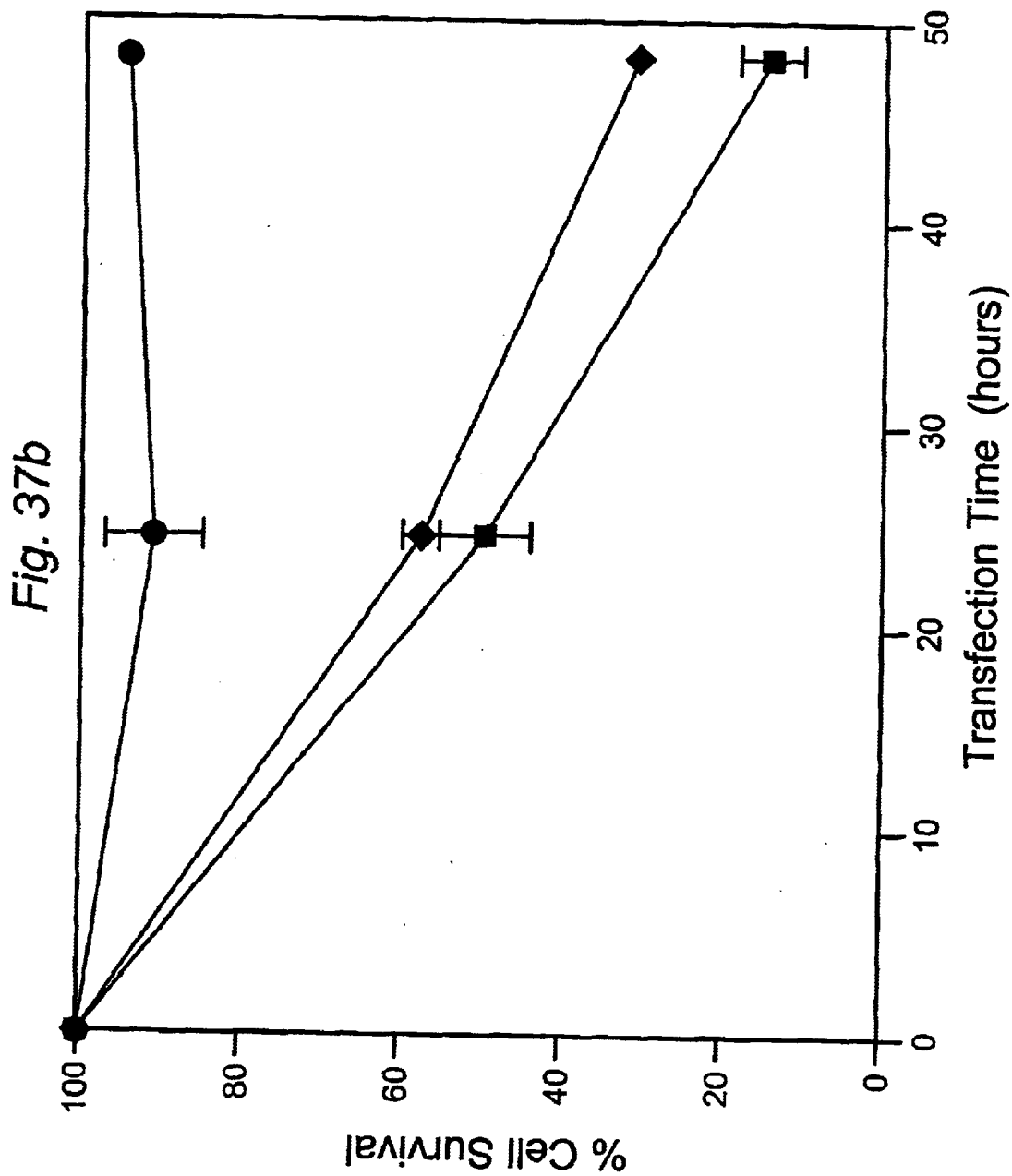

It is well known that plasmid DNA cationic lipid complexes can be toxic to cells. The SPLP-CPL$_4$ contain low levels of cationic lipid and are potentially less toxic than complexes. The toxicity of SPLP-CPL$_4$ and complexes was assayed by determining cell viability following a 48 h exposure to levels of SPLP-CPL$_4$ and complexes corresponding to 0.5 μg plasmid and ~30 nmol total lipid. As shown in FIG. 37B, SPLP-CPL$_4$ exhibit little if any toxicity. Cell survival was only 30% after a 48 h incubation with Lipofectin complexes whereas ~95% of the cells were viable following a 48 hour incubation with SPLP-CPL$_4$.

The efficiency of transfection, indicated by the proportion of cells transfected by a vector, is also an important parameter. The proportion of cells transfected were estimated using plasmid carrying the green fluorescent protein (GFP) gene. Transfection was detected by expression of the fluorescent protein inside a cell employing fluorescence microscopy. As shown in FIGS. 37A and 38B, approximately 35% of the cells at 24 h and 50% at 48 h were transfected by SPLP-CPL$_4$, with no apparent cell death. In contrast, Lipofectin complexes exhibit maximum transfection efficiencies of less than 35% and only ~50% cell survival after the 24 h transfection period. Similar low transfection efficiencies and high toxicities were also seen with DOPE:DODAC complexes.

The results of this study demonstrate that the incorporation of CPL$_4$ into SPLP results in improved uptake into BHK cells and a dramatically enhanced transfection potency of SPLP when Ca$^{2+}$ is present. There are three points of interest. The first concerns the chemical composition and structure of the SPLP-CPL$_4$ system and the generality of the post-insertion procedure for modifying the trophism and transfection potency of SPLP. The second concerns the relation between enhanced uptake of SPLP, the presence of Ca$^{2+}$ and the transfection activities observed. Finally, it is of interest to compare the properties of the SPLP-CPL$_4$ system with plasmid DNA-cationic lipid complexes.

The second point of discussion concerns the mechanism whereby CPL$_4$ increases the transfection potency of the SPLP system. Clearly the presence of the CPL$_4$ increases the uptake of SPLP into the BHK cells, however the increase in transfection potency is almost entirely dependent on the additional presence of Ca$^{2+}$. It may be noted that, following an 8 h incubation, the presence of 4 mol % CPL$_4$ increases the uptake of SPLP into BHK cells by approximately 50-fold, whereas the transfection potency (in the presence of Ca$^{2+}$) is increased by a factor of ~10$^4$. Previous work conducted on SPLP has shown that the presence of Ca$^{2+}$ results in a maximum increase in transfection potency of ~600 and that this increase in potency results from an ability of Ca$^{2+}$ to assist in destabilizing the endosomal membrane following uptake, rather than an increase in uptake itself. In turn, this suggests that the improvement in transfection potency for the SPLP-CPL$_4$ system over the SPLP system arises from the CPL$_4$-dependent increase in uptake multiplied by the Ca$^{2+}$-dependent improvement in intracellular delivery following uptake.

The final area of discussion concerns the advantages of the SPLP-CPL$_4$ system over other non-viral vectors, which include the well-defined modular nature of the SPLP-CPL$_4$ system as well as toxicity and potency issues. First, the well-characterized nature of the SPLP-CPL$_4$ as small, homogeneous, stable systems containing one plasmid per particle contrast with non-viral systems such as plasmid DNA-cationic lipid complexes which are large, inhomogeneous, unstable systems containing ill-defined numbers of plasmids per complex. An important point is that SPLP are basic components of more sophisticated systems, such as SPLP-CPL$_4$, which can be constructed in a modular fashion. For example, post-insertion of PEG-lipids which contain specific targeting ligands in place of the cationic groups of CPL should result in SPLP that are specifically targeted to particular cells and tissues. With regard to toxicity, it is clear that SPLP-CPL$_4$ are markedly less toxic to BHK cells in tissue culture. This is presumably related to the low proportions of cationic lipid contained in SPLP as compared to complexes. The transfection potency and efficiency of SPLP-CPL$_4$ is clearly comparable to the levels that can be achieved with complexes. It should be noted that this finding suggests that models of transfection by complexes that involve.

In the present example, the superiority of SPLP-CPL$_4$ compared to commercially available complex systems (e.g. Lipofectin) has been demonstrated. Thus, a synthetic virus has been developed that will have high transfection potency but none of the problems associated with viruses. Many points can be made to corroborate these statements. The first point revolves around the placement of the charge. Whereas on complexes the charges are located on the surface of the lipid bilayer, the SPLP-CPL$_4$ possess charges on the vesicle surface which are localized a good distance from the liposomal surface, above the protective PEG coating which surrounds the liposome. In the case of the complexes, proteins binding to the liposome surface can lead to recognition and clearance by macrophages of the RES. (see, Chonn et al., *J Biol Chem*; 267:18759–18765 (1992)) In the SPLP-CPL$_4$, the charge on the surface of the bilayer is protected by the PEG coating, such that this should not occur. However, the charge on the SPLP-CPL$_4$ will allow the association of the liposomes with cells resulting in eventual uptake and transfection.

The size and serum stability of the SPLP-CPL$_4$ compared to complexes are important parameters for effective gene delivery systems, especially if one wishes to approach the capabilities of viral systems. The SPLP-CPL$_4$ have been shown here to be of relative small size (~100 nm) compared to complexes, which are frequently on the order of microns in diameter. The small size should allow for accumulation at sites with larger fenestration (e.g. tumors, and inflammation sites). (see, Kohn et al., *Lab Invest*; 67:596–607 (1992)). As stated earlier, DNA in the SPLP-CPL$_4$ was shown to be protected from the external environment (i.e. inaccessible to degradation by DNase within serum), whereas DNA in complexes is susceptible to DNase. (see, Wheeler et al., *Gene Therapy*; 6:271–281 (1999)).

Viruses (see, Hermonat et al., *Proc. Natl. Acad. Sci. USA*; 81:6466–6470 (1984); Lebkowski et al., *Molec Cell Biol*; 8:3988–3996 (1988); Keir et al., *J Neurovirology*, 3:322–330 (1997)] and lipid/DNA complexes (see, Feigner et al., *Proc Natl Acad Sci USA*, 84:7413–7417 (1987); Feigner et al., *J Biol Chem*; 269:2550–61 (1994); Hofland et al., *Proc Natl Acad Sci USA*; 93:7305–7309 (1996); Bebok et al., *J Pharm Exp Ther*; 279:1462–1469 (1996); Gao et al., *Gene Therapy*; 2:710–722 (1995)) have been shown to possess high in vitro transfection potencies. It therefore reasons that the SPLP-CPL$_4$ system, if it is to attain viral qualities, should be capable of attaining these high transfections. This has actually been achieved by the SPLP-CPL$_4$ system on BHK cells, with transfection levels reaching a factor of two higher than a commercially available complex system (i.e. Lipofectin). This is a huge improvement over SPLP, which showed only a small amount of transfection.

Efficient systemic delivery and transfection of genetic drugs are achieved using this SPLP-CPL$_4$ system due to the above benefits. Very high transfections in vitro with SPLP-CPL$_4$ have been achieved. In addition, a system wherein the positioning of the positive charges on the CPL, so that the PEG of the PEG-Cer initially masks it. This is achieved by the synthesis of DSPE-PEG-CPL$_4$ with a shorter PEG moiety. This allows for its accumulation at disease sites followed by the controlled release of the PEG-Cer, exposing the positive charges to the surrounding cells.

Example X

This example shows transfection rates of BHK cells by long- versus short-chained CPLs.

Figure 38:
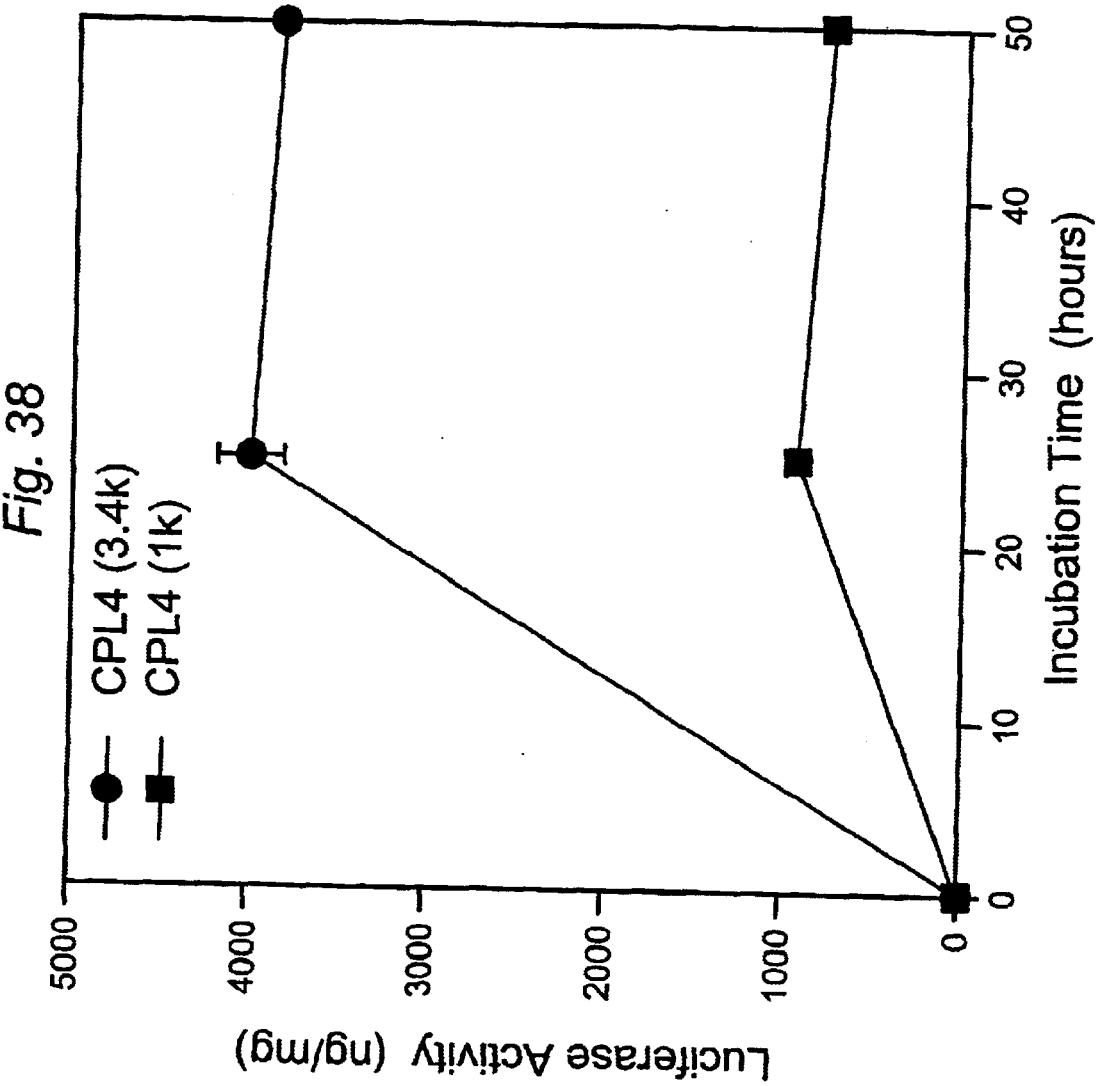
FIG. 38 illustrates the transfection of BHK cells using both long and short chained CPLs. The presence of the short chained PEG in the CPL results in a decrease by a factor of about 4 compared to the transfection by the long chained CPL.

Using synthesis methods from above, CPL (PEG 3.4k) and CPL(PEG 1k) were generated and each inserted into a separate SPLP system containing PEG-$_{2000}$-Cer C20 as described above. FIG. 38 illustrates transfection rates of the CPLs having a PEG 3.4k versus a CPL having a PEG 1k. The short-chained PEG in the CPL results in a decrease by a factor of about 4 compared to the transfection by the long chained CPL. Without being bound by any particular theory, it is believed that the long chain CPL (PEG$_{3400}$) sticks out above the surface, whereas the short chain CPL (PEG$_{1000}$) is buried (masked) in the surface of the SPLP. The reduced in vitro transfection of the short chain CPL clearly suggests that it has improved in vivo circulation.

Example XI

This example shows that CPL8 behaves similar to CPL4 with respect to insertion into LUVs, and that transfection can be achieved with CPL8-LUV systems.

TABLE 10

Insertion of CPL$_8$ in SPLP and LUV.

| SPLP | Initial mol % CPL$_8$ | % Insertion | Final mol % CPL$_8$ |
|---|---|---|---|
| | 1.11 | 97% | 1.07 |
| | 1.39 | 85% | 1.19 |
| | 1.67 | 95% | 1.60 |
| | 1.94 | 87% | 1.70 |
| LUV | Initial mol % CPL$_8$ | % Insertion | Final mol % CPL$_8$ |
| | 1.05 | 79% | 0.82 |
| | 1.39 | 71% | 0.99 |
| | 1.74 | 76% | 1.32 |
| | 2.11 | 89% | 1.88 |

The insertions of the CPL$_8$ into LUV and SPLP is very similar to what was observed for the insertions of CPL$_4$. For the transfection and uptake of these particles on BHK cells, variable results are obtained, with the CPL$_8$ performing better than the CPL$_4$ sometimes and vice versa at other times.

Example XII

In this in vitro example using mouse neuroblastoma cell line Neuro-2a (ATCC-CCL-131), the SPLP-CPL4[1k] is used to determine gene expression with respect to varying Ca$^{2+}$ concentrations and to compare to gene expression using a standard SPLP (PEG-CerC20 10%: CPL$_4$[1k] 4%; and other components; DNA:lipid ratio=0.05).

5×10$^4$ cells/well are plated in 24-well plates in 1 mL of complete media (MEM(Eagle)) with non-essential amino acids and Hanks' buffered salt solution with 10% FBS. Plates are incubated overnight at 37° C. with 5.0% CO$_2$. To each group set out below is added 500 µL transfection media in triplicate.

TABLE 11

| GROUP | SPLP or SPLP-CPL (µg) | [Ca2+] (250 mM)(µL) | Complete Media (µL) |
|---|---|---|---|
| A (0 mM Ca2+) | 2.5 | 0 | 1980 |
| B (2 mM Ca2+) | 2.5 | 48 | 1932 |
| C (4 mM Ca2+) | 2.5 | 96 | 1884 |
| D (6 mM Ca2+) | 2.5 | 144 | 1836 |
| E (8 mM Ca2+) | 2.5 | 192 | 1788 |
| F (10 mM Ca2+) | 2.5 | 240 | 1740 |
| G (12 mM Ca2+) | 2.5 | 288 | 1692 |
| H (14 mM Ca2+) | 2.5 | 336 | 1644 |

2.5 µg DNA is added per well in fully encapsulated SPLPs (0.5 mL total solution). Plates are incubated for 8 hrs. Transfection media is removed. 1 mL of complete media is added back. Cells are incubate for another 24 hrs at 37° C., 5.0% CO$_2$.

For analysis, media is removed from cells and they are washed 2× with PBS then frozen at −70° C. Cells are lysed with 150–200 µL 1×CCLR; then shaken 5 minutes on plate shaker. 20 µL lysate is transferred to a 96-well luminescence plate. Plates are read to determine luciferase activity.

Figure 39:
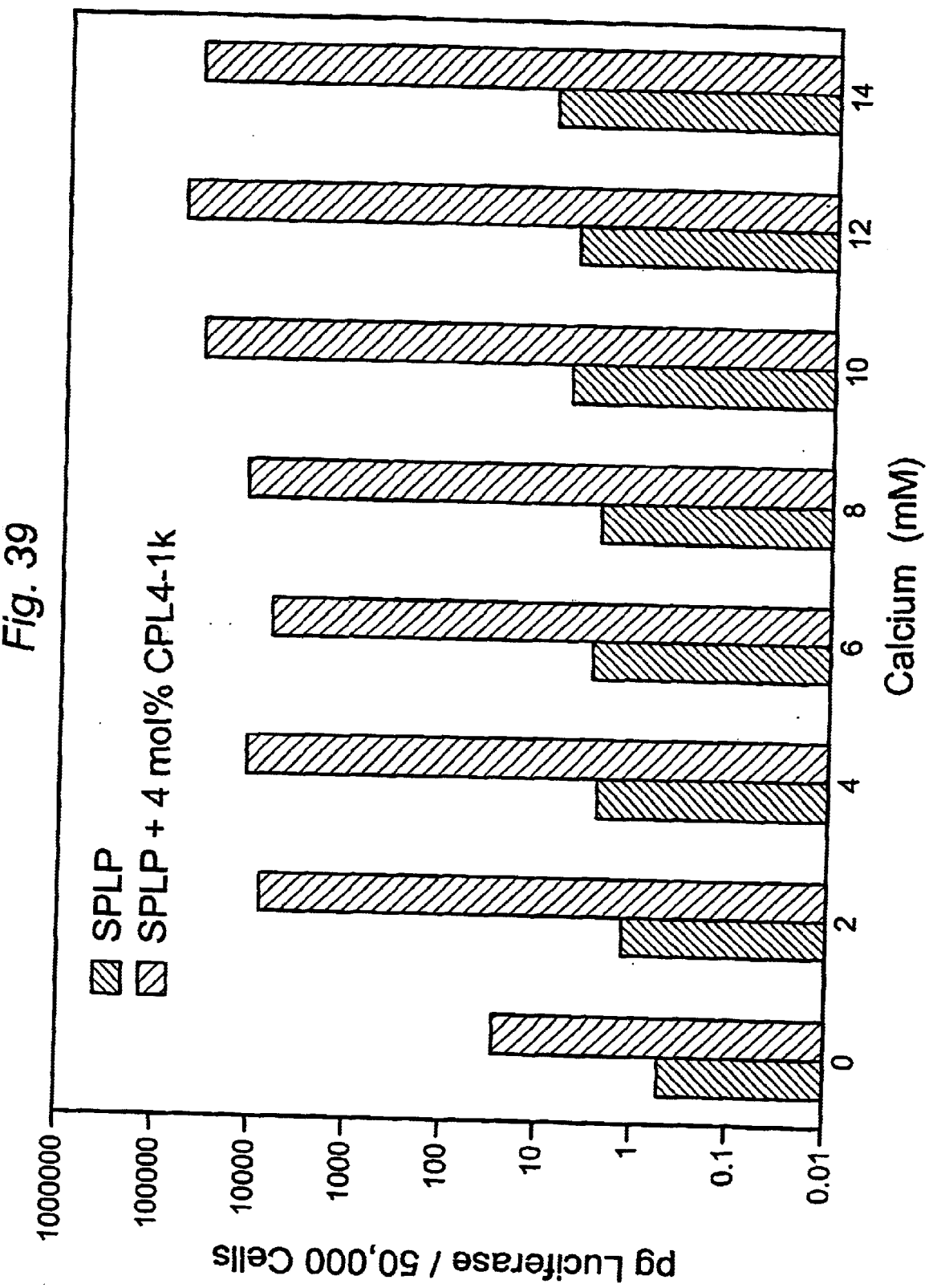
FIG. 39 illustrates the transfection of Neuro-2a cells. SPLP+4 mol % CPL4-1k produces 4 orders of magnitude of gene expression more than SPLP alone in Neuro-2a cells.

The results are shown in FIG. 39. As shown therein, SPLP+4 mol %CPL4-1k produces 4 orders of magnitude of gene expression more than SPLP alone in Neuro-2a cells. Effects of calcium are not considered to be significant in this experiment. The amount of luciferase produced remains the same from 2–14 mM Ca2+.

Example XIII

This in vivo example discloses pharmacokinetics and biodistribution of CPL$_4$-1-k LUVs (SPLPs containing short chain CPLs) in C57/b16 mice. Different SPLP formulations containing increasing amounts of CPL-4-1k are assayed in vivo to determine optimal clearance characteristics.

CPL$_4$-1k SPLPs are prepared according to previous protocols. Before use, all samples are characterized to determine actual composition prior to administration. All samples are filter sterilized prior to dilution to working concentration. All samples are to provided in sterile crimp top vials. All vials are labeled with the formulation date, lipid composition, and specific activity. $^3$[H]CHE is incorporated at 1 µCi/mg Lipid. The following formulations are made and analyzed:

| A: | $^3$[H]CHE-LUV | DOPE:DODAC:PEGC20::84:6:10 |
| B: | $^3$[H]CHE-LUV | DOPE:DODAC:PEGC20::84:6:10 + 1 mol % CPL-4-1k |
| C: | $^3$[H]CHE-LUV | DOPE:DODAC:PEGC20::84:6:10 + 2 mol % CPL-4-1k |
| D: | $^3$[H]CHE-LUV | DOPE:DODAC:PEGC20::84:6:10 + 3 mol % CPL-4-1k |
| E: | $^3$[H]CHE-LUV | DOPE:DODAC:PEGC20::84:6:10 + 4 mol % CPL-4-1k |

Experiments used 100 C57/b16 mice, female, 18–23 g all ordered from Harlan Sprague Dawley. All animals housed in cages of 4 animals per group in 25 groups.

TABLE 12

| Group | Mice | Treatment | Time-point | Assay |
|---|---|---|---|---|
| A | 4 | A:DOPE:DODAC:PEGC20::84:6:10 | 15 min | PK |
| B | 4 | A:DOPE:DODAC:PEGC20::84:6:10 | 1 hr | PK |
| C | 4 | A:DOPE:DODAC:PEGC20::84:6:10 | 4 hr | PK |
| D | 4 | A:DOPE:DODAC:PEGC20::84:6:10 | 8 hr | PK |
| E | 4 | A:DOPE:DODAC:PEGC20::84:6:10 | 24 hr | PK |
| F | 4 | B:DOPE:DODAC:PEGC20::84:6:10 + 1 mol % CPL-4-1k | 15 min | PK |
| G | 4 | B:DOPE:DODAC:PEGC20::84:6:10 + 1 mol % CPL-4-1k | 1 hr | PK |
| H | 4 | B:DOPE:DODAC:PEGC20::84:6:10 + 1 mol % CPL-4-1k | 4 hr | PK |
| I | 4 | B:DOPE:DODAC:PEGC20::84:6:10 + 1 mol % CPL-4-1k | 8 hr | PK |
| J | 4 | B:DOPE:DODAC:PEGC20::84:6:10 + 1 mol % CPL-4-1k | 24 hr | PK |
| K | 4 | C:DOPE:DODAC:PEGC20::84:6:10 + 2 mol % CPL-4-1k | 15 min | PK |
| L | 4 | C:DOPE:DODAC:PEGC20::84:6:10 + 2 mol % CPL-4-1k | 1 hr | PK |
| M | 4 | C:DOPE:DODAC:PEGC20::84:6:10 + 2 mol % CPL-4-1k | 4 hr | PK |
| N | 4 | C:DOPE:DODAC:PEGC20::84:6:10 + 2 mol % CPL-4-1k | 8 hr | PK |
| O | 4 | C:DOPE:DODAC:PEGC20::84:6:10 + 2 mol % CPL-4-1k | 24 hr | PK |
| P | 4 | D:DOPE:DODAC:PEGC20::84:6:10 + 3 mol % CPL-4-1k | 15 min | PK |
| Q | 4 | D:DOPE:DODAC:PEGC20::84:6:10 + 3 mol % CPL-4-1k | 1 hr | PK |
| R | 4 | D:DOPE:DODAC:PEGC20::84:6:10 + 3 mol % CPL-4-1k | 4 hr | PK |
| S | 4 | D:DOPE:DODAC:PEGC20::84:6:10 + 3 mol % CPL-4-1k | 8 hr | PK |
| T | 4 | D:DOPE:DODAC:PEGC20::84:6:10 + 3 mol % CPL-4-1k | 24 hr | PK |
| U | 4 | E:DOPE:DODAC:PEGC20::84:6:10 + 4 mol % CPL-4-1k | 15 min | PK |
| V | 4 | E:DOPE:DODAC:PEGC20::84:6:10 + 4 mol % CPL-4-1k | 1 hr | PK |
| W | 4 | E:DOPE:DODAC:PEGC20::84:6:10 + 4 mol % CPL-4-1k | 4 hr | PK |
| X | 4 | E:DOPE:DODAC:PEGC20::84:6:10 + 4 mol % CPL-4-1k | 8 hr | PK |
| Y | 4 | E:DOPE:DODAC:PEGC20::84:6:10 + 4 mol % CPL-4-1k | 24 hr | PK |

Mice were treated with $^3$[H]CHE-LUV administered by tail vein I.V. in a total volume of 200 µl. Mice receive one treatment only. At the indicated time-points mice are weighed, sacrificed, and blood will be collected by cardiac puncture then evaluated for $^3$[H]CHE. Formulations are expected to be well tolerated. Mice are treated according to certified animal care protocols. Any mice exhibiting signs of distress associated with the treatment are terminated at the discretion of vivarium staff. All mice are terminated by $CO_2$ inhalation followed by cervical dislocation. Measurement of $^3$[H]CHE from blood is determined according to standard protocols.

Figure 40:
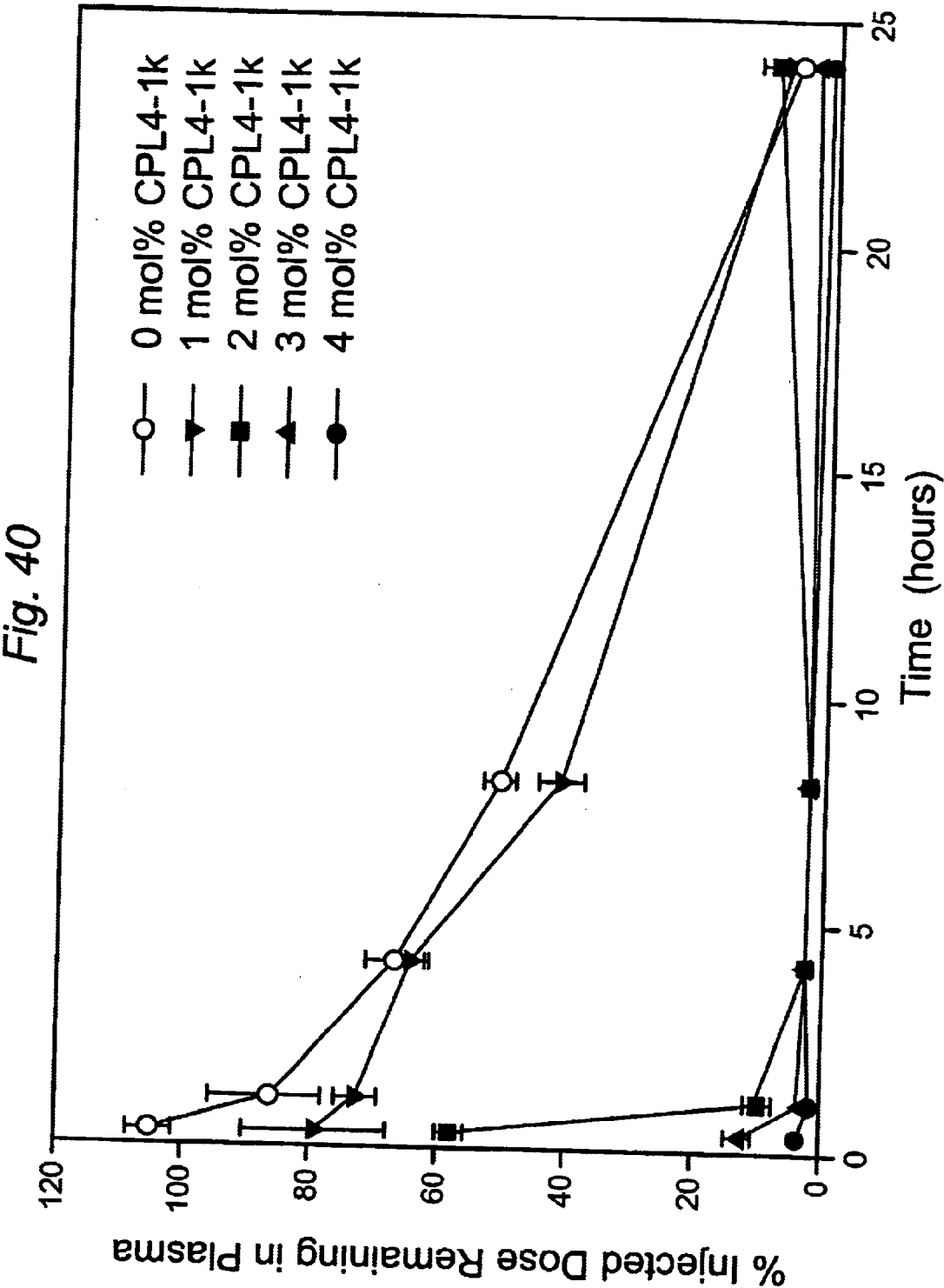
FIG. 40 illustrates in vivo pharmacokinetics of SPLP containing a short chain $CPL_4$.

In vivo pharmacokinetics of SPLP containing short chain $CPL_4$ are illustrated in FIG. 40. It is observed that that increasing amounts of the $CPL_4$ in the SPLP tends to increase the rate of clearance from the blood. $CPL_4$ incorporated a 1 mol % gives clearance results which are similar to SPLPs without $CPL_4$. Incorporation of higher amounts of CPL4 tends to increase the rate of clearance of the SPLP from the blood. SPLP-$CPL_4$[1k] (1%) shows best plasma clearance characteristics with a $t_{1/2}$ of 6–7 hours. Anything greater than 1 mol % clears more rapidly.

The results disclosed in this specification indicate a further refinement of SPLP technology. In particular, from these results it is clear that the type of CPL (i.e. the length of the polymer chain; and the amount of cationic charge per molecule) and the amount of such CPL in an SPLP must be optimized to obtain the best balancing of clearance properties in vivo with enhanced transfection ability. In vitro data has shown long chain CPLs and higher levels of such CPLs are to be preferred to increase transfection. However, as seen in previous comparisons of SPLPs versus lipid complexes, lipid formulations that work best in vitro are not best suited in vivo. In vivo results herein demonstrate that short chain CPLs incorporated at approximately 1% are optimized for circulation lifetimes in animals.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A vesicle comprising:
    (a) a cationic-polymer-lipid conjugate having the general structure of Formula I:

wherein:

A is a lipid moiety which acts as a lipid anchor;

W is a hydrophilic polymer; and

Y is a non-specific targeting polycationic moiety, said polycationic moiety having between about 2 to about 15 positive charges, wherein said positive charges are located away from the surface of the vesicle;

(b) a bioactive agent; and
    (c) a second lipid.

2. The vesicle according to claim 1, wherein Y is biocompatible.

3. The vesicle according to claim 1, wherein
    W is a polymer selected from the group consisting of PEG, polyamide, polylactic acid, polyglycolic acid, polylactic acid/polyglycolic acid copolymers and combinations thereof, said polymer having a molecular weight of about 250 to about 7000 daltons.

4. The vesicle according to claim 1, wherein W is PEG.

5. The vesicle according to claim 4, wherein said PEG has a molecular weight of 250 to about 3000.

6. The vesicle according to claim 4, wherein said PEG has a molecular weight of about 250 to about 1000.

7. The vesicle according to claim 4, wherein said second lipid is a PEG-lipid and W has a lower molecular weight than the PEG of said PEG-lipid.

8. The vesicle according to claim 4, wherein said second lipid is a $PEG_{3400}$-lipid and said compound of Formula I has a formula of

9. The vesicle according to claim 4, wherein said second lipid is a $PEG_{2000}$-lipid and said compound of Formula I has a formula of

10. The vesicle according to claim 4, wherein said second lipid is a PEG-lipid and W has a greater molecular weight that the PEG of said PEG-lipid.

11. The vesicle according to claim 4, wherein said second lipid is PEG$_{1000}$-lipid and said compound of Formula I has a formula of

A-PEG$_{3400}$-Y.

12. The vesicle according to claim 4, wherein said second lipid is PEG$_{1000}$-lipid and said compound of Formula I has a formula of

A-PEG$_{2000}$-Y.

13. The vesicle according to claim 1, wherein said bioactive agent comprises an anti-tumor drug.

14. The vesicle according to claim 13, wherein said antitumor drug is a member selected from the group consisting of actinomycin D, vincristine, vinblastine, cystine arabinoside, an anthracycline, an alkylative agent, a platinum compound, an antimetabolite, a nucleoside analog, methotrexate, a purine analog and a pyrimidine analog.

15. The vesicle according to claim 1, wherein said bioactive agent comprises a nucleic acid.

16. The vesicle according to claim 15, wherein said bioactive agent is a gene construct or an oligonucleotide.

17. The vesicle according to claim 1, further comprising a bilayer-stabilizing component.

18. The vesicle according to claim 17, wherein said bilayer stabilizing component is a PEG-lipid, wherein said PEG of said PEG-lipid has a greater molecular weight than said polymer W.

19. The vesicle according to claim 17, wherein said bilayer stabilizing component is a ATTA-lipid, wherein said ATTA of said ATTA-lipid has a greater molecular weight than said hydrophilic polymer.

20. The vesicle according to claim 3, wherein W is a PEG.

21. The vesicle according to claim 20, said compound having Formula II:

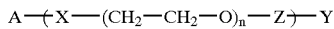

wherein:
X is a member selected from the group consisting of single bond and a functional group covalently attaching said hydrophobic lipid to at least one ethylene oxide unit or a single bond;

Z is a member selected from the group consisting of a single bond and a functional group covalently attaching said at least one ethylene oxide unit to a cationic head group or a single bond; and n is an integer ranging from about 6 to about 50.

22. The vesicle according to claim 21, wherein
A is a member selected from the group consisting of a diacylglycerolyl moiety, a dialkylglycerolyl moiety, a N-N-dialkylamino moiety, 1,2-diacyloxy-3-aminopropane moiety and a 1,2-dialkyl-3-aminopropane moiety.

23. The vesicle according to claim 21, wherein
X is a member selected from the group consisting of a single bond, phosphatidylethanolamino, phosphatidylethanolamido, phosphoro, phospho, phosphoethanolamino, phosphoethanolamido, carbonyl, carbamate, carboxyl, carbonate, amido, thioamido, oxygen, sulfur and NR, wherein R is a hydrogen or alkyl group.

24. The vesicle according to claim 21, wherein
Z is a member selected from the group consisting of a single bond, phospho, phosphoethanolamino, phosphoethanolamido, carbonyl, carbamate, carboxyl, amido, thioamido, an amino group, and NR, wherein R is a member selected from the group consisting of hydrogen atom and alkyl group.

25. The vesicle according to claim 1, wherein
said formulation is in the form of a member selected from the group consisting of a liposome, a micelle, a virosome, a lipid-nucleic acid particle, a nucleic acid complex and mixtures thereof.

26. The vesicle according to claim 25, wherein said lipid-based drug formulation is a liposome.

27. The vesicle according to claim 26, wherein said lipid-based drug formulation is a liposome having an average size in the range of about 0.05 to about 0.5 microns wherein said bioactive agent is a gene construct or an oligonucleotide.

28. A method of increasing an intracellular delivery of a bioactive agent, said method comprising administering to the cell the cationic lipid forming vesicle of claim 1, thereby increasing the intracellular delivery of the bioactive agent.

29. The method of claim 28, wherein said delivery is in vivo.

30. The method of claim 28, wherein said increasing is at least 10-fold compared to a cationic lipid forming vesicle without said cationic-polymer-lipid conjugate.

31. A method of increasing delivery to a target cell of a drug which is part of a parenterally administered lipid-based drug formulation, said method comprising: preparing a suspension of a lipid-based drug formulation comprising the cationic lipid forming vesicle of claim 1, wherein between 0.1 to 20 mole percent of said cationic-polymer-lipid conjugated is incorporated.

32. A method of administering a bioactive agent to a mammal, said method comprising: preparing a suspension of a lipid-based drug formulation comprising the cationic lipid forming vesicle of claim 1, wherein between 0.1 to 20 mole percent of said cationic-polymer-lipid conjugated is prepared, and a pharmaceutically acceptable amount of a bioactive agent, and parenterally administering said lipid-based drug formulation to said mammal.

33. A method for transfection of a cell with a lipid-based drug formulation, said method comprising: contacting said cell with a lipid-based drug formulation, which comprises the cationic lipid forming vesicle of claim 1, wherein between 0.1 to 20 mole percent of said cationic-polymer-lipid conjugate is incorporated.

34. A method for increasing transfection of a cell with a lipid-based drug formulation, said method comprising: contacting said cell with a lipid-based drug formulation, which comprises the cationic lipid forming vesicle of claim 1, wherein between 0.1 to 20 mole percent of said cationic-polymer-lipid conjugate is incorporated, whereby the transfection efficiency of said lipid-based formulation is increased compared to a lipid-based drug formulation without the incorporated cationic-polymer-lipid conjugate.

35. The vesicle according to claim 1, wherein Y comprises at least one basic amino acid or derivative thereof.

36. The vesicle according to claim 1, wherein Y has at least 8 positive charges at a selected pH.

37. The vesicle according to claim 1, wherein
Y is a member selected from the group consisting of lysine, arginine, asparagine, glutamine, derivatives thereof and combinations thereof.

38. The vesicle according to claim 1, wherein W is a polyamide polymer.

39. The vesicle according to claim 38, wherein W has a molecular weight of about 250 to about 2000 daltons.

40. The vesicle according to claim 21, wherein

A is a diacylglycerolyl moiety;

X is phosphoethanolamido;

Z is NR, wherein R is a hydrogen atom; and

Y is a member selected from the group consisting of about 1 to about 10 basic amino acids or derivatives thereof.

41. The vesicle according to claim 21, wherein

A is a diacylglycerolyl moiety having 2 fatty acyl chains, wherein each acyl chain is independently between 2 and 30 carbons in length and is either saturated or has varying degrees of saturation.

42. The vesicle according to claim 21, wherein

Y is a member selected from the group consisting of lysine, arginine, asparagine, glutamine, derivatives thereof and combinations thereof.

43. The vesicle according to claim 21, wherein

A is a diacylglycerolyl moiety having 2 fatty acyl chains, wherein each acyl chain is a saturated C-18 carbon chain; and Y is a cationic group having 4 lysine residues or derivatives thereof.

* * * * *